(12) United States Patent
Kunding

(10) Patent No.: US 11,035,854 B2
(45) Date of Patent: Jun. 15, 2021

(54) METHODS IN DIGITAL COUNTING

(71) Applicant: Selma Diagnostics APS, Copenhagen N (DK)

(72) Inventor: Andreas Hjarne Kunding, Copenhagen S (DK)

(73) Assignee: Selma Diagnostics APS, Copenhagen N (DK)

( * ) Notice: Subject to any disclaimer, the term of this patent is extended or adjusted under 35 U.S.C. 154(b) by 280 days.

(21) Appl. No.: 16/320,615

(22) PCT Filed: Jul. 28, 2017

(86) PCT No.: PCT/EP2017/069212
§ 371 (c)(1),
(2) Date: Jan. 25, 2019

(87) PCT Pub. No.: WO2018/020024
PCT Pub. Date: Feb. 1, 2018

(65) Prior Publication Data
US 2019/0154673 A1 May 23, 2019

Related U.S. Application Data

(60) Provisional application No. 62/368,564, filed on Jul. 29, 2016.

(30) Foreign Application Priority Data

Apr. 11, 2017 (EP) .................................... 17165915

(51) Int. Cl.
G01N 33/543 (2006.01)
C12Q 1/68 (2018.01)
(Continued)

(52) U.S. Cl.
CPC ......... *G01N 33/54306* (2013.01); *C12Q 1/68* (2013.01); *G01N 15/02* (2013.01);
(Continued)

(58) Field of Classification Search
CPC .. G01N 33/54306; G01N 15/02; G01N 15/14; G01N 33/48721; G01N 2015/0038;
(Continued)

(56) References Cited

U.S. PATENT DOCUMENTS

| | | | |
|---|---|---|---|
| 6,849,462 | B1 | 2/2005 | Winkler et al. |
| 2004/0009543 | A1 | 1/2004 | Kiechl et al. |

(Continued)

FOREIGN PATENT DOCUMENTS

| | | |
|---|---|---|
| CN | 102890474 A | 1/2013 |
| CN | 104531853 A | 4/2015 |

(Continued)

OTHER PUBLICATIONS

Kim, Soo Hyeon, et al. "Large-scale femtoliter droplet array for digital counting of single biomolecules." Lab on a Chip 12.23 (2012): 4986-4991. (Year: 2012).*

(Continued)

*Primary Examiner* — Samuel P Siefke
*Assistant Examiner* — Oyeleye Alexander Alabi
(74) *Attorney, Agent, or Firm* — Womble Bond Dickinson (US) LLP

(57) ABSTRACT

The present invention relates to methods and systems for testing for the presence of a material such as one or more analyte types within a sample and more particularly, for improved single enzyme-linked immunosorbent assay (sELISA) testing as well as other variants of single-enzyme linked molecular analysis (SELMA). Background and false positives are reduced due to the presence of at least two detection cycles where each detection cycle comprises the (Continued)

steps of a) triggering a signal from captured and labelled analyte(s), b) recording of the number and positions of capture sites exhibiting a signal from the captured and labelled analyte(s), c) and before a further detection cycle is performed, deactivation of signal(s).

16 Claims, 18 Drawing Sheets

Specification includes a Sequence Listing.

(51) Int. Cl.
 G01N 15/02 (2006.01)
 G01N 15/14 (2006.01)
 G01N 33/487 (2006.01)
 G01N 15/00 (2006.01)
 G01N 15/08 (2006.01)
(52) U.S. Cl.
 CPC ....... *G01N 15/14* (2013.01); *G01N 33/48721* (2013.01); *G01N 2015/0038* (2013.01); *G01N 2015/0053* (2013.01); *G01N 2015/0096* (2013.01); *G01N 2015/0873* (2013.01); *G01N 2015/1486* (2013.01)
(58) Field of Classification Search
 CPC ... G01N 2015/0053; G01N 2015/0096; G01N 2015/0873; G01N 2015/1486; C12Q 1/68
 See application file for complete search history.

(56) References Cited

U.S. PATENT DOCUMENTS

| | | |
|---|---|---|
| 2004/0018491 A1 | 1/2004 | Gunderson et al. |
| 2004/0058450 A1 | 3/2004 | Pamula et al. |
| 2005/0244863 A1 | 11/2005 | Mir |
| 2007/0218452 A1 | 9/2007 | Delattre et al. |
| 2007/0238096 A1 | 10/2007 | Reich et al. |
| 2008/0026379 A1 | 1/2008 | Siddiqi et al. |
| 2009/0142755 A1 | 6/2009 | Albitar |
| 2010/0075407 A1 | 3/2010 | Duffy et al. |
| 2010/0112342 A1 | 5/2010 | Cho |
| 2012/0190030 A1 | 7/2012 | Chun et al. |
| 2013/0052649 A1 | 2/2013 | Lee et al. |
| 2014/0087386 A1 | 3/2014 | Chiu et al. |
| 2014/0243223 A1* | 8/2014 | Duffy .............. G01N 33/54386 506/9 |
| 2014/0248610 A1 | 9/2014 | McKernan et al. |
| 2017/0168040 A1 | 6/2017 | Turner et al. |
| 2019/0154673 A1* | 5/2019 | Kunding .......... G01N 33/48721 |

FOREIGN PATENT DOCUMENTS

| | | |
|---|---|---|
| CN | 104535769 A | 4/2015 |
| EP | 1 156 329 A2 | 11/2001 |
| EP | 1 626 278 A2 | 8/2005 |
| EP | 2 565 279 A1 | 3/2013 |
| EP | 3 048 445 A2 | 7/2016 |
| JP | 2006-88034 A | 4/2006 |
| JP | 2009-068995 A | 4/2009 |
| JP | 2020-515074 | 5/2010 |
| JP | 4 531055 B2 | 8/2010 |
| JP | 2010-538260 A | 12/2010 |
| JP | 2014-21025 A | 2/2014 |
| WO | WO 98/47003 A1 | 10/1998 |
| WO | WO 01/61054 A2 | 8/2001 |
| WO | WO 2008/053406 A1 | 5/2008 |
| WO | WO 2008/081203 A2 | 7/2008 |
| WO | WO 2009/029073 A1 | 3/2009 |
| WO | WO 2009/109753 A2 | 9/2009 |
| WO | WO 2010/019388 A2 | 2/2010 |
| WO | WO 2010/039180 A2 | 4/2010 |
| WO | WO 2011/097028 A1 | 8/2011 |
| WO | WO 2011/109364 A3 | 9/2011 |
| WO | WO 2012/022482 A1 | 2/2012 |
| WO | WO 2012/072822 A1 | 6/2012 |
| WO | WO 2012/100198 A2 | 7/2012 |
| WO | WO 2012/135730 A2 | 10/2012 |
| WO | WO 2013/063230 A1 | 5/2013 |
| WO | WO 2013/110146 A2 | 8/2013 |
| WO | WO 2013/176767 A1 | 11/2013 |
| WO | WO 2014/001459 A1 | 1/2014 |
| WO | WO 2015/061362 A1 | 4/2015 |
| WO | WO 2015/109020 A1 | 7/2015 |
| WO | WO 2016/161402 A1 | 10/2016 |
| WO | WO 2017/004463 A1 | 1/2017 |
| WO | WO 2017/034970 A1 | 3/2017 |
| WO | WO 2017/048815 A1 | 3/2017 |

OTHER PUBLICATIONS

Rissin, David M., et al. "Single-molecule enzyme-linked immunosorbent assay detects serum proteins at subfemtomolar concentrations." Nature biotechnology 28.6 (2010): 595-599 (Year: 2010).*
Witters, Daan, et al. "Digital biology and chemistry." Lab on a Chip 14.17 (2014): 3225-3232. (Year: 2014).*
Ackermann, B., et anon, Corrections for "Kinetics of alkaline phosphatase from pig kidney. Influence of complexing agentse on stability and activity," *Biochemical Journal*, 1976, vol. 153, pp. 151-157.
Bigelow, W., et al., "Oleophobic Monolayers. I. Films Adsorbed From Solution in Non-Polar Liquids," from the Naval Research Laboratory, Washington, D.C., 1946, pp. 513-538.
Birdi, K., et anon, "A Study of the Evaporation Rates of Small Water Drops Placed on a Solid Surface," *J. Phys. Chem.*, 1989, vol. 93,pp. 3702-3703.
Dressman, D., et al., "Transforming single DNA molecules into fluorescent magnetic particles for detection and enumeration of genetic variations," *PNAS*, 2003, vol. 100(15), pp. 8817-8822.
Gorris, et anon, "Mechanistic Aspects of Horseradish Peroxidase Elucidated throuigh Single-Molecule Studies," *J. Am. Chem. Soc.*, 2009,vol. 131, pp. 6277-6282.
Huebner, A., et al., "Static microdroplet arrays: a microfluidic device for droplet trapping, incubation and release for enzymatic and cell-based assays," *Lab Chip*, 2009, vol. 9, pp. 692-698.
Kim, S., et al., "Large-scale femtoliter droplet array for digital counting of single biomolecules," *Lab Chip*, 2012,vol. 12, pp. 4986-4991.
Kunding, A., et al., "Micro-droplet arrays for micro-compartmentalization using air/water interface," *Lab Chip*, 2018, vol. 18, pp. 2797-2805.
Li, Z., et al., "Detection of Single-Molecule DNA Hybridization Using Enzymatic Amplification in anArray of Femtoliter-Sized Reaction Vessels," *J. Am. Chem. Soc.*, 2008, vol. 130, pp. 12622-12623.
Lien, E., et anon., "Partition Coefficients," *Encyclopedia of Phamraceutical Technology*, Informa Healthcare USA, 2007, pp. 2595-2603.
Mao, L., et al., "Horseradish Peroxidase Inactivation: Heme Destruction and Influence of Polyethylene Glycol," *Scientific Reports*, 2013, vol. 3(3216), pp. 1-7.
Pekin, D., et al., "Quantitative and sensitive detection of rare mutations using droplet-based microfluidics," *Lab Chip*, 2011, vol. 11, pp. 2156-2166.
Pohl, G., el anon, "Principle and applications of digital PCR," *Expert Rev. Mol. Diagn.*, 2004, vol. 4(1), pp. 41-47.
Rissin, D., er al., "Single-molecule enzyme-linked immunoabsorbent assey detects serum proteins at subfemtomolar concentrations," *Nature Biotechnology*, 2010, vol. 28(6), p. 595-600.
Ritchie, J., el al., "Metastable Sessile Nanodroplets on Nanopatterned Surfaces," *The Journal of Physical Chemistry*, 2012, vol. 116, pp. 8634-8641.
Sasagawa, K., et al., "Lensless CMOS-Based Imaging Device for Fluorescent Femtoliter Droplet Array Counting," *17th International Conference on Miniaturized Systems for Chemistry and Life Sciences*, Freiburg, Germany, 2013, vol. 3, pp. 1565-1567.

(56) References Cited

OTHER PUBLICATIONS

Temiz, Y., el al., "Lab-on-a-chip devices: How to close and plug the lab?," *Microelectronic Engineering*, 2015, vol. 132, pp. 156-175.
Vogelstein, B., et anon, "Digital PCR," *Proc. Natl. Acad. Sci. USA*, 1999, vol. 96, pp. 9236-9241.
Weinrich, D.,el al., "Applications of Protein Biochips in Biomedical and Biotechnological Research," *Angew. Chem. Int. Ed.*, 2009, vol. 48, pp. 7744-7751.
Witters, D., et al., "Digital microfluidics-enabled single-molecule detection by printing and sealing single magnetic beads in femtoliter drops," *Lab Chip*, 2013, vol. 13, pp. 2047-2054.
Witters, D., et al., "Digital biology and chemistry," *Lab Chip*, vol. 14, pp. 3225-3232.
Guo, Q., et al., "A molecular beacon microarray based on a quantum dot label for detecting single nucleotide polymorphisms," *Biosensors and Bioelectronics*, 2016, vol. 77, pp. 107-110.

\* cited by examiner (i)

(ii)

METHODS IN DIGITAL COUNTING

CROSS-REFERENCE TO RELATED APPLICATIONS

This application is a national stage filing under 35 U.S.C. 371 of PCT/EP2017/069212 filed Jul. 28, 2017, which International Application was published by the International Bureau in English on Feb. 1, 2018, and claims priority from U.S. Provisional Patent Application No. 62/368,564, filed Jul. 29, 2016, International Application PCT/EP2016/074045,filed Oct. 7, 2016, and European Application No. 17165915.4, filed Apr. 11, 2017, which applications are hereby incorporated by reference in their entirety in this application.

FIELD OF THE INVENTION

The present invention relates to methods for testing for the presence of a material such as one or more analyte types within a sample and more particularly for improved single enzyme-linked immunosorbent assay (sELISA) testing as well as other variants of single-enzyme linked molecular analysis (SELMA). The present invention thus further relates to improvements in single molecule digital counting analysis such as reduction of false-positive detections and/or background noise.

BACKGROUND OF THE INVENTION

Many approaches for the detection of single molecules has been developed by scientists in the previous decades thus enabling highly sensitive measurements of various types of molecules including single oligonucleotides, single proteins and single peptides. Single molecule measurements are used for digital detection or digital diagnostic tests in which single (or few) analyte molecules are confined to compartments, where the compartments provide a suitable environment for detecting the presence of the single analyte. For example, in the case of single enzyme-linked immunosorbent assay (sELISA), single immunocomplexes comprising an analyte molecule sandwiched between a capture antibody and an enzyme-linked detection antibody are placed in individual micro-compartments and finally supplied with fluorogenic or chromogenic enzyme substrate to produce a detectable optical signal within the compartment. Another example is digital polymerase chain reaction (dPCR), where single oligonucleotide analytes are co-encapsulated with PCR primers and PCR mixture in compartments, hence leading to the analyte-templated exponential amplification of fluorescence-labeled amplicons.

Despite the merits of state-of-the-art digital detection, a major challenge in the field is to suppress undesired background noise. Background noise typically arises when samples composed of complex mixtures of molecules are analyzed. For example, in the case, when a sample derived from blood is analyzed by sELISA, the background noise comes about mainly by two mechanisms:

Mechanism 1: During the sample processing, predominantly target analytes form immunocomplexes, however, both capture and detection antibodies are not able to differentiate perfectly between the target analytes and similar non-target molecules (also named non-target compounds herein) (proteins, peptides, etc.) present in the sample, and consequently a small fraction of non-target molecules will be able to form immunocomplexes as well. Because the concentration of non-target molecules usually is several orders of magnitudes greater than the concentration of the target molecules, even a small fraction of "false" immunocomplexes can overwhelm the number of target analyte immunocomplexes.

Mechanism 2: The aforementioned inability of antibodies to distinguish perfectly between target and non-target, allows for non-specific binding/adsorption of enzyme-linked detection antibodies to regions or compartments, where no target analyte is present. This issue may be reduced by improving the surface chemistry in the test, such that detection antibodies bind non-specifically to a lesser extent. However, complete negation of non-specific binding is not possible to achieve experimentally, thus leading to "false" signals originating from single enzyme-linked detection antibodies only.

These two mechanisms have been discussed in single-molecule detection literature for example in the research article of D. M. Rissin et al entitled "Single-molecule enzyme-linked immunosorbent assay detects serum proteins at subfemtomolar concentrations" published in *Nature Biotechnology* (2010), vol. 28, pp. 595-599 (DOI: 10.1038/nbt.1641). In the research article, Rissin and colleagues describes an approach to sELISA and reports a limit-of-detection (LOD) of 220 zeptomolar (also termed $220 \times 10^{-21}$ M, approx. 15 molecules) when analyzing a calibration sample. However, when the calibration sample was replaced with a serum sample the LOD increased three orders of magnitude to approx. 200 attomolar (also termed $200 \times 10^{-18}$ M or 200 aM, approx. 12,000 molecules). This dramatic reduction in sensitivity can be understood from the way non-target compounds in the serum interferes with the specific interaction between target analyte and the detection/capture antibody-pair, as described in mechanisms 1 and 2.

Mechanism 1 may also apply to other cases of analyte molecules apart from proteins and peptides. A prominent example of this is detection of single base-pair substitutions and/or single nucleotide polymorphisms (SNPs) by means of polymerase chain reaction (PCR). Here, PCR primers specific to the SNP is applied to specifically amplify oligonucleotide analytes containing the SNP sequence. However, SNP detection is highly challenging, because normally a sample may contain a high concentration of wildtype non-target oligonucleotides, which to a high degree interferes with the SNP-specific PCR primers. By use of highly optimized primers, conventional PCR detection may reliably detect one SNP oligonucleotide molecule in a background of 100 wildtype molecules (100:1 ratio). If the ratio of wildtype-to-target increases further, then false positive results will be produced. In the case of dPCR, higher ratios of wildtype-to-target may be tolerated because single (or few) oligonucleotides are encapsulated in individual compartments. Hence, for the individual compartment the wildtype-to-target ratio is highly favorable, i.e. 0:1, 1:0 or 1:1 for compartments containing a single SNP analyte oligonucleotide, a single wildtype oligonucleotide and one of each, respectively. Nevertheless, to achieve reliable encapsulation of single (or few) oligonucleotides per compartment, the majority of compartments have to be empty, see for example the research article by D. Pekin et al entitled "Quantitative and sensitive detection of rare mutations using droplet-based microfluidics" published in *Lab on a Chip* (2011), vol. 11, pp. 2156-2166 (DOI: 10.1039/c11c20128j). A general rule for dPCR is to prepare 5-10 times more compartments than the expected number of wildtype+target molecules in the sample, thus essentially discarding the majority of prepared compartments from analysis.

Scientists are developing techniques for analyzing changes in biological and chemical systems, where these changes often relate to the switching between two or more states. For example, Witters et al. in Digital Biology and Chemistry (DOI: 10.1039/C4LC00248B, (Frontier) Lab on a Chip, 2014, 14, pp. 3225-3232) discuss the development of various digital biological and chemical technologies. These digital technologies can work quite well, as digital techniques offer advantages in terms of robustness, assay design, and simplicity because quantitative information can be obtained with qualitative measurements. However, digital techniques can be relatively complex, in part due to the technical difficulty in isolating and manipulating single molecules. For example, some techniques use micron-sized magnetic beads to process samples of femtoliter volumes. See Rissin et al., in Single-molecule enzyme-linked immunosorbent assay detects serum proteins at subfemtomolar concentrations (DOI:10.1038/nbt.1641, Nature Biotechnology 2010, 28, pp. 595-599). Other techniques use even smaller volumes of attoliters. These tiny volumes can create challenges because the fluid dynamics of small volumes present behaviors, at typical laboratory temperature and pressure that make processing difficult.

For example, most digital detection techniques rely on the micro-compartmentalization of a liquid containing analytes and various detection- and capture-probes. The analytes and detection/capture probes are carried, or exist within, micron-sized droplets, typically of pico-to-attoliter volumes.

Therefore, the way to partition the sample in to smaller volumes is an important part of a digital detection process. The most readily available device format relies on solid or polymeric substrates forming an array of micro-compartments into which the sample can be transferred. These arrays mainly come in two varieties; (i) the micro-well arrays and (ii) the capillary arrays. In a micro-well array, the compartment is made up by a recess in the substrate, whereas in a capillary array the compartment extends all the way through the substrate, thus forming a through hole. A major challenge inherent in both of these array types is the way that they are loaded with sample and accessory reagents. In the micro-well array, the recess may not readily be filled up with a liquid sample, because air cannot leave the well due to the microscopic dimensions of the well, as an example of this see the research article by Kim et al. entitled "Large-scale femtoliter droplet array for digital counting of single biomolecules" published in Lab on a Chip, (2012) vol. 12, pp. 4986-4991 (DOI: 10.1039/c2lc40632b). This problem is absent from capillary arrays, because each compartment has two openings, such that if the liquid sample is added from the top opening, then air can escape through the bottom opening. However, when it comes to exchanging the liquid held within the micro-well or capillary compartments with another liquid, an additional issue arises, which is caused by the slow diffusion of molecules. Because both the micro-wells and capillaries are positioned perpendicular to the flow of the liquid phase being added, then good mixing cannot take place, and hence liquid exchange can only take place by molecular diffusion from the bulk liquid into the capillary and vice versa. Consequently, to ensure proper liquid exchange a time-delay (the length of which will depend on the dimensions of the micro-wells/capillaries and the type of molecular species being added) will have to be applied.

To overcome these challenges a third kind of array has been developed, which will be referred to as surface-tension arrays. A surface-tension array is planar and consists of hydrophilic features patterned in or onto a hydrophobic substrate. When a surface-tension array is contacted with an aqueous sample (e.g. by immersion into the aqueous phase and withdrawal of the array) individual droplets may form on the hydrophilic features due to the surface-tension difference between the features and the surrounding substrate. Because the droplets rest on a planar surface, then liquid loading as well as liquid exchange may take place instantaneously (or at least several orders of magnitude faster than for diffusion-limited transport) when a liquid sample is introduced on the array. Unlike the micro-well array, no air can be trapped beneath the liquid and the hydrophilic features and since the array does not rely on depressions/recesses/cavities in the substrate, then liquid mixing between droplets and the bulk liquid is not limited by molecular diffusion. However, all three types of micro-compartmentalization formats (micro-well, capillary and surface tension arrays) are facing the challenge of preserving a large number of liquid micro-droplets for a sufficient long time in order to allow digital counting to be conducted.

At typical ambient temperature and pressure for a laboratory, these microdroplets evaporate within seconds, see for example the research article by Birdi, K. S., Vu, D. T. and Winter, A. entitled "A study of the evaporation rates of small water drops placed on a solid surface" published in The Journal of Physical Chemistry, 1989, vol. 93, pp. 3702-3703 (DOI: 10.1021/j100346a065).

Once evaporated, the ability to process the molecule within the microdroplet is gone, the digital technique cannot be carried out.

Accordingly, it is necessary to prevent rapid evaporation and maintain the microdroplet of a period of time sufficient to measure for the presence of the molecule of interest.

To this end, scientists and engineers have developed certain techniques that seal the compartments that are holding the microdroplets. These seals prevent the microdroplets from contacting the ambient environment and thus prevent evaporation.

There are in general two techniques for sealing a compartment: a physical seal and a chemical seal. The physical seal is used when the compartments are structured as micro-recesses or micro-cavities in a substrate. To physically seal the compartments, an air-tight lid is attached on top of the compartments. In this way, the content of individual compartments cannot evaporate and neighboring compartments cannot exchange their content, which would otherwise lead to cross-contamination. The disadvantage of having a physical seal is that once the compartments have been sealed off, the analysis ends, because the lid cannot be easily removed without disrupting the integrity of the micro-compartments. Furthermore, to apply a physical seal, the compartments have to be structured as micro-wells/-cavities/-recesses, which, due to slow molecular diffusion, results in technical difficulties with exchanging the liquid in the compartments during the initial preparative steps.

One type of chemical seal relies on covering the compartments with an oil (or non-polar liquid) phase. In this way, evaporation of the sample is reduced, because water from the sample only slowly partitions into the oil phase. The advantage of a chemical seal is that it is based on interfacial tension, and hence the compartments do not need to be structured as cavities, but can instead be formed as droplets resting on a surface. This feature enables fast reagent exchange, which is not limited by molecular diffusion, but is instead determined by the flowrate at which the new reagent is introduced. Furthermore, unlike the physical seal, the chemical seal may be removed more easily by aspirating the oil phase from the sample. However, one of the disadvantages of a chemical seal is that analytes or other biomolecules from the sample may partition into the non-polar phase and lead to (i) sample loss and/or (ii) inter-droplet contamination. In particular, biomolecules such as proteins, are prone to be soluble in non-polar liquids, mainly due to the fact that hydrophobic amino acids in the protein may rearrange themselves upon exposure to a hydrophobic interface. This property of molecules to partition from water into a non-polar phase is described by the partition coefficient, i.e. oil-water partition coefficient, water-octanol partition coefficient, etc, e.g. in Lien, E. J. and Ren, S. S. in Chapter 186 in Encyclopedia of Pharmaceutical Technology, Third Edition, 2006, ISBN: 9780849393990. Furthermore, it has been shown that even water—although slowly—partitions into a surrounding oil phase, e.g. see the work of Huebner, A. et al published in Lab on a Chip, 2009, vol. 9, pp. 692-698 (DOI: 10.1039/B813709A). Even further, when a bulk aqueous phase is displaced by a bulk oil phase or vice versa there is a risk of producing emulsion droplets, i.e. micron-sized inclusions of water in oil or vice versa. Emulsion droplets may constitute an experimental nuisance, since they can foul the surfaces and/or deteriorate the flow-performance of the device.

WO2009029073 A1 entitled "Methods for determining the concentration of an analyte in solution" describes how to conduct single molecule digital counting in confined reaction vessels. WO2015061362 A1 entitled "Enrichment and detection of nucleic acids with ultrahigh sensitivity" describes how to prepare a non-sealed surface-tension array of liquid droplets exhibiting a fast evaporation rate. WO2013110146 A2 entitled "Patterning device" describes how to prepare a surface tension array of liquid droplets and how to use it for bioassays under a chemical seal. WO2013063230 A1 entitled "Device and method for apportionment and manipulation of sample volumes" describes methods for preparing and using chemically sealed surface-tension arrays for bioassays including digital counting measurements. JP2014021025A entitled "Apparatus and method for forming artificial lipid membrane" describes how to prepare a surface-tension array chemically sealed with a lipid membrane. WO2010039180 A2 entitled "High sensitivity determination of the concentration of analyte molecules or particles in a fluid sample" describes digital counting of analytes by dividing a sample into physically sealed micro-well compartments. WO2010019388 A2 entitled "Method and apparatus for discretization and manipulation of sample volumes" describes micro-well compartments, which may be used to capture and divide a liquid sample by applying a chemical seal comprised by one or more immiscible liquids. WO2012022482 A1 entitled "Microwell arrays for direct quantification of analytes on a flat sample" describes the use of physically sealed micro-well compartments for analyzing samples contained on a flat substrate. US20100075407 A1 entitled "Ultrasensitive detection of molecules on single molecule arrays" describes digital counting measurements conducted in physically sealed micro-well compartments. WO2012100198 A2 entitled "Methods and systems for performing digital measurements" describes a digital counting measurement conducted by preparing and analyzing arrays of liquid droplets. US20130052649 A1 entitled "Multilayer high density microwells" describes chemically sealed arrays of micro-well compartments for bioanalysis. WO2001061054 A2 entitled "Apparatus and methods for parallel processing of micro-volume liquid reactions" describes the use of chemically sealed capillary arrays for conducting bioassays. WO2014001459 A1 entitled "A method of charging a test carrier and a test carrier" describes the use of capillary arrays for conducting bioassays. WO1998047003 A1 entitled "An analytical assembly for polymerase chain reaction" describes digital counting of oligonucleotides. WO2011097028 A1 entitled "Systems and methods for manipulating a molecule in a nanopore" describes how to manipulate single molecules in a membrane nanopore. US2008026379 A1 entitled "Nucleotide analogs" describes sequential sequencing of single oligonucleotide molecules. US2009142755 A1 entitled "Assay for detecting genetic abnormalities in genomic nucleic acids" describes detection of nucleic acids by capturing on a solid support. US2012190030 A1 entitled "Detection of target nucleic acid sequences by cyclic exonucleolytic reactions" describes detection of nucleic acids without the use of polymerase chain reaction. WO2017034970 A1 entitled "Combinatorial single molecule analysis of chromatin" describes sequential labelling and detection of oligonucleotide/chromatin complexes on a solid support. EP3048445 A2 entitled "Method and apparatus for the analysis and identification of molecules" describes how single oligonucleotides may be sequenced using a nanopore.

Accordingly, there remains a need in the art for improved systems and methods for sealing compartments holding micro-droplets containing material being analyzed.

Until now repeated labelling has been applied to single molecule digital counting to achieve multiplexing, i.e. a greater number of target analyte types may become detected by using a labelling agent specific to analyte 1 in labelling reaction 1, a labelling agent specific to analyte 2 in labelling reaction 2, and so forth, see for example WO2009029073 A1 and WO2017034970 A1.

There further remains a need in the art for reduction of noise in analyses involving digital counting for example single-molecule detection or quantification. Reduction or prevention of noise leading to counting errors in digital counting could greatly improve the sensitivity and specificity of existing single molecule detection assays. In particular, improvements in terms of sensitivity and specificity of state-of-the-art single-molecule detection assays, where the assays are based on a labelling agent binding to an analyte, are challenged by (i) imperfect binding of the labelling agent to the analyte, (ii) cross-labeling of different analyte types and (iii) non-specific binding of the labelling agent to the capture site.

SUMMARY

The present inventor has surprisingly found that counting error such as false-positive detections and/or background noise in digital counting analysis may be greatly reduced by (i) using a plurality of discrete capture sites to capture analytes from a sample and (ii) subjecting the captured analytes to one or more detection cycles, where each detection cycle enables detection of signals from bound labelling agents followed by optional removal of the bound labelling agents. It has thus been found by the present inventor that background noise and in particular false-positive detections may be greatly reduced simply by labelling and re-labelling the same analyte with the same labelling agent in combination with recordation of what individual capture sites displayed a signal in each detection cycle.

Because non-specific binding interactions of the labelling agent to an empty capture site or to captured non-target molecules take place with a lower probability, as compared to the specific binding interaction of the labelling agent to the captured analyte, then repeated labelling of non-target molecules or repeated non-specific binding of labelling agents to an empty capture site is expected to become increasingly unlikely for each time the detection cycle is repeated. On the other hand, the specific labelling of captured analytes is expected to remain largely unaffected, and thus is more likely to repeatedly produce a signal in each detection cycle. Hence, non-specific interactions of the labelling agents become suppressed, thus leading to less counting error and consequently resulting in improved detection sensitivity and specificity.

In a first aspect disclosed herein, is a method for digital counting analysis of a sample potentially containing at least one analyte, wherein the sample has been contacted with a solid phase having a plurality of discrete capture sites, each site being capable of capturing the at least one analyte, which method comprises at least two detection cycles, where each detection cycle comprises the steps of
 a) triggering a signal from captured and labelled analyte(s),
 b) recordation of the number and positions of capture sites exhibiting a signal from the captured and labelled analyte(s),
 c) and before a further detection cycle is performed, deactivation of signal(s).

In a second aspect disclosed herein, is a method for digital counting analysis of a sample potentially containing at least one analyte, wherein the sample has been contacted with a solid phase having a plurality of discrete capture sites, each site being capable of capturing the at least one analyte, which method comprises at least two detection cycles, where each detection cycle comprises the steps of labelling the at least one analyte by adding a labelling agent and compartmentalize the at least one captured and labelled analyte to produce liquid compartments containing at least one analyte followed by steps a)-c):
 a) triggering a signal from the captured and labelled analyte(s),
 b) recordation of the number and positions of capture sites exhibiting a signal from the captured and labelled analyte(s),
 c) and before a further detection cycle is performed, deactivation of signal(s).

In a third aspect disclosed herein, is a method for digital counting analysis of a sample potentially containing at least one analyte, wherein the sample has been contacted with a solid phase having a plurality of discrete capture sites, each site being capable of capturing the at least one analyte, wherein the at least one analyte is labelled by adding a labelling agent in a labelling step prior to or during capture of the at least one analyte on the solid phase, which method comprises at least two detection cycles, wherein the at least one captured and labelled analyte is compartmentalized to produce liquid compartments containing at least one analyte followed by steps a)-c):
 a) triggering a signal from the captured and labelled analyte(s),
 b) recordation of the number and positions of capture sites exhibiting a signal from the captured and labelled analyte(s),
 c) and before a further detection cycle is performed, deactivation of signal(s),
wherein step c) before a further detection cycle is performed is followed by a re-labelling step, wherein the at least one captured analyte is labelled by adding a labelling agent.

In a further aspect disclosed herein, is the use of a solid phase having a plurality of discrete capture sites, each site being capable of capturing the at least one analyte in a method as described herein.

In a further aspect disclosed herein, is the use of a solid phase having a plurality of discrete capture sites, each site being capable of capturing the at least one analyte in a method as described herein for reducing counting error in a digital counting analysis.

In a further aspect disclosed herein, is the use of a solid phase having a plurality of discrete capture sites, each site being capable of capturing the at least one analyte for reducing counting error in a digital counting analysis by performing at least two detection cycles as described herein.

In another aspect disclosed herein, is a method for digital counting of at least one or more distinct analyte types, the method comprising counting the analyte types contained in a plurality of liquid nano-to-attoliter droplets under a gas phase seal.

In another aspect disclosed herein, is a use of a plurality of liquid nano-to-attoliter droplets under a gas phase seal for digital counting of at least one or more distinct analyte types.

LEGENDS TO THE FIGURE

The foregoing and other objects and advantages of the invention will be appreciated more fully from the following further description thereof, with reference to the accompanying drawings wherein.

Figure 4:
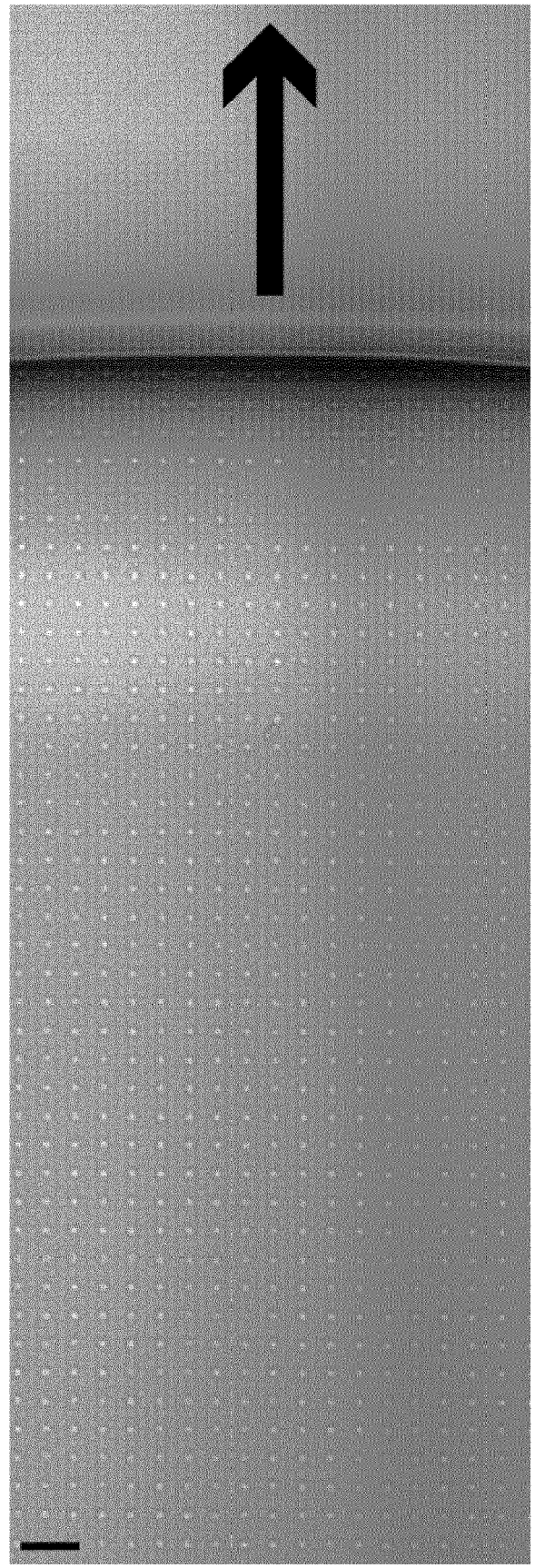
Figure 5:
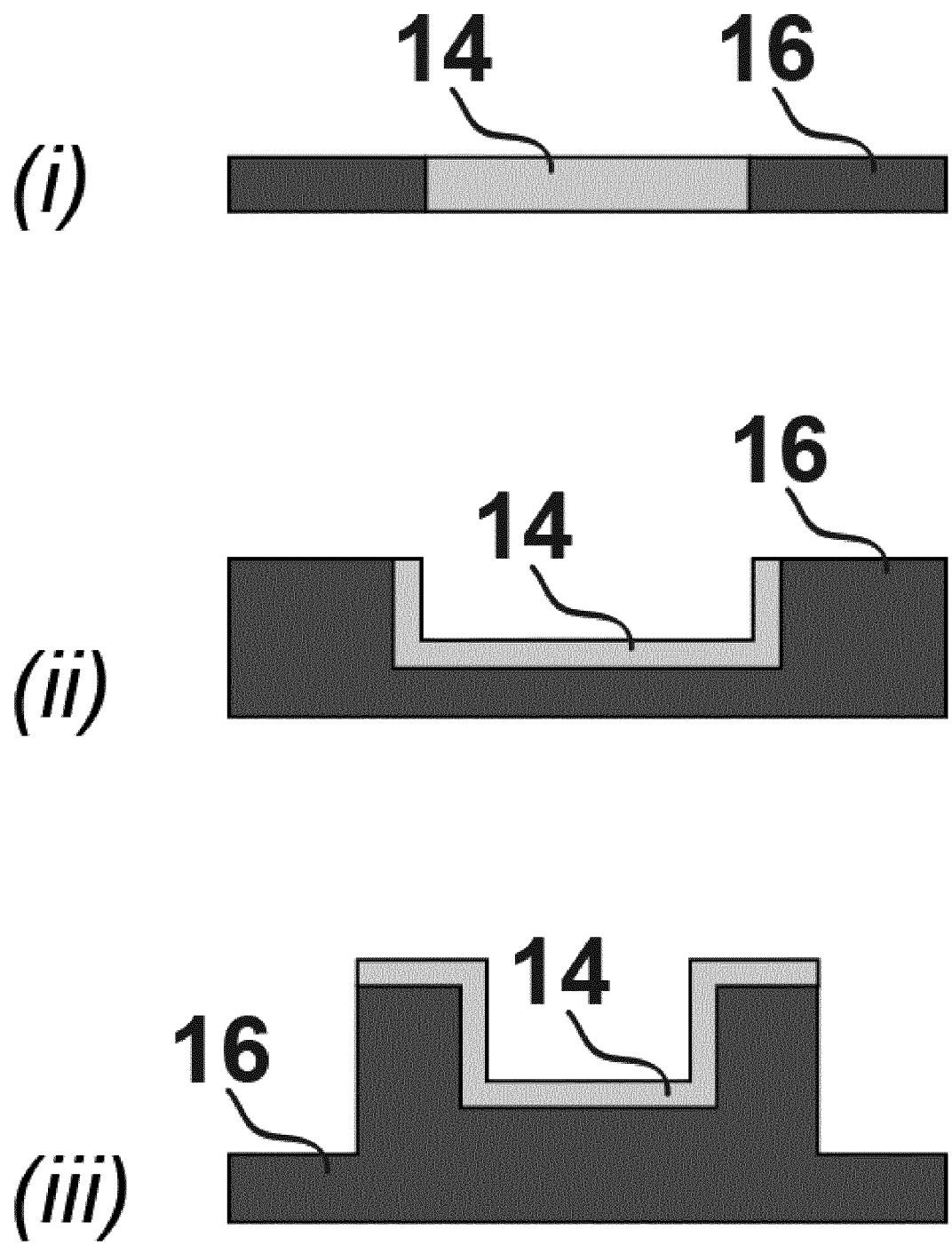
Figure 6:
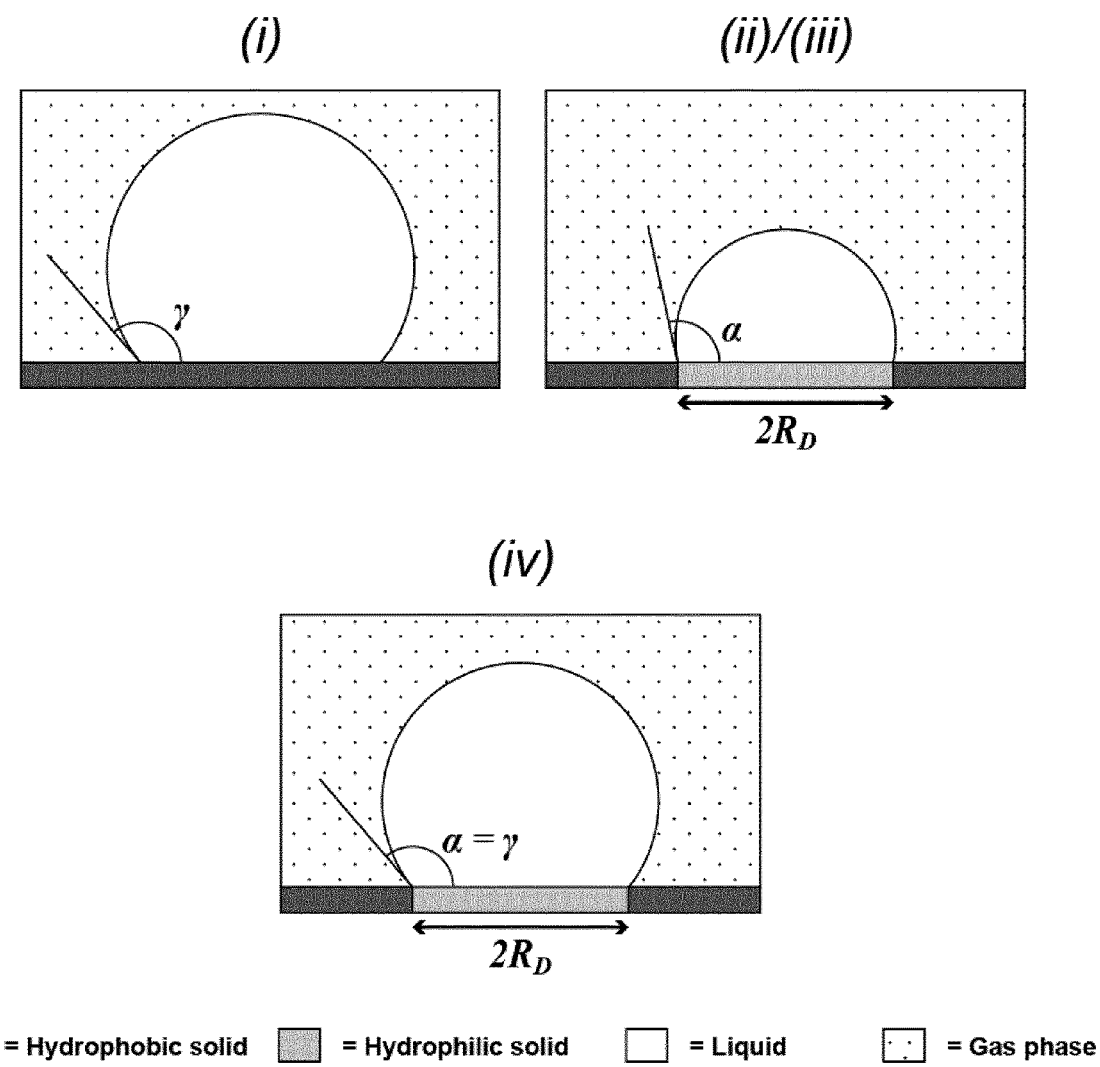
Figure 7:
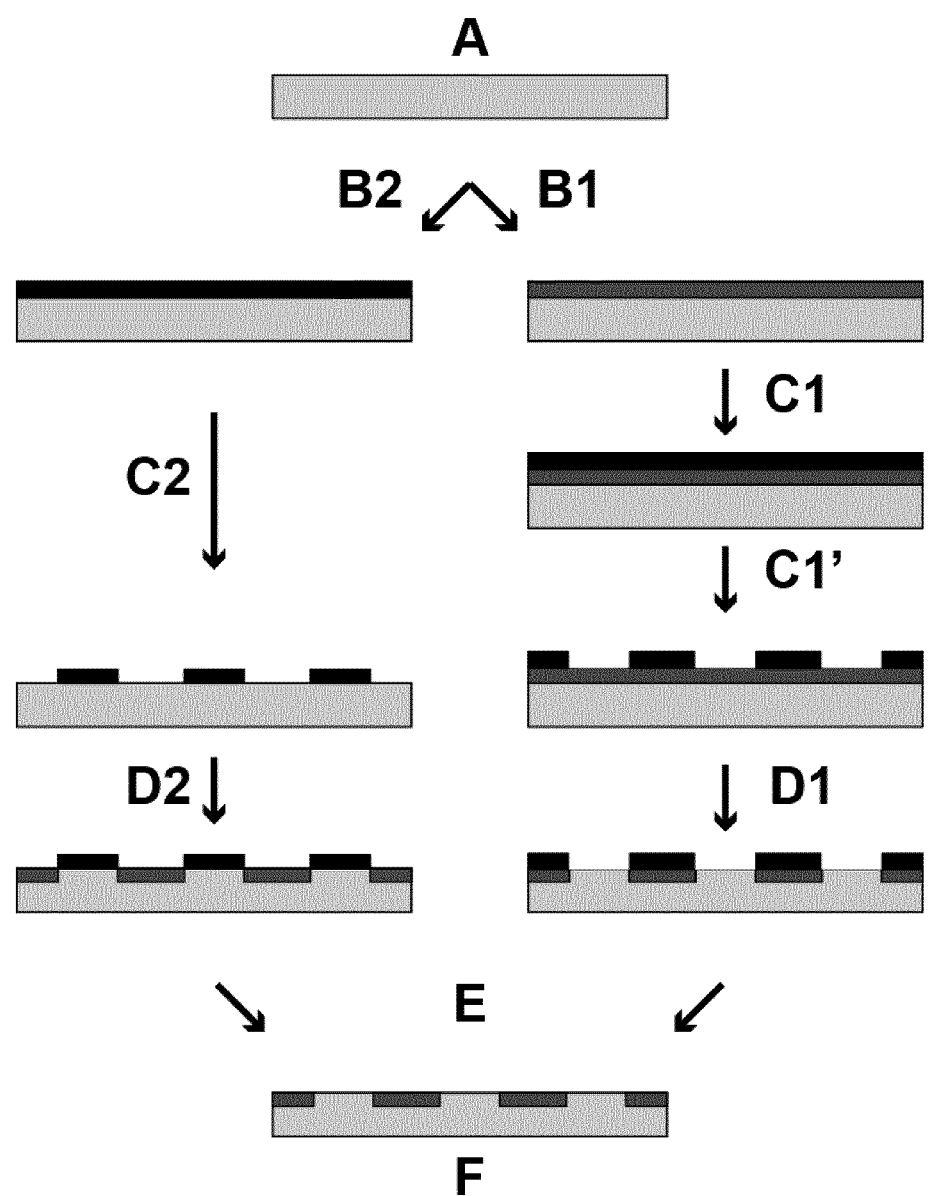

FIG. 4 depicts an exemplary representation of a process of drawing a fluid from the flow compartment to create a gas phase seal. The depiction is an excerpt from a brightfield micrograph acquired when the flow system is being operated, see Example 1-5. The scale bar on the brightfield micrograph is 20 μm;

FIG. 5 depicts exemplary representations of hydrophilic features 14 including (i) a planar feature, (ii) a feature shaped as a depression in the hydrophobic substrate 16 and (iii) a feature comprising a protrusion from the hydrophobic substrate in which a depression contains the hydrophilic zone. The sketch is not drawn to scale;

FIG. 6 depicts examples of liquid droplets in contact with a solid support. In this example, the following are shown on the sketches; examples of (i) the contact angle (γ) of a liquid droplet resting on a hydrophobic substrate in a gas atmosphere, (ii) the radius ($R_D$) of a circular planar hydrophilic feature, (iii) the contact angle (α) of a liquid droplet resting on a circular planar hydrophilic feature and (iv) the geometrical definition of the maximum droplet volume for a circular planar hydrophilic feature. The sketch is not drawn to scale;

FIG. 7 depicts two exemplary photolithography-based processes to prepare a pattern of planar hydrophilic features surrounded by a hydrophobic substrate. The illustrated steps comprise:
 A—providing a hydrophilic wafer substrate
 B2—deposition of photosensitive thin film coating; or
 B1—homogeneous surface modification of the wafer
 C2—UV exposure and development of the coating; or
 C1—deposition of photosensitive thin film coating, followed by C1'-UV exposure and development of the coating
 D2—hydrophobic surface modification of the wafer, or
 D1—selective etching of the hydrophobic layer E—removal of thin film coating, to achieve—F—a planar pattern of hydrophilic features.

Figure 8:
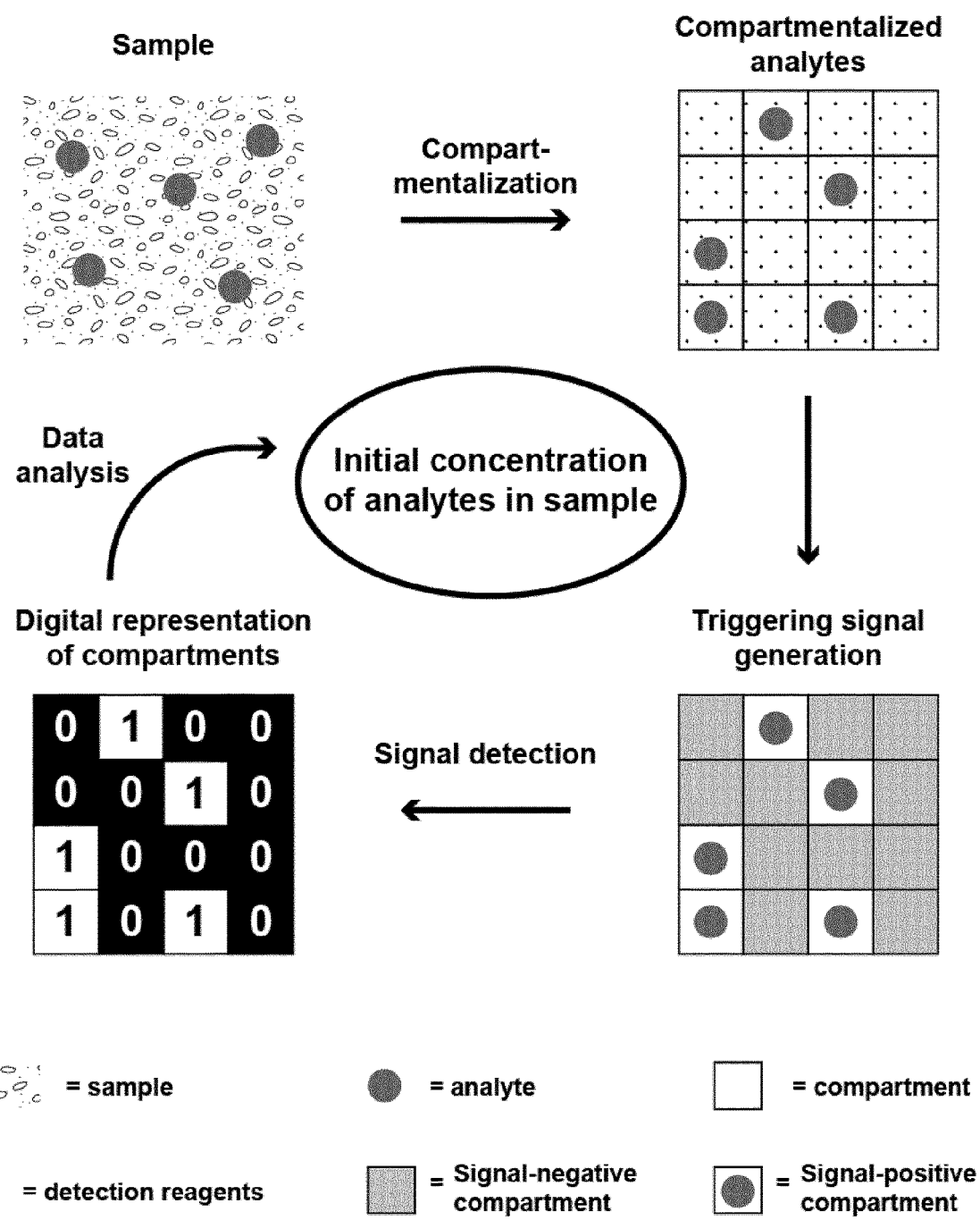
Figure 9:
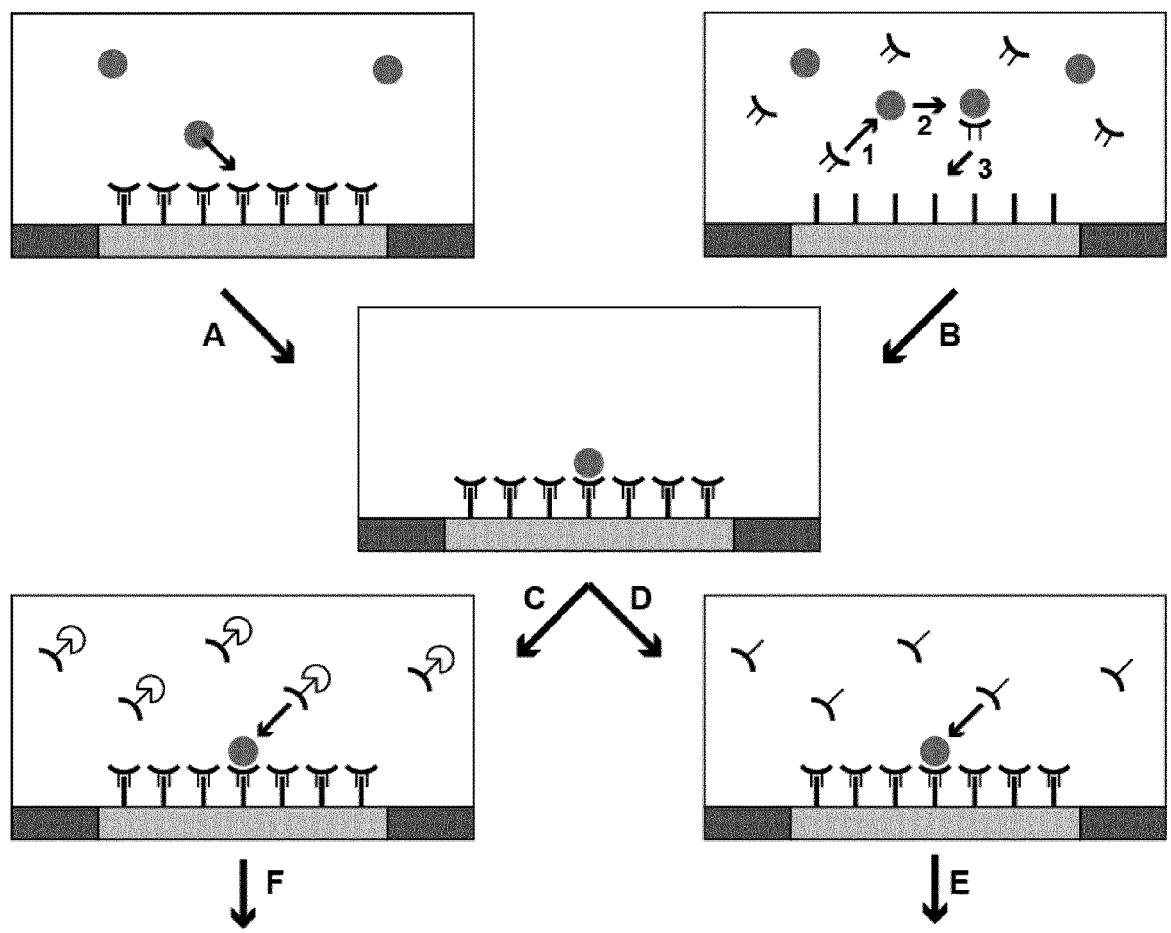
Figure 9:
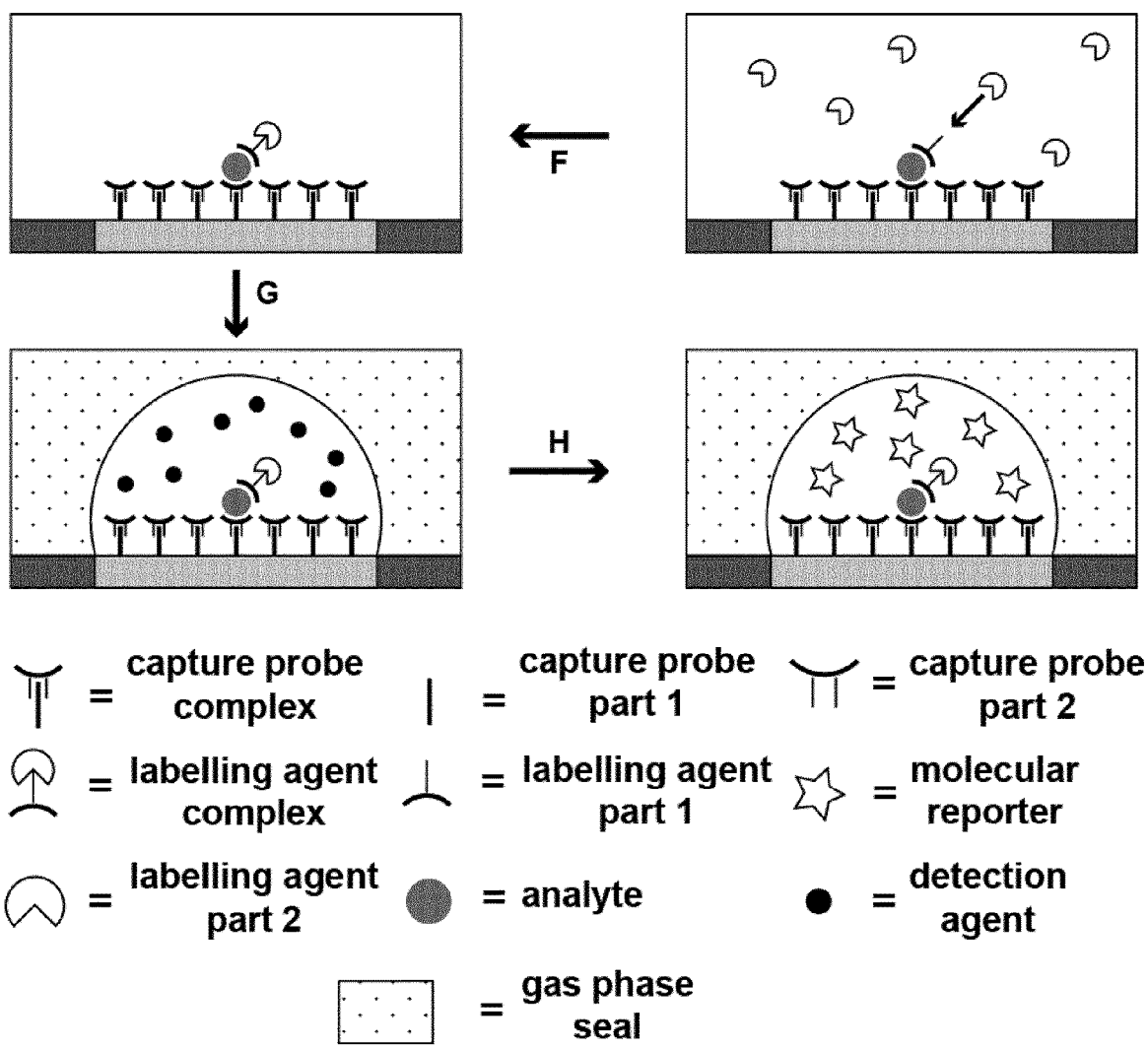
Figure 10:
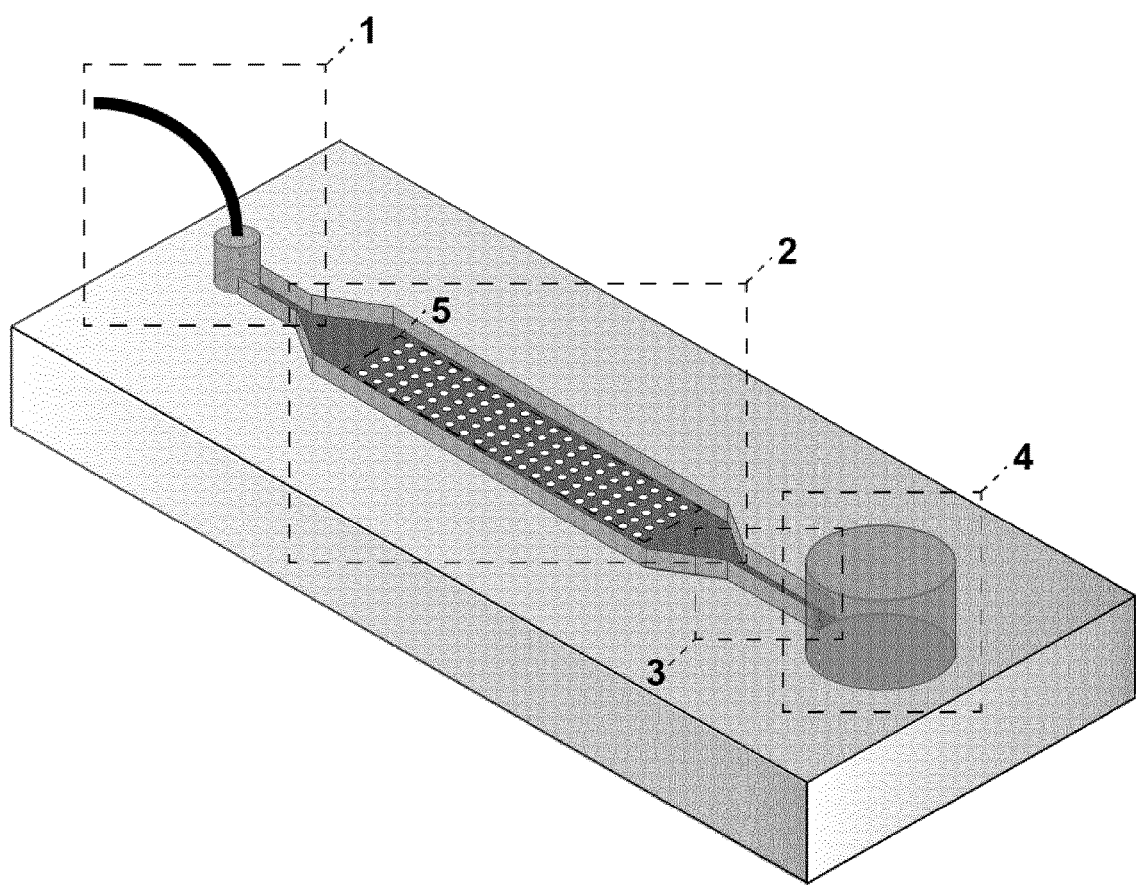
Figure 11:
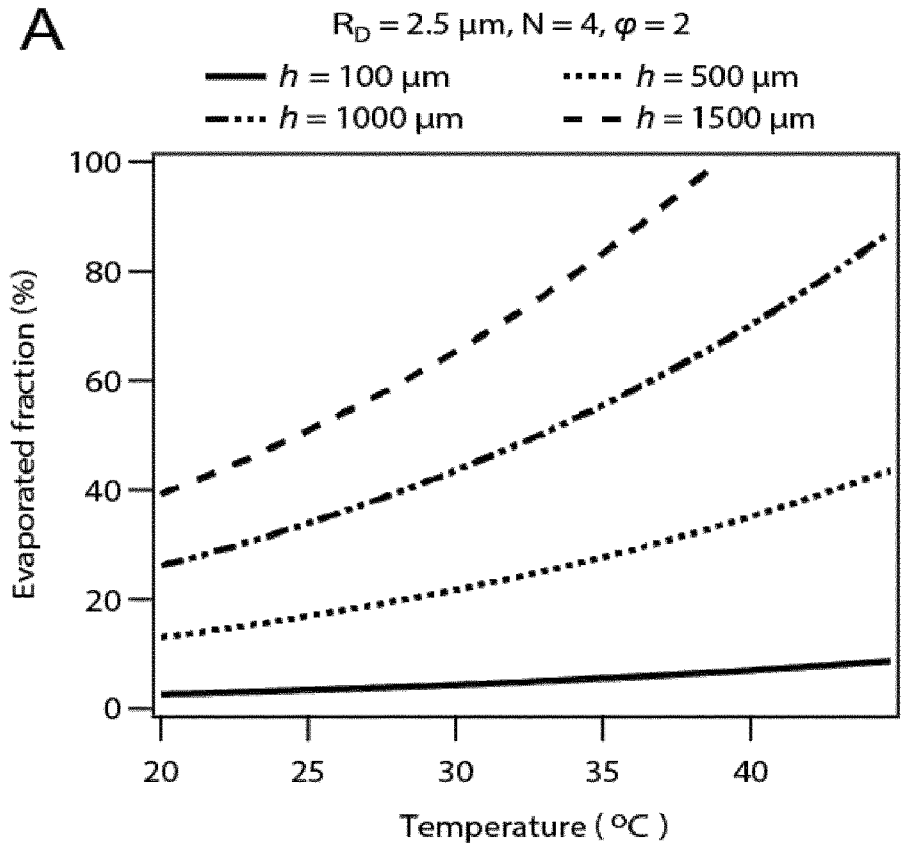
Figure 11:
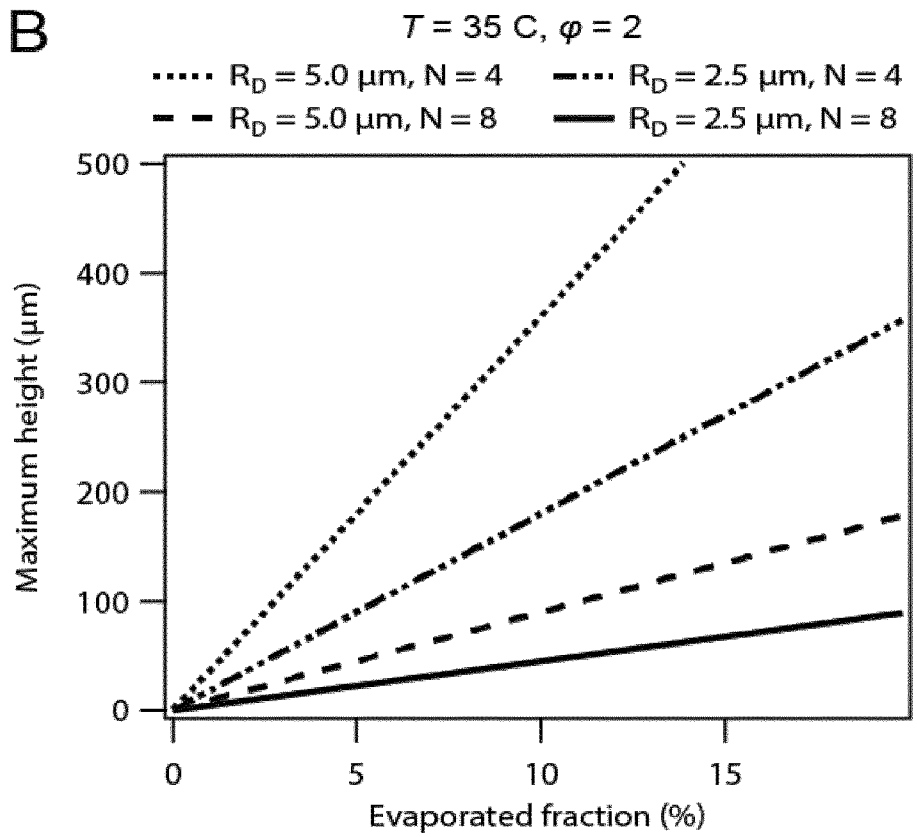
Figure 11:
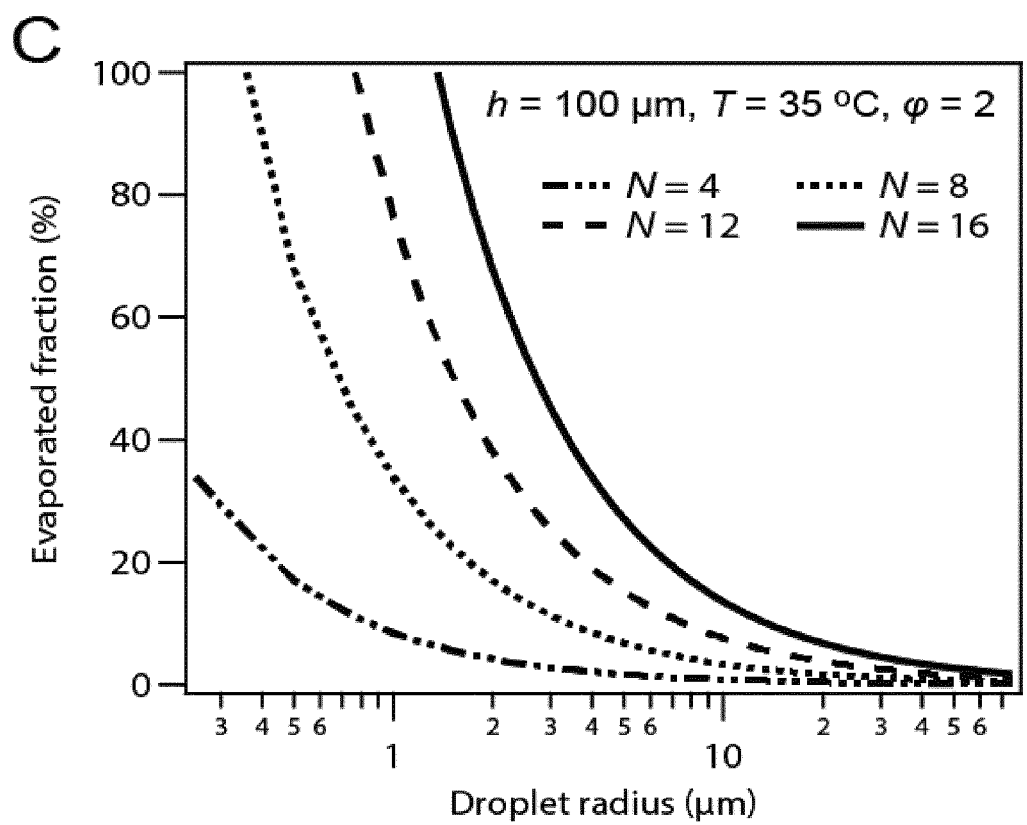
Figure 12:
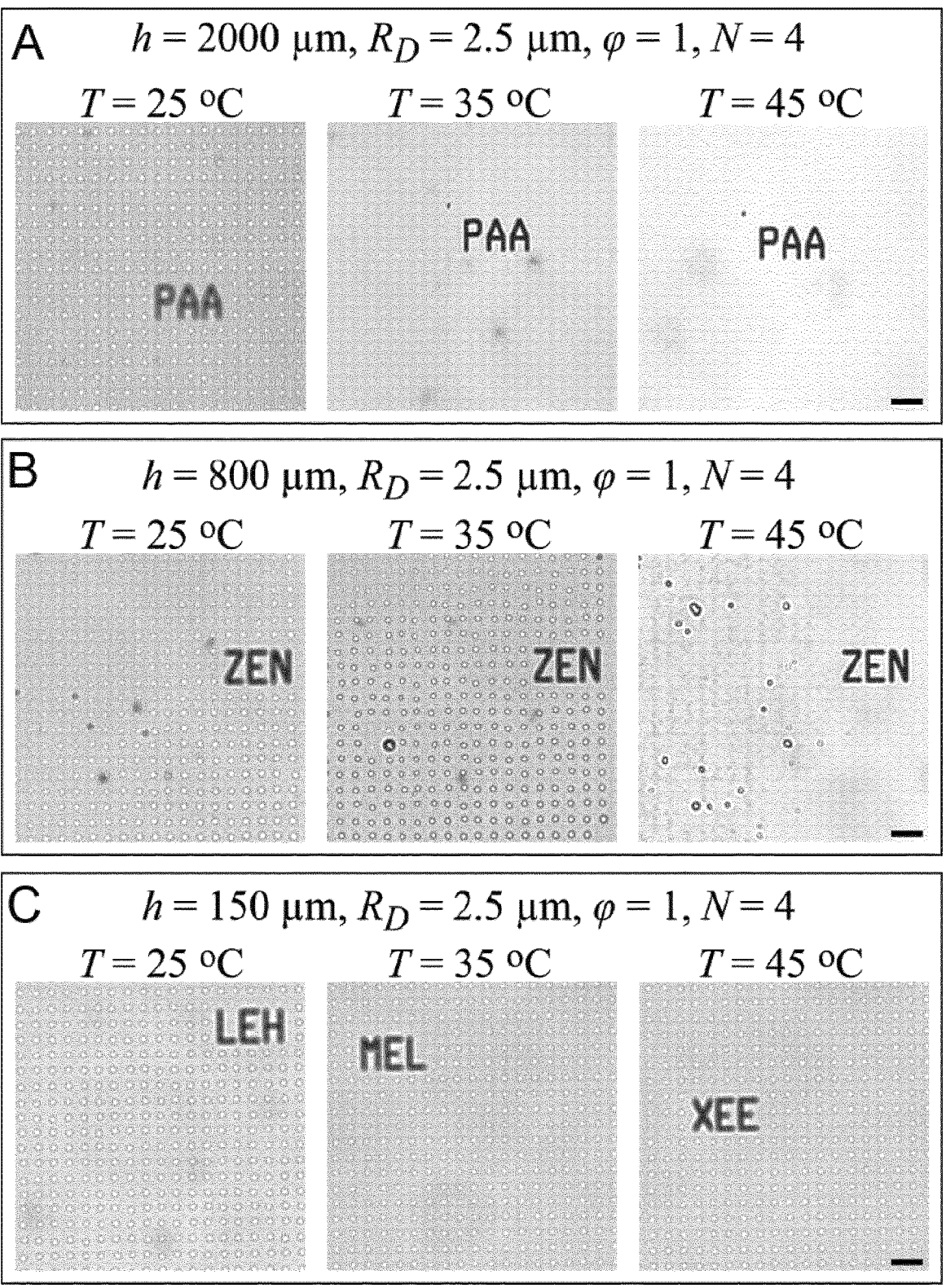
Figure 13:
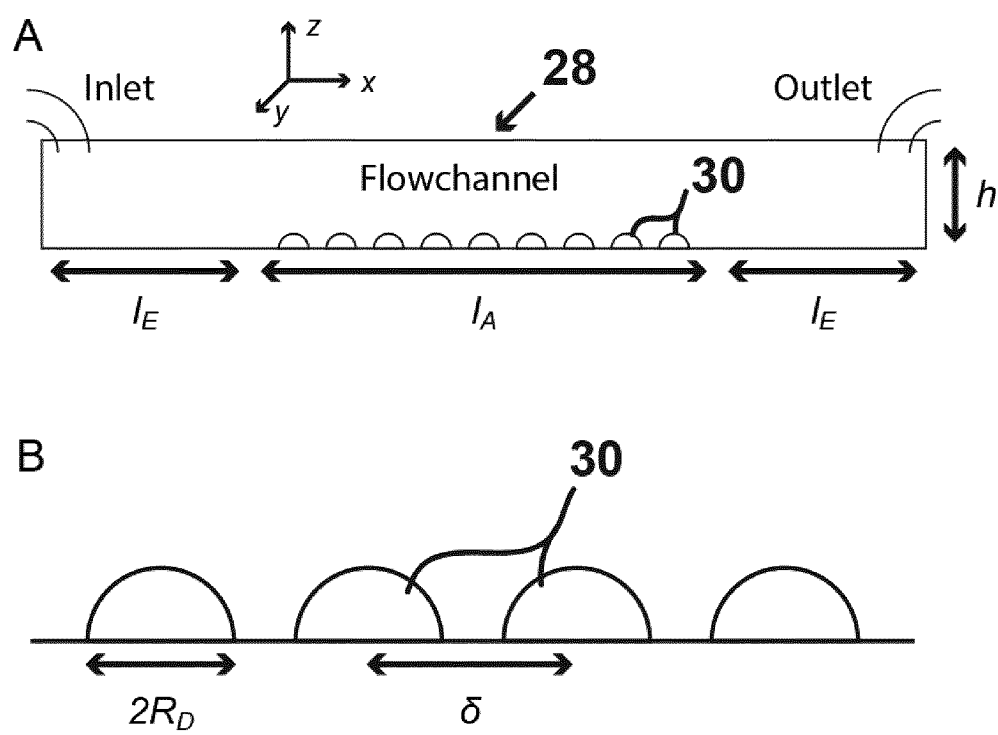
Figure 14:
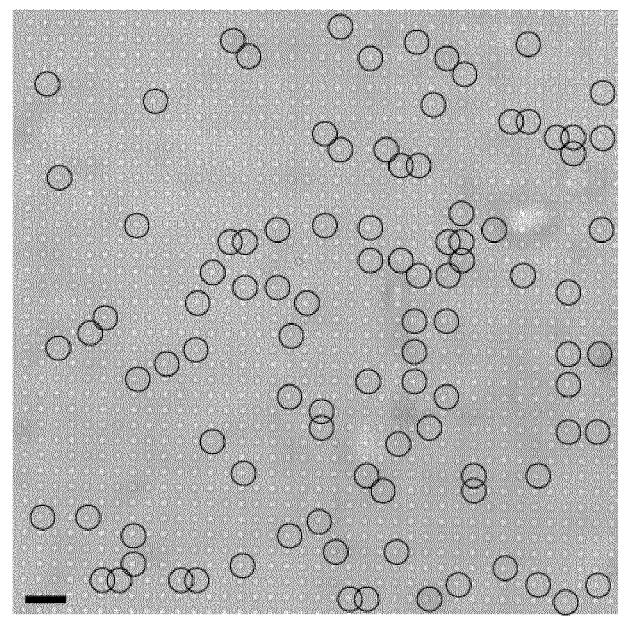
Figure 14:
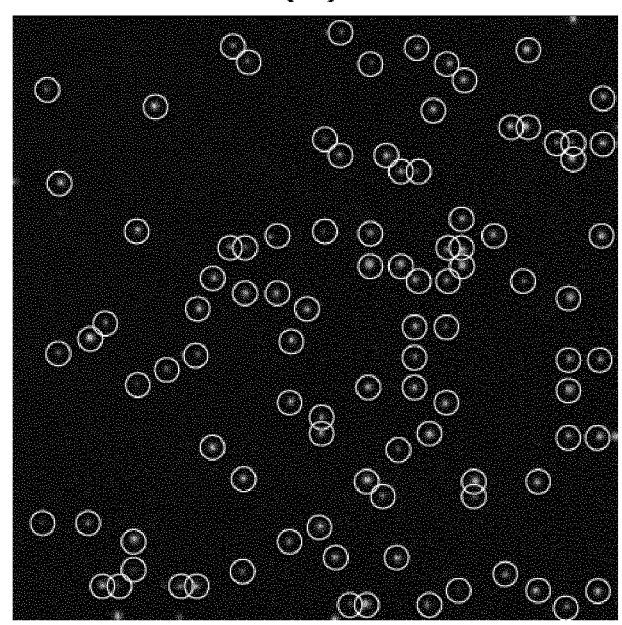
Figure 15:
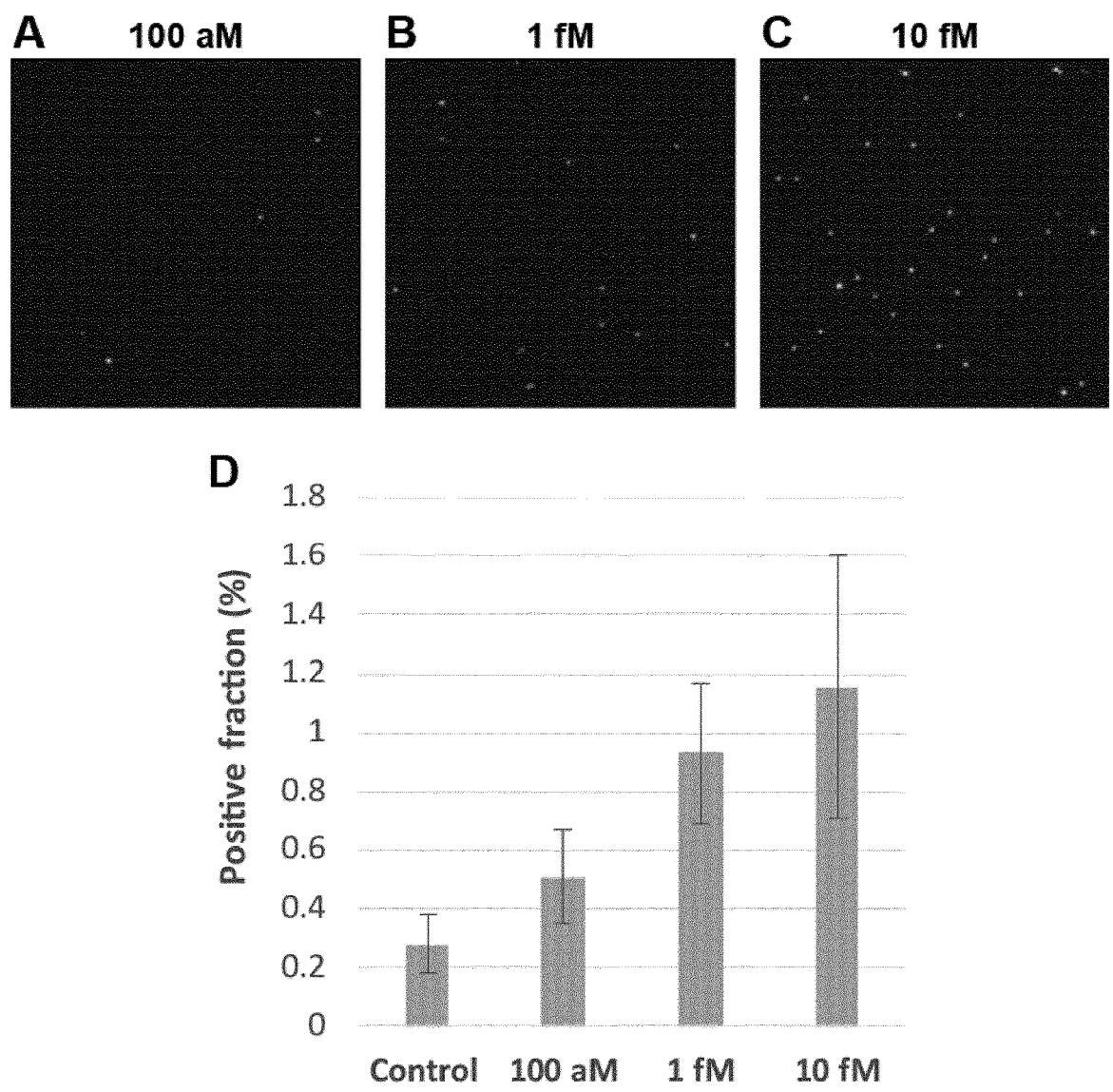
Figure 16:
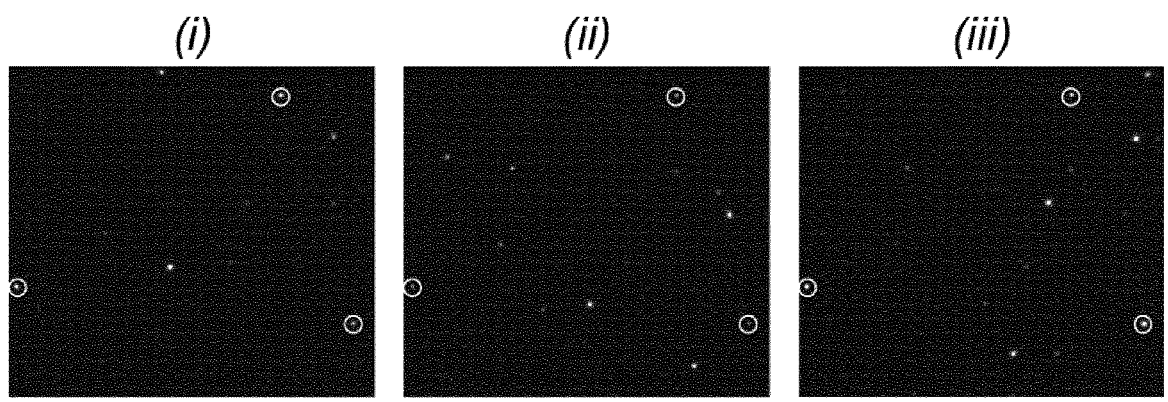

FIG. 8 schematically provides an example of a generic digital counting measurement in which the concentration of analytes from a sample is obtained by analysis of the number of compartments displaying a positive signal;

FIG. 9 provides exemplary sketches of SELMA processes based on planar hydrophilic features. In step (A) analytes from a sample is bound in a single step to capture probes situated on a hydrophilic feature. In step (B1) a capture probe residing in the bulk liquid (capture probe part 2) binds to an analyte from the sample, thus in step (B2) leading to the formation of an analyte/capture probe part 2-complex. Step (B3) is subsequent to B2 and shows the binding of the analyte/capture probe part 2-complex to a capture probe residing on a solid support (capture probe part 1). Capture probes part 1 and 2 recognizes each other, and hence forms a capture probe part 1/capture probe part 2/analyte-complex on the solid support, thus immobilizing the analyte on the hydrophilic feature. In step (C) labelling agents are added to the capture probe/analyte-complex, such as to form a capture probe/analyte/labelling agent-complex. In step (D) the capture probe/analyte-complex is labelled by a first part of a labelling agent (labelling agent part 1). In step (E) the capture probe/analyte/labelling agent part 1-complex is secondary labelled by a second part of the labelling agent (labelling agent part 2). In step (F) a functional capture probe/analyte/labelling agent-complex has been formed. In step (G) a liquid droplet is formed on the surface of the hydrophilic feature. The droplet contains detection agents and is protected from evaporation by a gas phase seal. In step (H) the detection agents are converted to molecular reporters by processing of the labelling agent. The sketches are not drawn to scale;

FIG. 10 provides a sketch of an exemplary flow system. The flow system is composed of a rectangular slab comprising five functional elements. Each element is marked with a number and is enclosed by dashed squares. Element 1 is the liquid outlet connected to a pressure source to provide suction. Element 2 is the flow compartment. Element 3 is the liquid inlet connecting the flow compartment to the liquid loading pad. Element 4 is the liquid loading pad shaped as a receptacle for liquid reagents. Element 5 is the droplet region, which presents a pattern of hydrophilic features surrounded by a hydrophobic substrate. The droplet region is situated on the bottom part of the flow compartment. The sketch is not drawn to scale;

FIG. 11 shows an example of the theoretical relationship between evaporation and flowchannel-/droplet-/array-geometry. (A) Plot of Eqn. 17 for an array with droplet radius of 2.5 µm and scaling factors of N=4 and φ=2, the evaporated fraction will increase as the temperature increases, as well as when the flow channel height increases from 100 µm to 1500 µm. (B) Plot of Eqn. 18 for the maximum height ($h_{MAX}$) as a function of the maximum allowed evaporated fraction ($\theta_{MAX}$) at 35° C. and for various array/droplet geometries. (C) Plot of Eqn. 17 for a flowchannel displaying a height of 100 µm, a scaling factor of φ=2 and held at a temperature of 35° C. The greater spacing between neighboring droplets (greater N-values) leads to higher evaporated fractions, whereas greater droplet sizes decreases the evaporation;

FIG. 12 demonstrates an example of evaporation resistant micro-droplets under a gas phase seal and the droplet stability for various flowchannel geometries and temperatures. Brightfield micrographs showing droplets formed in flow channels exhibiting heights of (A) 2000 µm, (B) 800 µm and (C) 150 µm. The array parameters were identical for A-C, i.e. droplet radius $R_D$=2.5 µm, excess-to-array length ratio φ=1 and array pitch N=4. The three arrays were prepared in an identical manner: An aqueous solution was infused and withdrawn from the flowchannel and the temperature adjusted to 25° C. After an equilibration time of 30 min., micrographs were acquired and the temperature ramped to 35° C. Again micrographs were acquired after 30 min. equilibration. The procedure was repeated for 45° C. On panel A, droplets are clearly distinguishable only at 25° C. At higher temperatures, the droplets evaporate. On panel B, droplets can be distinguished at 25° C. and 35° C., although the droplet diameters appear to have shrunk due to evaporation. At 45° C. the array is largely disrupted due to evaporation and re-condensation of water-vapor, which indicates that the flowchannel/array had not reached thermal equilibrium at the time when the micrographs were acquired. On panel C, droplets are clearly distinguishable at all temperatures and the droplet diameters appear largely unchanged. Scalebars are 20 µm;

FIG. 13 provides an exemplary sketch of parameters defining (A) an exemplary flow channel 28 and (B) an exemplary micro-droplet array 30 embedded in the flow channel. The sketches are not drawn to scale;

FIG. 14 provides a corresponding pair of brightfield (i) and fluorescence (ii) micrographs for a calibration sample containing 1 pM DNA target. Fluorescence signals were identified as described in Example 4 and were marked with white circles. The positions of the fluorescence signals were applied to the brightfield micrograph and are shown as black circles. It is evident that the positions of the fluorescence signals correspond to the position of the liquid droplets. The scale bar is 10 µm;

FIG. 15 provides three representative fluorescence micrographs from samples containing the following concentration of DNA target; (A) 100 aM, (B) 1 fM (1 femtomoles/l or $1\times10^{-15}$ M) and (C) 10 fM. The number of fluorescing droplets were counted for each sample and normalized to the total number of droplets present on the array, such as to provide the percentwise fraction of fluorescing droplets, i.e. the positive fraction. The positive fraction is plotted for samples containing 100 aM DNA target, 1 fM DNA target, 10 fM DNA target as well as a control sample containing no DNA target (D). The values on the bar chart represent average values collected from 5 detection experiments for each sample. The error bars represent the standard deviation of the positive fraction for the 5 identically conducted experiments;

FIG. 16 provides a series of fluorescence micrographs for a sample containing 100 aM target DNA as outlined in Example 5. The first micrograph in the series (i) was acquired after the first detection step, the second micrograph in the series (ii) was acquired on the same position after the second detection step and the third micrograph in the series (iii) was acquired on the same position after the third detection step.

Figure 17:
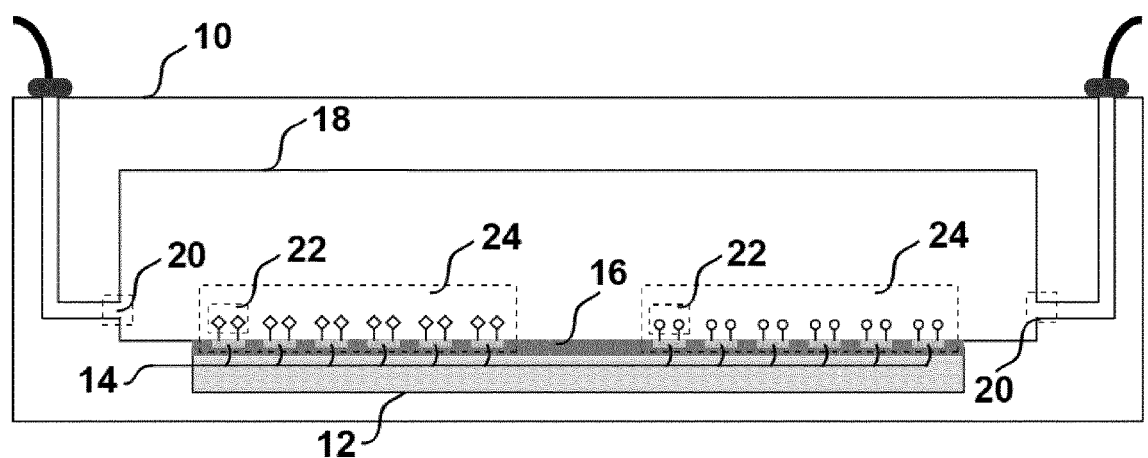

FIG. 17 provides a sketch of a cross-section of an exemplary flow system (10) for digital counting of one or more analytes in a sample comprising a support (12) displaying a pattern of hydrophilic features (14). The pattern is embedded in, placed on or surrounded by a hydrophobic substrate (16) and embedded in a flow compartment (18), which exhibits openings (20). Each hydrophilic feature has capture probes (22) attached to the surface. The support is divided into two regions (24) each region presenting a specific type of capture probe. The sketch is not drawn to scale.

Figure 18:
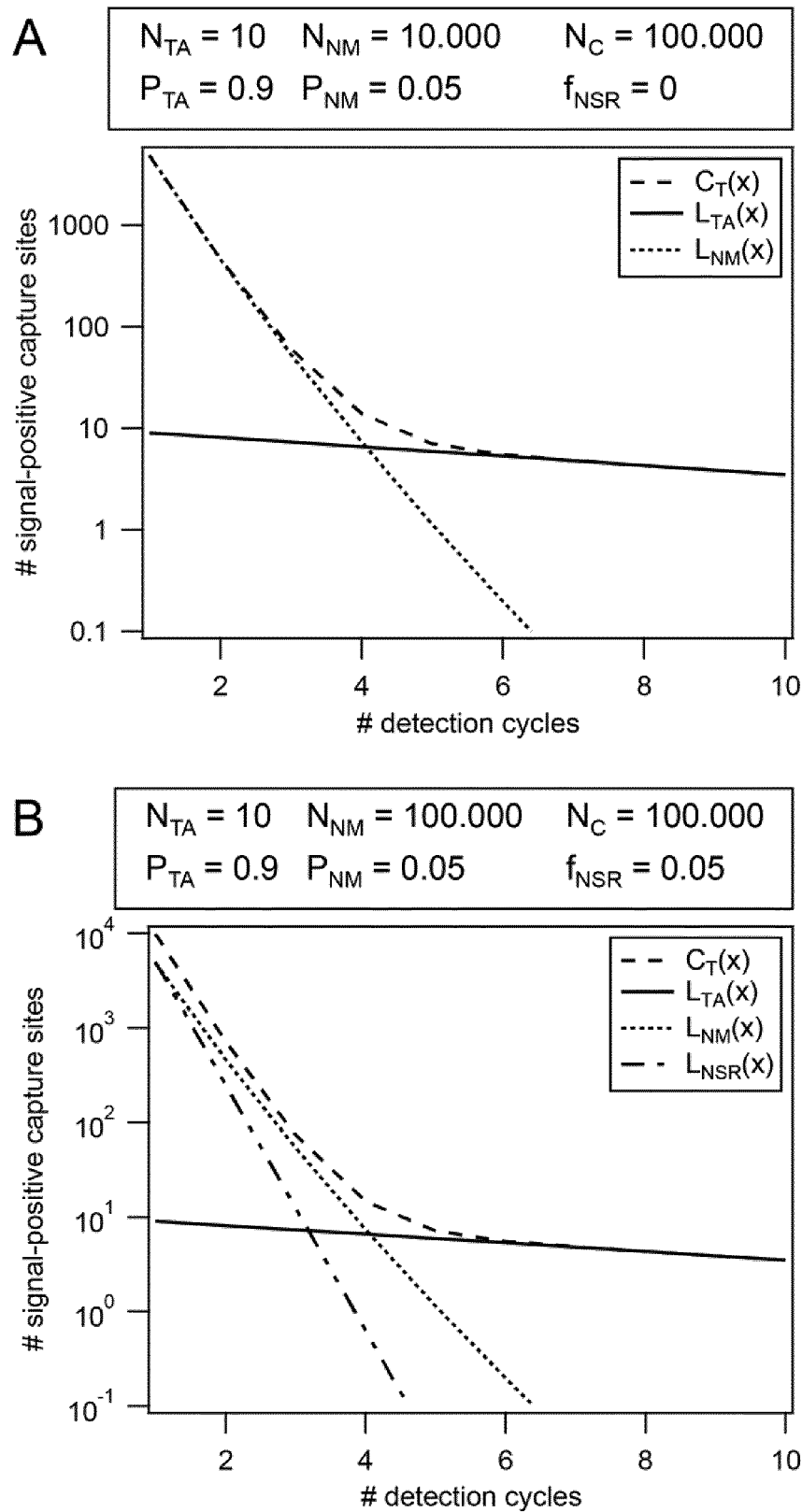
Figure 18:
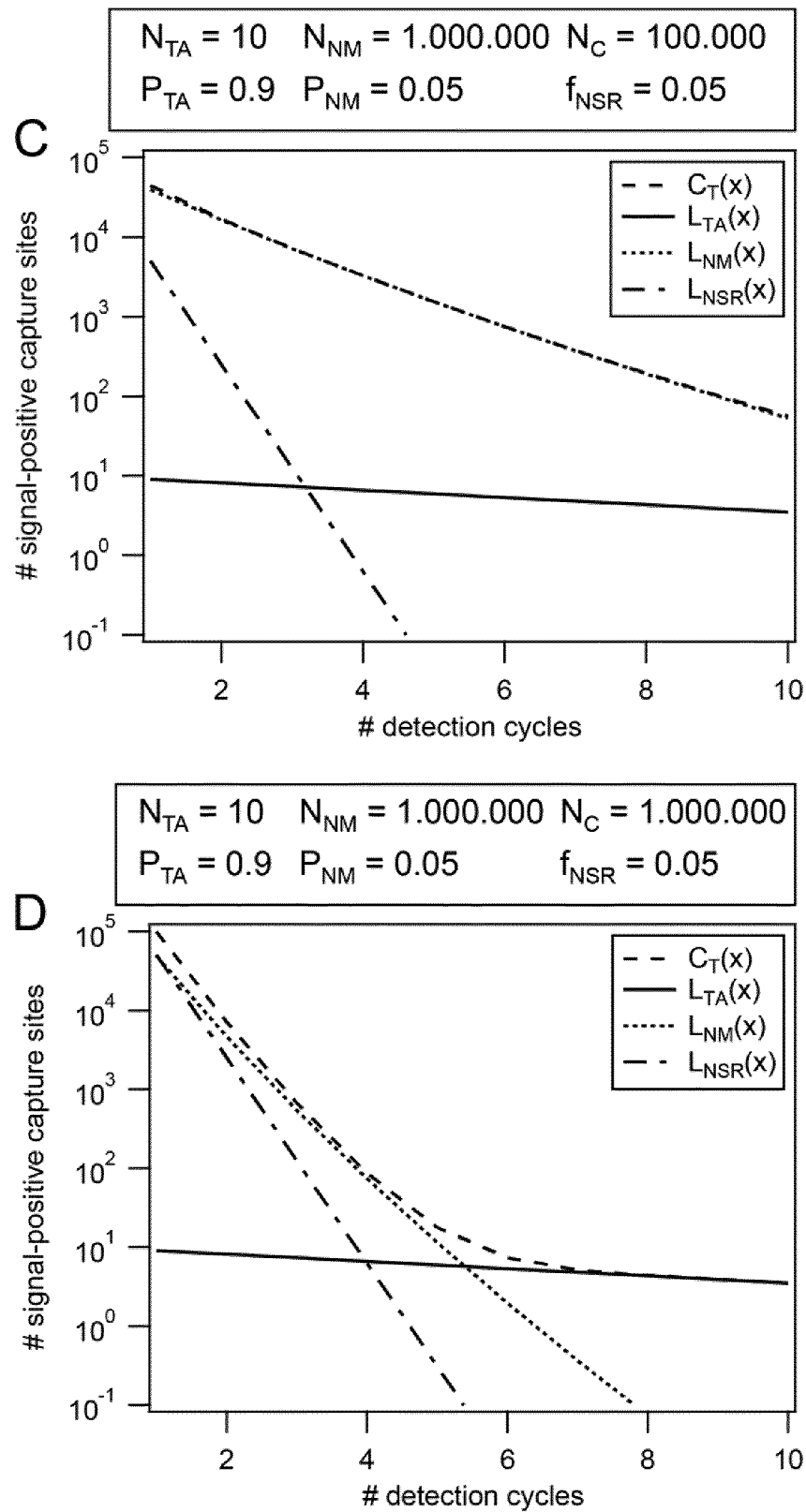

FIG. 18 shows an example of the theoretical relationship between the number of capture sites exhibiting a signal in a single molecule counting analysis as a function of the number of applied detection cycles. The graphs are plotted according to Eqns. 25-28, and applies the following parameters (A) $N_{TA}$=10, $N_{NM}$=10,000, $N_C$=100,000, $P_{TA}$=0.9, $P_{NM}$=0.05 and $f_{NSR}$=0, (B) $N_{TA}$=10, $N_{NM}$=100,000, $N_C$=100,000, $P_{TA}$=0.9, $P_{NM}$=0.05 and $f_{NSR}$=0.05, (C) $N_{TA}$=10, $N_{NM}$=1,000,000, $N_C$=100,000, $P_{TA}$=0.9, $P_{NM}$=0.05 and $f_{NSR}$=0 and (D) $N_{TA}$=10, $N_{NM}$=1,000,000, $N_C$=1,000,000, $P_{TA}$=0.9, $P_{NM}$=0.05 and $f_{NSR}$=0.05. In panels A-D $C_T(x)$, $L_{TA}(x)$, $L_{NM}(x)$ and $L_{NSR}(x)$ represents the total number of signal-positive capture sites, the number of signal-positive capture sites, where the signal originates from (i) target analytes, (ii) non-target molecules and (iii) non-specifically retained labelling agents, respectively, and where x indicates the number of detection cycles.

DETAILED DISCLOSURE

Definitions

In the present context, the term "digital counting", "digital counting analysis", "single molecule digital counting", or "single molecule digital counting analysis" refers to any analysis in which specific components of a sample are partitioned into compartments at a limiting concentration, such that the number of compartments is greater than the number of specific sample components. In this way, a binary/digital value may be assigned to each compartment depending on whether it is empty (value 0) or whether it is loaded (value 1). In this context, loaded refers to a compartment containing at least one of the specific sample components, whereas empty refers to a compartment containing none of the specific sample components. Digital counting takes place when the numbers of loaded and empty compartments are evaluated on the basis of a specific signal originating either from the specific sample component itself or from accessory detection reagents coupled to the presence of the specific sample component.

In the present context, the term "digital counting measurement" refers to a digital counting process as defined above, but further includes any mathematical treatment or calibration of the digital counting result, such as to infer the absolute number of specific sample components present in all compartments. This may include (i) accounting for the fact that loaded compartments may contain either 1, 2, 3, etc. copies of the same sample component, or (ii) accounting for the fact that loaded compartments may be falsely classified as empty and vice versa, due to imperfections in the signal generation process. Examples of digital counting measurements include digital polymerase chain reaction (dPCR), single enzyme-linked immunosorbent assay (sELISA) or digital single-enzyme linked immunosorbent assay (dELISA). A sketch of a digital counting measurement process is outlined in FIG. 8.

In the present context, the term "SELMA" is used as an abbreviation for single-enzyme linked molecular analysis and refers to a specific kind of a digital counting measurement. In SELMA, the digital counting measurement takes place in a flow system, in which droplet compartments are organized in a pattern, and specific sample components become immobilized/captured inside the compartments. In this way, sample components may be subjected to several reaction steps without being lost, each reaction step comprised by immersion and withdrawal of solutions or reagents from the flow system. A sketch of exemplary SELMA-processes is provided in FIG. 9.

In the present context "hydrophilic feature" refers to a structure having a first set of material properties surrounded or supported by a solid substrate having another set of material properties. The material properties of the structure and the solid substrate should be adjusted, such that the structure is more wettable than the solid substrate. In other words, the material of which the structure is composed should exhibit a smaller contact angle with water than the solid substrate does. The structure may be defined by chemical and/or physical means. A non-limiting set of possible structures include (i) a closed planar region composed of a more hydrophilic material than the surrounding substrate and (ii) a depression, a protrusion or a combination thereof formed in the surrounding substrate in which one or more of the sides are composed of a more hydrophilic material than the surrounding substrate. Sketches of exemplary hydrophilic features are provided in FIG. 5. In the context of SELMA, hydrophilic features may be manipulated to present suitable reaction compartments for digital counting measurements, e.g. by providing distinct chemical functionality for analyte capture and by providing a pattern of liquid droplets for signal generation and detection.

In the present context, the term "planar hydrophilic feature" refers to a design in which the hydrophobic substrate is planar and the hydrophilic feature embedded in the hydrophobic substrate is planar. The ideal case of planarity is sketched in FIG. 5, however for practical applications planarity would have to be defined in terms of surface roughness. For example, because the hydrophobic substrate and hydrophilic features may be formed from different materials, there might be minute differences in the height between the hydrophobic and the hydrophilic regions. In one embodiment, a suitable criterion for a hydrophilic feature to be considered planar could be that the height difference (alternatively the surface roughness) between the hydrophobic and hydrophilic regions ($\Delta h$) should be negligible compared to the characteristic feature size. In the case of a circular hydrophilic feature having a radius $R_D$, the criterion could be $R_D \gg \Delta h$. In one embodiment, features exhibiting $\Delta h$-values less than 20 nm is considered to be planar.

In the present context, the term "contact angle" refers to the characteristic angle measured at a liquid/vapor/solid interface. In the context where a liquid droplet is deposited on a solid surface in a gas phase, the contact angle is measured through the liquid at a point on the line, where the liquid/vapor interface meets the solid surface. The angle is measured between the solid surface and the tangent of the liquid interface, as defined in the work of W. C. Bigelow, D. L. Pickett and W. A. J. Zisman in "Oleophobic monolayers I: Films adsorbed from solution in non-polar liquids" published in Journal of Colloid Science, vol. 1, pp. 513-538 (1946) (DOI: 10.1016/0095-8522(46)90059-1). A sketch of an exemplary contact angle is provided in FIG. 6.

In the present context, the term "RH" means "the relative vapor saturation of the gas component of the liquid", which is a generalization of the term "relative humidity". Relative humidity is defined as the ratio between the partial vapor pressure of water ($P_W$) to the saturation pressure of water in atmospheric air ($P_{SAT}$), i.e. RH=$P_W/P_{SAT}$. The saturation pressure is here defined as the partial pressure exerted by water vapor in thermal equilibrium with liquid water. The RH-value may be generalized to include other liquids than water. In this case, RH still equals $P_W/P_{SAT}$, but here $P_W$ is to be understood as the partial pressure exerted by the gas component of a given liquid, and $P_{SAT}$ is to be understood as the partial pressure exerted by the gas component in thermal equilibrium with the given liquid. The partial pressures refer to the case, where the gas phase is constituted by several gas species. RH may thus be thought of as an indicator of the vapor saturation level of the corresponding gas phase. That is for RH=0, the gas phase does not contain any gas component of the liquid, whereas for RH=1, the gas phase has taken up the maximum possible content of the gas component of the liquid.

In the present context, the term "RHI" means the "the initial relative vapor saturation of the gas component of the liquid". When the term "the initial relative vapor saturation of the gas component of the liquid" is applied, then it indicates a situation, where change is about to take place, and thus where thermal equilibrium has not been established yet. For example, if a liquid 1, having a characteristic saturation pressure of $P_{SAT}$, is placed in a closed environment containing a gas phase, where the partial pressure of the gas component of liquid 1 is $P_1$, then if $P_1 < P_{SAT}$ liquid will evaporate. The initial relative vapor saturation of the gas component of the liquid is thus $RHI = P_1/P_{SAT}$, because it is calculated prior to any change has taken place. However, once evaporation of liquid 1 starts, the RH-value will gradually increase from the RHI-value until either (i) RH=1 thus saturating the gas phase or (ii) all the liquid has evaporated.

In the present context, the term "maximum droplet volume" refers to the greatest liquid volume a single hydrophilic feature may support if prepared under optimal conditions. In the context of evaporation of liquid from a droplet, then the volume fraction of evaporated liquid is calculated with respect to the maximum droplet volume. A sketch of an exemplary maximum droplet volume for a planar circular hydrophilic feature is provided in FIG. 6.

In the present context, the term "aggregate maximum droplet volume" refers to the sum of volumes obtained by adding together the maximum droplet volumes of a pattern containing a plurality of droplets. In the context of evaporation of liquid from the pattern, then the volume fraction of evaporated liquid is calculated with respect to the aggregate maximum droplet volume.

In the present context, the term "sample" refers to a collection of biological or chemical material, which may or may not have been subjected to laboratory processing. The sample may assume liquid or solid form and may contain specific components, which serve as input for digital counting.

In the present context "a sample potentially containing at least one analyte" refers to a biological specimen, which is either suspected of containing one or more specific analyte type(s) or suspected of containing one or more specific analyte type(s) at one or more specific concentration(s) in the sample.

In the present context, the term "analyte" refers to a specific sample component, which may become utilized in a digital counting measurement. An analyte is of biological or molecular nature and is to be (i) separated from the remaining sample material and/or (ii) distinctly manipulated during a digital counting process.

In the present context, the term "analyte type" refers to a specific class or species of analytes. For example, could two different analyte types be oligonucleotides and proteins, respectively. Another example of two different analyte types could be proteins and cells, but analyte type may also refer to for example two different proteins, two different oligonucleotides or two different cells.

In the present context, the term "capture probe" is a chemical or biochemical agent of molecular nature able to recognize and bind to a specific region of an analyte, such as to retain and/or confine the analyte to a reaction compartment.

In the present context, the term "labelling agent" is a chemical or biochemical agent of molecular nature able to recognize and bind to a specific region of an analyte. The binding region of the labelling agent is different from the binding region of the capture probe, such that during a digital counting measurement a capture probe/analyte/labelling agent-complex may be established. Furthermore, apart from one or more analyte-binding modalities, a labelling agent includes one or more detection-modalities. The term labelling agent may furthermore refer to one or more agents, which when combined together provide an analyte-binding modality and a detection modality.

In the present context, the term "detection modality" refers to a biochemical, chemical, biological or physical moiety able to mediate generation of a signal detectable by a detector. The signal could be optical, electrical or magnetic in nature. Furthermore, the detection modality may rely on a detection agent in order to achieve signal generation.

In the present context, the term "detection agent" refers to a compound, usually of molecular nature, which may change chemical or physical state when contacted by a compatible detection modality. The change of state of the detection agent may be recorded and translated into a signal by a suitable detector. Furthermore, a detection agent which has undergone a change of state may be referred to as a reporter molecule or molecular reporter.

In the present context, the term "detectable concentration" or "minimum detectable concentration" refers to the lowest concentration of a molecular reporter confined to a reaction compartment, which may be detectable by a suitable detector. In order for a concentration to become detectable, the signal resulting from the molecular reporters should exceed that of the noise-level of the detector. In general, a higher concentration of a molecular reporter tends to produce a corresponding higher signal as recorded by the detector.

In the present context, the term "discrete capture sites" refers to a specific region on a solid phase, which is able to capture or attach to analytes. The capture site region may be functionalized with capture probes specific to the analyte type. The solid phase may be a continuous surface or substrate displaying a plurality of discrete capture sites, such that regions of individual capture sites do not intersect. Furthermore, the solid phase may also be comprised by one or more colloidal beads, where the surface of the beads has been functionalized with capture probes. In this case, a single bead would constitute a single capture site, and a collection of beads, for example suspended in a liquid, would constitute a plurality of discrete capture sites.

In the present context, the term "liquid compartments" refers to volumes of liquid—typically in the nano-to-attoliter range—in which the individual liquid compartment is fluidically insulated from the other liquid compartments present.

In the present context, the term "fluidically insulated" refers to liquid compartments prepared in such a way that the liquid content from one individual compartment cannot readily leak into any other compartment present. Liquid compartments may be rendered fluidically insulated by e.g. partitioning a bulk liquid (i) into wells/cavities/capillaries, (ii) into smaller liquid volumes on a hydrophobic substrate containing hydrophilic features, such that each liquid volume is held in place by surface tension or (iii) into emulsion droplets.

In the present context, the term "compartmentalize" refers to the process of partitioning a bulk liquid and its contents into smaller volumes such that each volume forms a liquid compartment.

In the present context, the term "triggering of signals" refers to the process of inducing a labelling agent confined to a liquid compartment to produce a detectable signal. A detectable signal may be induced by contacting the detection modality of the labelling agent with a suitable detection agent. The detection modality may then convert the detection agent to a molecular reporter, which due to the fluidic insulation of the liquid compartment accumulates within the compartment until a minimum detectable concentration of the molecular reporter is established within the compartment.

In the present context, the term "deactivation of signals" refers to the process of permanently disabling the ability of the labelling agent to trigger a signal within the liquid compartment in which it is confined. One way of disabling a labelling agent from triggering a signal within the liquid compartment could be to remove the labelling agent from the compartment. Another way of disabling a labelling agent from triggering a signal within the liquid compartment could be to disable, e.g. by chemical, biochemical or physical means, the detection modality of the labelling agent, such that it would not be able to convert detection agents to molecular reporters.

In the present context, the term "non-specifically bound" refers to for example labelling agents attached directly to an empty capture site and hence not attached directly to a captured analyte. A labelling agent may also be considered to be non-specifically bound if it instead of the captured analyte is attached to a captured non-target molecule. A non-specifically bound labelling agent may produce an erroneous or false-positive signal, because the liquid compartment hosting the non-specifically bound labelling agent did not capture an analyte, but is still capable of producing a detectable signal.

In the present context, the term "counting error" or "digital counting error" refers to for example false-positive signals originating from non-specifically bound labelling agents. Liquid compartments hosting non-specifically bound labelling agents, but hosting no captured analytes, are considered as noise in a digital counting analysis, because they do not represent a true signal from the analyte. For example, a labelling agent may be considered non-specifically bound (i) if it has been physisorbed or chemisorbed to the capture site without forming an analyte/labelling agent-complex or (ii) if a complex has been formed between the labelling agent and another non-target compound/molecule present on the capture site.

In the present context, the term "false-positive detection cycle" for example refers to a detection cycle, in which the labelling or re-labelling step is carried out without contacting the plurality of capture sites with labelling agents. This allows false-positive signals—in the form of non-specifically bound labelling agents—to be detected. For example, if in the preceding detection cycle a signal deactivation step had been carried out, such that labelling agents bound to the captured analyte had been specifically removed, then non-specifically bound labelling agents would remain on the capture sites. Because no new labelling agents are supplied to the plurality of capture sites in the labelling or re-labelling step, then the signal triggering step may only give rise to detectable signals from liquid compartments hosting non-specifically bound labelling agents and thus enabling detection of liquid compartments contributing false-positive signals. Another example of a false-positive detection cycle may allow identification and quantification of the number of non-target compounds/molecules in the sample by applying a detection cycle, in which the labelling or re-labelling step is carried out with a labelling agent specific to the non-target compound/molecule.

In the present context, the term "intermittent signal pattern" refers to a liquid compartment, which has been subjected to two or more detection cycles, and where the liquid compartment did not produce signals in all the detection cycles. For example, if four detection cycles were executed, and a liquid compartment only produced a signal in the second and the fourth detection cycle, then it is considered to give rise to an intermittent signal pattern. On the other hand, if another liquid compartment was subjected to four detection cycles, and it produced signals in all cycles, then it is not considered to give rise to an intermittent signal pattern, but is instead considered to repeatedly produce a signal.

In the present context, the term "flow compartment" refers to a compartment, which may be channel-shaped and which serves to guide the flow of a liquid, such that the liquid will be brought in contact with the plurality of discrete capture sites. A flow compartment may have an inlet, where liquid may enter the flow compartment, and an outlet, where liquid may leave the flow compartment. In between the inlet and the outlet, the plurality of discrete capture sites may be placed.

In the present context, the term "flow system" refers to an assembly of one or more flow compartment(s), which further may include one or more reservoir(s) to contain a liquid, one or more valve(s) or switching mechanism(s) to dispense liquid from the reservoir(s) into the flow compartment(s) or to grant or prevent liquid access to the flow compartment(s). Furthermore, a flow system may also contain or be connected to a liquid actuation unit to enable the liquid flow into the flow compartment(s).

In the present context, the term "gas phase seal" refers to the result of the process of establishing a gas phase seal, where the purpose of the gas phase seal is to prevent or reduce evaporation from a liquid compartment. In an embodiment, the process is initiated by placing a plurality of nano-to-attoliter liquid compartments in a flow system, where the dimensions of the flow system and the spatial configuration of the plurality of liquid compartments have been configured such that only a small fraction of the liquid volume of the individual liquid compartment may evaporate before the gas phase within the flow compartment of the flow system has been saturated with the gas component of the liquid. In this way, the evaporated liquid establishes a gas phase seal, which may ensure that nano-to-attoliter liquid compartments are kept stable in the flow compartment for extended periods of time without evaporating.

In the present context, the term "immobilization" refers to the process of fixing a mobile component from a sample, such as an analyte, to a solid phase such as to prevent it from diffusing back into the sample once fixed.

The invention disclosed herein provides methods for reducing the counting error such as false-positive detections and/or reducing/removing noise in single-molecule measurements and thus allows for improved quantification, improved sensitivity and improved specificity.

In a first embodiment disclosed herein, is a method for digital counting analysis of a sample potentially containing at least one analyte, wherein the sample has been contacted with a solid phase having a plurality of discrete capture sites, each site being capable of capturing the at least one analyte, which method comprises at least two detection cycles, where each detection cycle comprises the steps of
- a) triggering a signal from captured and labelled analyte(s),
- b) recordation of the number and positions of capture sites exhibiting a signal from the captured and labelled analyte(s),
- c) and before a further detection cycle is performed, deactivation of signal(s).

In an embodiment disclosed herein, the capture sites are enclosed by a liquid compartment during the signal triggering process.

In the first embodiment, the digital counting analysis may be particularly suited for being carried out in a format, where the capture sites are provided as cavities, depressions or through-holes in a substrate, and where the individual steps in the detection cycle may be conducted either by aspiration and dispensing of reagent solutions into the plurality of capture sites or by complete immersion and withdrawal of the substrate from a reagent solution.

The discrete capture sites may be provided by chemical patterning of a solid substrate, for example the surface of a solid-state chip, or by topographical patterning of a substrate, for example the wells in a microtiter plate. The features of the chemical or topographical pattern may then exhibit the ability of binding to analytes from the sample by derivatizing the surface with capture probes. The discrete capture sites may also be provided as a collection or suspension of colloid beads. In that case, each bead constitutes a single capture site provided the surface of the bead has been derivatized with capture probes.

In a further embodiment, the digital counting analysis may also be particularly suited for being carried out in a flow compartment as described herein where hydrophilic features are configured to support a plurality of liquid nano-to-attoliter droplets, and the flow compartment further is configured to support a gas phase seal reducing evaporation of each nano-to-attoliter droplet.

In a second embodiment disclosed herein, is a method for digital counting analysis of a sample potentially containing at least one analyte, wherein the sample has been contacted with a solid phase having a plurality of discrete capture sites, each site being capable of capturing the at least one analyte, which method comprises at least two detection cycles, where each detection cycle comprises the steps of labelling the at least one analyte by adding a labelling agent and compartmentalize the at least one captured and labelled analyte to produce liquid compartments containing at least one analyte followed by steps a)-c):
- a) triggering a signal from the captured and labelled analyte(s),
- b) recordation of the number and positions of capture sites exhibiting a signal from the captured and labelled analyte(s),
- c) and before a further detection cycle is performed, deactivation of signal(s)

In the second embodiment, the digital counting analysis may be particularly suited for being carried out in a format, where all steps in the detection cycle and all steps leading to capture may take place on or adjacent to a solid substrate containing a plurality of capture sites. The substrate could for example be hydrophobic with a pattern of hydrophilic capture sites, such that liquid compartments may form on the capture sites upon immersion and withdrawal of reagent solution from the substrate.

In a third embodiment disclosed herein, is a method for digital counting analysis of a sample potentially containing at least one analyte, wherein the sample has been contacted with a solid phase having a plurality of discrete capture sites, each site being capable of capturing the at least one analyte, wherein the at least one analyte is labelled by adding a labelling agent in a labelling step prior to or during capture of the at least one analyte on the solid phase, which method comprises at least two detection cycles, wherein the at least one captured and labelled analyte is compartmentalized to produce liquid compartments containing at least one analyte followed by steps a)-c):
- a) triggering a signal from the captured and labelled analyte(s),
- b) recordation of the number and positions of capture sites exhibiting a signal from the captured and labelled analyte(s),
- c) and before a further detection cycle is performed, deactivation of signal(s), wherein step c) before a further detection cycle is performed is followed by a re-labelling step, wherein the at least one captured analyte is labelled by adding a labelling agent.

In the third embodiment, the digital counting analysis may be particularly suited for being carried out in a format, where the initial capture and labelling takes place in bulk solution, and where the detection cycle and re-labelling involves compartmentalization of analytes and/or labelling agents. For example, the initial capture and labelling may be carried out by using a collection of colloid beads as the plurality of capture sites, and suspend the collection of colloid beads in a solution containing the sample and labelling agents, such that a bead may harbor a captured and labelled analyte. Next, the collection of beads may be compartmentalized for example by being encapsulated in emulsion droplets, or by being dispersed into cavities, depressions or through-holes on a solid substrate. Another example could be where a sample containing analytes is mixed with labelling agents and introduced on a solid substrate having a plurality of discrete capture sites, such that captured and labelled analytes may be formed in a single step.

In an embodiment, the method comprises a step (capture step) to enable capture of the target analyte by a capture element, such that the target analyte becomes immobilized in one of the first steps of the analysis. The capture element is not necessarily specific only to the target, but may also exhibit a certain degree of cross-reactivity to non-target compounds.

The immobilization may take place in bulk solution, but may also take place in a liquid compartment, where only a single or few target analytes are confined within the liquid compartment. In an embodiment, the number of discrete capture sites is greater than the number of analytes in the sample, such that each liquid compartment is either empty (i.e. no captured analytes) or loaded (i.e. one or more captured analytes). For samples with unknown amounts of analyte, this distribution can be ensured by carrying out the method disclosed herein on increasingly diluted samples. The occupancy of captured analytes per liquid compartment is random and may be approximated by the Poisson distribution.

Capture elements may for example be constituted by antibodies, antibody fragments or aptamers, which are capable of binding to a great variety of compounds including proteins and polypeptides. Capture elements may also be single or double-stranded oligonucleotides or synthetic variants thereof, which may capture other oligonucleotides via sequence complementarity and/or strand invasion. Furthermore, capture elements may also be chemical species reactive towards an entire class of molecules, e.g. proteins, amino acids, oligonucleotides, etc., such that the analyte becomes covalently attached to the capture site.

Furthermore, in an embodiment the method comprises another step (labelling step) to achieve labelling of target analytes by one or more labelling agents, such that a complex is formed between the captured target analyte and the one or more labelling agents. The labelling agent may interact specifically with the target analyte, but may also interact to a lesser extent with non-target compounds. The labelling reaction may take place in bulk solution, but may also take place in a liquid compartment, where only a single or few target analytes are immobilized within the liquid compartment.

Labelling agents may for example be constituted by antibodies, antibody fragments or aptamers, but may also be single or double-stranded oligonucleotides or synthetic variants thereof. Labelling agents may comprise a region for binding to the analyte and another region for providing or facilitating a signal. One type of labelling agent could be constituted by a binding region linked to an enzyme or any other (bio)chemical catalyst, where the enzyme or catalyst may facilitate signal generation.

Labelling reactions proceeding in bulk may take place by, e.g. immersing a solid substrate containing the plurality of capture sites into a solution containing labelling agents or by suspending a collection of colloid beads, each bead constituting a single capture site, in a solution of labelling agents. Labelling reactions proceeding inside liquid compartments may take place by forming a plurality of liquid compartments, where a single liquid compartment occupies a single capture element and where the liquid of the liquid compartment is a solution of labelling agents. This may be achieved by (i) dispensing a solution of labelling agents into the wells of a microtiter plate, where the wells constitute the capture site, (ii) preparing water-in-oil emulsion droplets encapsulating colloid beads, where a single bead is a single capture site, and where the bead is co-encapsulated with labelling agents or (iii) by immersing a solid hydrophobic substrate containing a plurality of discrete hydrophilic capture sites in an aqueous solution of labelling agents followed by withdrawal of the substrate from the solution, such that liquid droplets form on/in the hydrophilic capture sites.

Even further, the method in an embodiment comprises yet another step (detection step) to produce liquid compartments hosting single or few immobilized and labelled target analytes and to trigger the one or more labelling agents to produce a detectable signal. However, since both the capture elements and the labelling agents may exhibit an affinity towards non-target compounds, then compartments (i) hosting complexes of captured and labelled non-target compounds and (ii) non-specifically bound labelling agents may also be triggered to produce detectable signals.

Even further, the method in an embodiment comprises yet another step (recording step) to record the number and spatial position of liquid compartments exhibiting a detectable signal.

Even further, the method in an embodiment comprises yet another step (deactivation step) to remove the one or more labelling agents from the captured and labelled target analytes as well as from the captured and labelled non-target compounds. In addition, the method comprises deactivating the ability to produce signals of all labelling agents, which previously produced a signal.

Even further, the method in an embodiment comprises repeating one or more of the steps one or more times. The second step may apply either the same labelling agents as in the previous step, but may also apply another type of labelling agents exhibiting a different specificity.

In an embodiment, the method is concluded by comparing the spatial positions of signal-positive liquid compartments between each repetition of the recording step. In this way, target analytes can be distinguished from non-target compounds and non-specifically bound labelling agents, because the labelling agents have been selected to preferably label target analytes. Hence, liquid compartments hosting target analytes will be more prone to consistently and repetitively produce a signal, whereas liquid compartments hosting non-target compounds and non-specifically bound labelling agents will be less likely to repeat a signal.

In an embodiment, the sample and the solid phase having a plurality of discrete capture sites are compartmentalized prior to or during capturing of the at least one analyte.

Compartmentalization prior to or during the capturing of analytes on the capture sites may for example be achieved by (i) dispensing a solution containing the analytes into the wells of a microtiter plate, where the single well is the capture site, (ii) preparing water-in-oil emulsion droplets, where each droplet encapsulates a solution containing the analytes as well as a colloid bead, where the bead is the capture site or (iii) immersing a solid hydrophobic substrate containing a plurality of discrete hydrophilic capture sites in an aqueous solution containing the analytes followed by withdrawal of the substrate from the solution, such that liquid droplets containing analytes form on/in the hydrophilic capture sites.

In an embodiment, the captured analyte(s) and labelling agent are compartmentalized prior to or during labelling of the at least one analyte.

Compartmentalization prior to or during the labelling of captured analytes may for example be achieved by (i) dispensing a solution containing the labelling agents into the wells of a microtiter plate, where the single well is the capture site, and where some of the wells contain a captured analyte, (ii) preparing water-in-oil emulsion droplets, where each droplet encapsulates a colloid bead, where the bead is the capture site, and where some of the emulsion droplets contain a colloid bead having captured an analyte, and where the beads are co-encapsulated with the labelling agents or (iii) immersing a solid hydrophobic substrate containing a plurality of discrete hydrophilic capture sites in an aqueous solution of labelling agents followed by withdrawal of the substrate from the solution, such that liquid droplets containing labelling agents form on/in the hydrophilic capture sites, and where some of the capture sites contain a captured analyte.

In an embodiment, the captured and labelled analyte(s) is compartmentalized to produce liquid compartments containing at least one analyte.

The captured and labelled analytes may be compartmentalized to produce liquid compartments for example by (i) immersing and withdrawing a plurality of hydrophilic capture sites on a hydrophobic substrate, where some of the capture sites contain captured and labelled analytes, in a liquid, such that liquid compartments may form on the surface of the hydrophilic captures sites, (ii) producing water-in-oil emulsion droplets encapsulating captured and labelled analytes or (iii) dispensing captured and labelled analytes into wells on a substrate.

In an embodiment, the analyte(s) is labelled by adding a labelling agent in a labelling step in each detection cycle before step a).

In an embodiment, the captured analyte(s) is labelled by adding a labelling agent in a labelling step prior to or during capturing of the analyte(s) on the solid phase, and wherein step c) before a further detection cycle is performed is followed by a re-labelling step, wherein the captured analyte(s) is labelled by adding the labelling agent.

In some embodiments, labelling of the analytes may be carried out prior to or simultaneously with the capturing of the analytes. For example, capture sites in the form of colloid beads may be mixed with a solution containing labelling agents and analytes, such that either (i) analytes are captured and then labelled or (ii) analytes are labelled and then captured. Another example could be to infuse a solution containing labelling agents and analytes into a solid substrate hosting a plurality of discrete capture sites, such that labelling and capture may take place simultaneously.

In an embodiment disclosed herein, at most 99%, such as at most 95%, such as at most 90%, such as at most 85%, such as at most 80%, such as at most 75%, such as at most 70%, such as at most 65% of the liquid compartments contain captured and labelled analyte.

For quantitative digital counting analysis, it is preferred that not all capture sites contain a captured and labelled analyte, since this could lead to saturation of all capture sites, thus preventing precise counting of all analytes. In order to achieve precise counting, a small fraction of capture sites should be empty, i.e. not contain a captured and labelled analyte. To arrive at an optimum distribution of analyte occupied and empty capture sites, the relevant sample can be provided in several dilutions whereby the counting can be performed on the diluted sample that provides an acceptable or optimal distribution. By counting the number of empty capture sites and comparing it to the number of occupied capture sites, it is possible to estimate the total number of analytes on the capture sites by using statistical analysis, e.g. Poisson statistics.

In an embodiment disclosed herein, the sample contains or potentially contains a target analyte and a non-target compound, where the target analyte is captured by the capture site with capture efficiency $C_1$, where the non-target compound is captured by the capture site with capture efficiency $C_2$ and $C_1 \geq C_2$, where the target analyte is labelled by a first labelling agent with labelling efficiency $L_1$, where the non-target compound is labelled by the first labelling agent with labelling efficiency $L_2$ and $L_1 \geq L_2$, where the number of detection cycles $N_C$ is adjusted such that the ratio $\alpha = C_1 N_1^{N_C} / C_2 N_2^{N_C}$ is between 1-10, preferably between 10-100, preferably between 100-1000, preferably between 1,000-10,000, preferably between 10,000-100,000, preferably greater than 100,000, and where each detection cycle applies the first labelling agent in the labelling step.

In an embodiment disclosed herein, the method includes a false-positive detection cycle, where a second labelling agent is applied instead of the first labelling agent in the labelling step, where the non-target compound is labelled by the second labelling agent with labelling efficiency $L_1$, where the target analyte is labelled by the second labelling agent with labelling efficiency $L_2$ and $L_1 \geq L_2$. In an embodiment disclosed herein, the number of non-target compounds present in the sample is estimated from the number of capture sites exhibiting a signal in the false-positive detection cycle. In a further embodiment disclosed herein, the number of target analytes present in the sample is estimated from the number of capture sites repeatedly exhibiting a signal in all detection cycles prior to the false-positive detection cycle and from the estimated number of non-target compounds present in the sample.

In an embodiment disclosed herein, the method includes a false positive detection cycle wherein the method does not comprise any labelling steps.

A false positive detection cycle may allow false positive signals originating from non-specifically bound labelling agents to be identified and discarded from analysis. For example, in an embodiment, specifically bound labelling agents may be deactivated by specific removal from the captured analytes prior to the false positive detection cycle. During the false positive detection cycle, no new labelling agents will become introduced to the captured analytes and hence only the non-specifically bound labelling agents, which remained behind after the deactivating step, may be triggered to produce a signal.

In an embodiment disclosed herein, the labelling agent comprises a detection modality, and where the step of triggering a signal(s) is by delivering detection agents to the detection modality.

In an embodiment, the detection modality may be comprised by an enzyme or a (bio)chemical catalyst able to continuously convert detection agents to molecular reporters. A molecular reporter may produce optical signals, electrical signals, magnetic signals or any other signal which may become detected using an imaging detector. In the case, where molecular reporters are continuously generated by the detection modality within a liquid compartment, the concentration of the molecular reporter may rapidly reach a detectable concentration within the compartment.

In an embodiment disclosed herein, the detection cycle comprises the step of subsequently removing labelling agents that has not labelled the analyte before triggering a signal from the at least one captured and labelled analyte.

Labelling agents may be added to captured analytes at a high concentration, such as to enable fast binding kinetics. Consequently, excess labelling agents may be removed by flushing subsequent to the labelling or re-labelling step.

In an embodiment disclosed herein, non-bound sample components are removed from the captured analyte or the captured and labelled analyte.

A sample may consist of a complex mixture of chemical or biological material, but where only the analytes may be of interest for the digital counting analysis. Hence, non-bound sample component may be removed from the captured analyte or the captured and labelled analyte, for example by a washing or rinsing procedure.

In an embodiment disclosed herein, the step of deactivation of signal(s) is selected from
  a) detaching the labelling agent from the captured analyte,
  b) deactivating the ability of the labelling agent to facilitate a signal or
  c) the combination of a) and b),
  and wherein the step of deactivation of signal(s) is optionally followed by a rinsing step.

Detachment of the labelling agent from the captured analyte may be achieved by disrupting the binding ability of the labelling agent to the captured analyte. Detachment may be carried out by for example raising the temperature, changing the chemical composition of the liquid hosting the captured and labelled analytes or by biochemical or chemical excision of the labelling agent from the captured analyte. For the detachment process to be viable, it should not disrupt the binding of the captured analyte to the capture site. Useful chemical agents that contribute to detachment are various chaotropic substances (i.e. substances, the presence of which provide for an increase in entropy). Useful chaotropic agents are for instance selected from the group consisting of n-Butanol, Ethanol, Guanidinium chloride, Lithium perchlorate, Lithium acetate, Magnesium chloride, Phenol, 2-propanol, Sodium dodecyl sulfate, Thiourea, and Urea.

Deactivation of the ability of the labelling agent to mediate a signal may be achieved by disrupting the detection modality of the labelling agent. For example, if the detection modality is constituted by an enzyme, then the ability of the enzyme to convert detection agent to molecular reporter should be disrupted. This usually requires knowledge of the molecular mechanism of the enzyme, but several methods known to those skilled in the art exist. For example, may an alkaline phosphatase enzyme become deactivated by treating it with ethylene-diamine-tetraacetic-acid (EDTA) or a horseradish peroxidase enzyme may become deactivated by treating it with phenol solutions.

Whereas detachment of labelling agents may be useful for selective removal of specifically bound labelling agents, then deactivation of the signal-mediating ability of the labelling agent may be useful for removing signals from non-specifically bound labelling agents. Non-specifically bound labelling agents may for example be attached to the surface of a capture site—and not to the captured analyte—thus potentially rendering the labelling agent resistant to specific detachment procedures. Consequently, by deactivating the signal-mediating ability of non-specifically bound labelling agents, the labelling agents will not produce false-positive signals in subsequent detection cycles.

In an embodiment disclosed herein, the method includes the capturing of the at least one analyte from the sample is by immobilization on the solid phase.

In an embodiment disclosed herein, the method includes the capturing of the at least one analyte from the sample is by using one or more capture probes specific to the analyte and where the capture probes are attached to the solid phase.

In an embodiment disclosed herein, a first number and a second number of detection cycles are used, and where the first number of detection cycles uses labelling agents differing from the second number of detection cycles.

Different types of labelling agents may be used in different detection cycles such as to either label different types of captured analytes or to label the same type of captured analyte with different labelling agents. The first process may be useful for detection of a large number of different analyte types, whereas the former process may be useful for (i) confirming the identity of a particular analyte or (ii) quantifying the presence of non-target compounds on the capture sites.

In an embodiment disclosed herein, one or more different capture probes for one or more distinct analyte types are attached to the solid phase.

The plurality of capture sites may be divided into regions or collections of capture sites, where each region or collection differs from the other by the type of capture probe attached to it. In this way, a great number of different analyte types may become captured and organized, such that a digital counting analysis may enable quantification of several different analyte types in the same measurement.

In an embodiment disclosed herein, one or more different labelling agents are used to label one or more distinct analyte types.

In an embodiment, where the plurality of capture sites exhibits several regions with different capture probes, such that several analyte types have been captured on the several regions, it may be useful to supplement the plurality of capture sites with a collection of different types of labelling agents during the labelling or re-labelling step. This may enable simultaneous labelling of all the different analyte types present on the plurality of capture sites and hence improve the multiplexing capacity of the digital counting analysis.

In an embodiment disclosed herein, the number of detection cycles is at least 3 cycles, at least 4 cycles, at least 5 cycles, at least 6 cycles, at least 7 cycles, at least 8 cycles, at least 9 cycles, or at least 10 cycles.

In an embodiment disclosed herein, the number of detection cycles is between 3-20 cycles, between 3-15 cycles, between 3-10 cycles, between 3-9 cycles, between 3-8 cycles, between 3-7 cycles, between 3-6 cycles, or between 3-5 cycles.

In an embodiment disclosed herein, the labeling agent is deactivated by detachment from the captured analyte and removed by flushing.

In an embodiment disclosed herein, the step of deactivating the signals is conducted in the plurality of liquid compartments.

In an embodiment disclosed herein, the labeling agent is deactivated by detachment from the captured analyte and where the detachment is by enzymatic cleavage.

In an embodiment disclosed herein, the labeling agent is deactivated by detachment from the captured analyte and where the detachment is by chemical cleavage or desorption by adjusting the pH, adjusting the ionic strength, adding denaturing salts or adding detergents.

In an embodiment disclosed herein, the labeling agent is deactivated by detachment from the captured analyte and where the detachment is by heating.

In an embodiment disclosed herein, the labeling agent is deactivated by changing its chemical or physical state.

In an embodiment disclosed herein, the labeling agent comprises an enzyme and wherein the state of the enzyme is changed by chemical or biochemical modification of the active site.

In an embodiment disclosed herein, the labeling agent comprises an enzyme and wherein the state of the enzyme is changed by chemical or physical disruption of the tertiary structure of the enzyme.

In an embodiment disclosed herein, the captured and labelled analyte is compartmentalized to produce liquid compartments hosting the captured and labelled analyte by introducing and withdrawing a hydrophilic liquid on the plurality of discrete capture sites, where each discrete capture site is rendered hydrophilic and where the plurality of discrete capture sites is placed on a hydrophobic substrate, such that upon withdrawing of the hydrophilic liquid a plurality of liquid droplets is formed and each droplet occupies one discrete capture site.

In an embodiment disclosed herein, the captured and labelled analyte is compartmentalized to produce liquid compartments hosting analyte by introducing a first hydrophilic liquid on the plurality of discrete capture sites followed by displacing the first hydrophilic liquid with a second liquid, where the two liquids are immiscible and where the second liquid is lighter than the first, and where each discrete capture site is rendered hydrophilic, and the plurality of discrete capture sites is placed on a hydrophobic substrate, such that upon displacement of the first hydrophilic liquid with the second liquid, a plurality of liquid droplets comprising the first hydrophilic liquid is formed and each droplet occupies one discrete capture site.

In an embodiment disclosed herein, captured and labelled analyte is compartmentalized to produce liquid compartments hosting analyte by introducing a first liquid to the plurality of discrete capture sites, where each discrete capture site is well-shaped or capillary-shaped, and where the first liquid is displaced by a second liquid, where the two liquids are immiscible and where the second liquid is lighter than the first, such that upon displacement of the first liquid, a plurality of liquid droplets comprising the first liquid is formed and each droplet occupies one discrete capture site.

In an embodiment disclosed herein, the captured and labelled analyte is compartmentalized to produce liquid compartments hosting analyte by introducing a liquid to the plurality of discrete capture sites, where each discrete capture site is well-shaped or capillary-shaped, and where the liquid is dispensed into the discrete capture site, such that each liquid compartment occupies one discrete capture site.

In an embodiment disclosed herein, the captured and labelled analyte is compartmentalized to produce liquid compartments hosting analyte by introducing a liquid to the plurality of discrete capture sites, where each discrete capture site is well-shaped, and where the liquid is displaced by applying a lid on the plurality of capture sites, such that a plurality of liquid droplets is formed and each droplet occupies one well-shaped capture site bounded by the lid.

In an embodiment disclosed herein, the captured and labelled analyte is compartmentalized to produce liquid compartments hosting the captured and labelled analyte by introducing a first liquid containing the plurality of discrete capture sites and the captured and the labelled analyte to a second liquid, where the second liquid is immiscible with the first liquid, such that a plurality of emulsion droplets consisting of the first liquid and enclosed by the second liquid is formed, and where each emulsion droplet contains at least one discrete capture site and at least one captured and labelled analyte.

In an embodiment disclosed herein, the positions of liquid compartments exhibiting a signal in each detection cycle are compared to the positions of liquid compartments exhibiting a signal in the other detection cycles, such that the number of consecutive detection cycles a liquid compartment exhibits a signal is counted, and where liquid compartments are classified in at least two categories, the first category of liquid compartments exhibiting a greater count than the second category.

The number of times a liquid compartment exhibits a signal is related to the identity of the captured compound within the compartment. For example, consider a capture site in which an analyte has been captured and another capture site in which a non-target compound has been captured. The analyte could be an oligonucleotide, which sequence contains a single base pair change, such as a single nucleotide polymorphism, and the non-target compound could be an oligonucleotide having the same sequence as the analyte, but without the single nucleotide polymorphism, i.e. having the wildtype sequence. In this embodiment, when both capture sites receive a labelling agent specific to the analyte, then the analyte will be preferentially labelled. However, the non-target compound might be labelled also, but with a lower efficiency. In this way, the liquid compartment hosting the target analyte may exhibit signals in all or most of the detection cycles, and the liquid compartment hosting the non-target compound may exhibit signals in few or none of the detection cycles. By comparison of the number of detection cycles in which each liquid compartment exhibited a signal, the compartment hosting the analyte may be distinguishable from the compartment hosting the non-target compound.

In an embodiment disclosed herein, the number of liquid compartments repeatedly exhibiting a signal in consecutive detection cycles is applied to calculate the concentration of target analytes in the sample.

In an embodiment disclosed herein, the number of discrete capture sites is at least 1,000, preferably at least 10,000, preferably at least 100,000, preferably at least 1,000,000, preferably at least 10,000,000.

In an embodiment disclosed herein, the discrete capture sites are circular or spherical and where the diameter of the individual discrete site is less than 1 mm, preferably less than 100 µm, preferably less than 10 µm, preferably less than 1 µm.

Circular capture sites may be formed by chemical or topographical patterning of a solid substrate, whereas spherical capture sites may be constituted by a collection of colloid beads.

In an embodiment disclosed herein, the discrete capture sites are circular or spherical and where the diameter of the discrete sites is between 0.5-5 µm, between 0.5-10 µm, between 0.5-50 µm, between 0.5-100 µm, between 10-1000 µm, between 50-1000 µm, between 100-1000 µm.

In an embodiment disclosed herein, the discrete capture sites are quadratic and where the length of the individual discrete site is less than 1 mm, preferably less than 100 µm, preferably less than 10 µm, preferably less than 1 µm.

In an embodiment disclosed herein, the discrete capture sites are quadratic and where the length of the discrete sites is between 0.5-5 µm, between 0.5-10 µm, between 0.5-50 µm, between 0.5-100 µm, between 10-1000 µm, between 50-1000 µm, between 100-1000 µm.

In an embodiment disclosed herein, the solid phase is
a) a solid substrate,
b) a colloid bead, or
c) a collection of colloid beads.

In an embodiment disclosed herein, the liquid compartments are in the form of a plurality of liquid nano-to-attoliter droplets under a gas phase seal.

In an embodiment disclosed herein, the liquid compartments occupy well-shaped capture sites, cavity-shaped capture sites or capillary-shaped capture sites.

In an embodiment disclosed herein, the liquid compartments are in the form of a plurality of water-in-oil emulsion droplets.

In an embodiment disclosed herein, the liquid compartments are in the form of a plurality of aqueous nano-to-attoliter droplets under a water-immiscible liquid phase.

In an embodiment disclosed herein, the digital counting is performed in a flow system for digital counting of one or more analyte types in a sample, the flow system comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets each having a maximum droplet volume, and the flow compartment configured to support a gas phase seal reducing evaporation of each nano-to-attoliter droplet.

In an embodiment disclosed herein, the gas phase seal establishes a vapor pressure within the flow system capable of reducing evaporation of the microdroplets.

In an embodiment disclosed herein, the gas phase seal reduces evaporation of each nano-to-attoliter droplet to less than 50 percent of the maximum droplet volume.

In an embodiment, the method disclosed herein comprises the step of (i) contacting a pattern of hydrophilic features in or on the hydrophobic substrate with a sample containing the one or more analyte types.

In an embodiment, a method disclosed herein comprises the step of (ii) capturing the one or more analyte types on the hydrophilic features.

In an embodiment, a method disclosed herein comprises the step of (iii) labeling the at least one captured analyte type with a labeling agent specific to the analyte type to be detected.

In an embodiment disclosed herein, the captured and labelled analyte is compartmentalized to produce liquid compartments hosting at least one analyte by step (iv) flowing across and withdrawing from the pattern a detection agent to produce the individual droplets in the form of nano-to-attoliter droplets.

In an embodiment disclosed herein, the method includes the step of (v) counting the number of the droplets hosting both the labeling and detection agent.

In an embodiment disclosed herein, the method comprises repeating steps (iii), (iv) and (v) one or more times.

In an embodiment disclosed herein, the method comprises repeating steps (iii), (iv) and (v) by using, instead of the first labeling agent, a second labeling agent specific to a second analyte type to be detected.

In an embodiment disclosed herein, the method comprises a step of deactivating the labeling agents present in the previous step before repeating steps (iii), (iv) and (v).

In an embodiment disclosed herein, the labeling agent is deactivated by detachment from the captured analyte and removed by flushing of the flow system.

In an embodiment disclosed herein, the labeling agent comprises an enzyme and a specific analyte recognition moiety, and the analyte recognition moiety is chosen from the following group of molecules: oligonucleotides, proteins, peptides, aptamers, antibodies, complexes thereof or synthetic variants thereof.

In an embodiment disclosed herein, the discrete capture site is the hydrophilic feature.

In an embodiment disclosed herein, one or more capture probes for one or more distinct analyte types are attached to the hydrophilic features.

In an embodiment disclosed herein, the method comprises more than one type of capture probe attached to the hydrophilic features, and wherein the different types of capture probes are arranged in regions.

In an embodiment disclosed herein, the capture probes are selected from the following group of probes: oligonucleotides, aptamers, proteins, antibodies, peptides or synthetic variants thereof.

In an embodiment disclosed herein, the sample containing the one or more analyte types in a liquid is contacted with the substrate containing the hydrophilic features by full immersion.

In an embodiment disclosed herein, the labelling is performed by bringing a solution containing a labelling agent for the analyte in contact with the captured analyte by full immersion.

In an embodiment disclosed herein, the analyte is a single- or double-stranded oligonucleotide, where the sequence of the oligonucleotide is a genomic sequence or a transcribed genomic sequence having one or more base-pair changes such as single nucleotide polymorphisms, insertions or deletions.

In an embodiment disclosed herein, the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

In an embodiment disclosed herein, the sample is derived from whole blood, plasma or serum.

In an embodiment disclosed herein, the sample is selected from the following group of samples: blood, plasma, serum, urine, saliva, cerebrospinal fluid, tear fluid, or tissue.

In an embodiment disclosed herein, the sample is selected from laboratory-processed samples of the following sample group: blood, plasma, serum, urine, saliva, cerebrospinal fluid, tear fluid or tissue.

In an embodiment disclosed herein, the digital counting analysis involves both single-molecule detection and quantification, In an embodiment disclosed herein, the captured analytes become covalently coupled to the capture probe(s) subsequent to capture.

A covalent bond between the captured analyte and the solid phase may ensure that the captured analyte does not detach from the solid phase during the step of deactivating signals. In an embodiment, the deactivation step serves to remove labelling agents from the captured analyte, but should be carried out in such a way as to preserve the captured analyte on the solid phase. A covalent bond is sufficiently strong to retain the captured analyte on the solid phase under most conditions, and hence may provide more flexibility in terms of the conditions applied to detach the labelling agent.

In an embodiment disclosed herein, the capture probe is an oligonucleotide or a synthetic oligonucleotide, the analyte is an oligonucleotide or a molecular complex containing oligonucleotides, where the analyte is bound to the capture probe via a sequence complementary to the capture probe sequence and where the covalent crosslinking is carried out by using an interstrand crosslinking agent such as platinum complexes, mitomycin C, nitrogen mustards, psoralens or aldehydes.

In an embodiment disclosed herein, the capture probe is a protein, an aptamer, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide, methylglyoxal or uranyl acetate.

In an embodiment disclosed herein, the capture probe is a synthetic oligonucleotide, where the synthetic modification incorporates a chemical group reactive towards the analyte such that covalent linkage can be established between analyte and capture probe subsequent to capture. In an embodiment disclosed herein, the covalent linkage between analyte and capture probe is triggered by contacting the analyte/capture probe-complex with a chemical agent. In an embodiment disclosed herein, the covalent linkage between analyte and capture probe is triggered by contacting the analyte/capture probe-complex with electromagnetic radiation.

In an embodiment disclosed herein, the analysis is single molecule digital counting analysis. In a further embodiment disclosed herein, the digital counting measurement comprises a single-enzyme linked molecular analysis (SELMA), digital polymerase chain reaction (dPCR), single enzyme-linked immunosorbent assay (sELISA) or digital single-enzyme linked immunosorbent assay (dELISA).

In an embodiment disclosed herein, the at least one analyte is an oligonucleotide, where the sequence of the oligonucleotide is a genomic sequence or a transcribed genomic sequence having one or more base-pair changes such as single nucleotide polymorphisms, insertions or deletions, and where the sample potentially contains more than one non-target oligonucleotide(s), the non-target oligonucleotide(s) having the same genomic sequence or transcribed genomic sequence as the target, but without the one or more base-pair changes.

In an embodiment disclosed herein, the sample contain a first and a second analyte type, where the first analyte type has a first sequence and a first concentration in the sample, where the second analyte type has a second sequence and a second concentration in the sample, where the first and the second sequence are different, where the first and the second sequence are genomic sequences or transcribed genomic sequences, and where as described herein the first and the second concentration is measured and compared to each other to identify copy number variations.

In an embodiment disclosed herein, the gas phase is provided by atmospheric air, and the capture probes are selected from the group of single-stranded DNA oligos, single-stranded locked nucleic acid oligos or single-stranded peptide nucleic acid oligos; different types of capture probes are arranged in regions; the analytes are single-stranded DNA extracted from a processed blood sample; the labelling agent comprises a detection modality and a recognition moiety; the detection modality is an enzyme and the recognition moiety is selected from the group of single-stranded DNA oligo, a single-stranded locked nucleic acid oligo or a single-stranded peptide nucleic acid oligo.

A digital counting measurement allows single analyte molecules to become directly detected, and hence counted to determine their concentration in a sample. Digital counting measurements are applied in digital polymerase chain reaction (dPCR), digital enzyme-linked immunosorbent assay (dELISA) and variant thereof. For dPCR single nucleotide analytes are isolated in reaction compartments and subjected to polymerase-assisted nucleotide amplification and fluorescence labeling of the amplicons. For dELISA single protein/peptide analytes are captured on the surface of micro-colloid particles, labelled with enzyme-conjugated antibodies, isolated in microscopic reaction compartments and supplied with detection reagents. The detection reagents produce an optical signal (e.g. fluorescence, chemiluminescence, absorbance) when processed by the enzyme, which due to the microscopic volume of the reaction compartment rapidly reaches a detectable concentration. The principle of a digital counting measurement is outlined in FIG. 8.

In an embodiment disclosed herein, to conduct a digital counting measurement of a given analyte using the flow system as described herein, at least the following three general steps are required; (1) analyte capture, (2) analyte labelling and (3) analyte counting, see for example the sketch in FIG. 9. In step 1, analytes from a sample become specifically captured on the hydrophilic features. In step 2, the captured analytes become specifically labelled with a suitable agent, e.g. an enzyme-conjugate. In step 3, an array of micro-droplets is formed such that the liquid contains a detection agent. In the case where the labelling agent is an enzyme, the detection agent could be a fluorogenic-/chromogenic-/chemiluminescent substrate for the enzyme. Upon processing of the substrate a detectable optical signal is produced in droplets, which initially harbored both the labelling agent and the detection reagent. Next, droplets producing a signal may be counted by optical imaging of the array.

In one embodiment, the flow system comprises one or more capture probes for one or more distinct analyte types, the capture probe(s) being attached to the hydrophilic features. In a further embodiment the different types of capture probes are arranged in regions.

An advantage of the present invention over that of dPCR and micro-colloid assisted dELISA is that analytes may become captured and organized specifically on the hydrophilic features. This is appreciated when it comes to (i) measuring several different analyte types in a single measurement and (ii) if a repeated measurement is desired.

In the first case, different capture probes may be placed on different regions in the flow compartment, such that a capture probe specific to one analyte type is localized in a first region, another capture probe specific to another analyte type is localized in a second region and so forth. This is a well-known strategy in the field of DNA- and protein-microarray studies in which several hundred target analytes can be detected in a single measurement, see for example the review by Weinrich, D. et al entitled "Applications of Protein Biochips in Biomedical and Biotechnological Research" published in *Angewandte Chemie International Edition* (2009), vol. 48, pp. 7744-7751. (DOI: 10.1002/anie.200901480).

In the second case, it is possible to repeat the digital counting by removing labelling and detection agents and re-introducing them to the flow system. Because the captured analytes remain immobilized on the hydrophilic features, the digital counting measurement may be repeated in order to improve e.g. the signal-to-noise ratio, see Example 5. This is not possible for either dPCR or dELISA, because labelling and detection agents cannot be removed without also removing the analytes.

In one embodiment, the one or more capture probes for one or more distinct analyte types are attached to the hydrophilic features by a linker moiety. The linker molecule serves to connect the—in most cases—hard inorganic surface of the hydrophilic features to the soft organic capture probes. Linker molecules may thus contain a dual chemical functionality in order to connect the capture probe to the surface. Linker molecules may be chosen to be poly(ethylene-glycol) polymers, which are flexible, inert and hydrophilic. They may also be chosen to be linear alkane chains. Poly(ethylene glycol) linkers may be prepared in different sizes/lengths and hence provide a greater separation between the surface and the capture probe, whereas alkane chains are generally shorter. Other linker molecules include but are not limited to polypeptides or oligonucleotides. The chemical functionality present on the linker molecule may be chosen from a great selection of reactive chemical groups such as aldehyde, alkyne, amine, azide, biotin, Boc/Fmoc-protected amine, carboxylic acid, epoxides, hydrazide, hydroxyl, maleimide, N-hydroxysuccinimide, thiols, vinylsulfones and variants thereof.

In one embodiment, more than one type of capture probes is attached to the hydrophilic features, and the different types of capture probes are arranged in regions. In one embodiment, the capture probes are selected from the following group of probes: oligonucleotides, proteins, peptides or synthetic variants thereof.

In the case where the capture probe is an oligonucleotide, the probe may be able to capture other oligonucleotides, which display a complementary sequence to that of the capture probe. Synthetic oligonucleotide variants, such as locked nucleic acids (LNA) or peptide nucleic acids (PNA), which exhibit strand-invading properties may also be utilized to capture single- or double-stranded DNA. Aptamers too may be utilized as capture probes to enable the capture of proteins or peptides. Furthermore, antibodies or fragments of antibodies may become used as capture probes in order to mediate specific capture of proteins, peptides or small molecules.

In an embodiment as disclosed herein, the method further comprises the step of (i) contacting a pattern of hydrophilic features in or on a hydrophobic substrate with a sample containing the one or more analyte types.

In an embodiment as disclosed herein, the method further comprises the step of (ii) capturing at least one analyte type on the hydrophilic features.

A great number of analyte types may become captured on hydrophilic features, which have undergone (bio)chemical functionalization as previously described in more detail. For example, to specifically capture oligonucleotide-based analytes such as RNA, mRNA, viral RNA, DNA, viral DNA, bacterial DNA, DNA/RNA-complexes or protein/DNA/RNA-complexes, it may be necessary to apply oligonucleotide-based capture probes displaying complementary oligonucleotide sequences to those of the analyte. To specifically capture protein- or peptide-based analytes or complexes thereof, it may be necessary to apply antibody- or aptamer-based capture probes, which specifically recognize the tertiary structure of the analyte, i.e. an antigen/antibody association. Analytes comprising entire biological entities or macro-molecular assemblies such as cells, bacteria, virus, virus-like particles, nanoparticles or cellular fragments may be captured in the same way by using antibodies specifically targeting antigens displayed by the analyte. Alternatively, the aforementioned analyte types may be captured without the aid of capture probes, but instead by matching the size of the micro-droplet (i.e. the $V_D$-value) to the size of the analyte, such that only one analyte may be able to reside in a droplet.

Furthermore, the capture probes may be supplemented with helper probes to mediate the capture, such that the helper probe first binds specifically to the analyte, and next binds specifically to the capture probe on the surface, thus acting as a tether, e.g. see the sketch in FIG. 9.

In addition, all of the aforementioned analyte types may become non-specifically captured on the hydrophilic features by use of heterobifunctional chemical crosslinking agents, such that one end of the crosslinking agent binds to the analyte and the other binds to the surface.

In an embodiment as disclosed herein, the method further comprises the step of (iii) labeling the at least one captured analyte type with a labeling agent specific to the analyte type to be detected.

The labeling agent may be selected in the same way as the capture probe, in order to mediate specific labeling of the analyte. For example, if the analyte is an oligonucleotide, then both the capture probe and the labeling agent may be oligonucleotides or synthetic variants thereof. In this case, the capture probe may recognize one specific sequence on the analyte and the labeling agent may recognize another specific sequence. The labeling agent may contain one module for the specific recognition of the analyte and another module for the subsequent detection of the analyte. At least three classes of labeling agents fulfill these criteria; enzyme-conjugated oligonucleotides, enzyme-conjugated proteins/peptides or enzyme-conjugated aptamers. The analyte-recognition module is provided by the oligonucleotide, the protein/peptide or the aptamer, respectively, whereas the detection module is provided by the enzyme.

In an embodiment as disclosed herein, the method further comprises the step of (iv) flowing across and withdrawing from the pattern a detection agent to produce the individual droplets in the form of nano-to-attoliter droplets.

With the formation of aqueous microdroplets containing detection reagents, it is possible to trigger signal-generation in the subset of droplets presenting both the labeling agent and the detection agent. In the case where the labeling agent comprises an enzyme, a suitable detection reagent would be any compatible enzyme substrate able to generate an optical signal in response to enzymatic processing. For example, in the case where the enzyme belongs to the class of peroxidases suitable detection agents include ABTS (2,2'-Azinobis [3-ethylbenzothiazoline-6-sulfonic acid]-diammonium salt), OPD (o-phenylenediamine dihydrochloride), TMB (3,3',5, 5'-tetramethylbenzidine), as well as the following tradename products Quantablu, QuantaRed, Amplex UltraRed or SuperSignal ELISA pico/femto. In the case, where the enzyme belongs to the class of phosphatases suitable detection agents include PNPP (p-Nitrophenyl Phosphate), 4-MUP (4-Methylumbelliferyl phosphate), BCIP/NBT (5-Bromo-4-chloro-3-indolyl phosphate/nitro blue tetrazolium), as well as the following tradename products CSPD, CPD Star or Dynalight. In the case where the enzyme belongs to the galactosidase class, suitable detection agents include FDG (Fluorescein Di-β-D-Galactopyranoside), DDAO galactoside (9H-(1,3-Dichloro-9,9-Dimethylacridin-2-One-7-yl) β-D-Galactopyranoside), MUG (4-Methylumbelliferyl β-D-Galactopyranoside), ONPG (o-nitrophenyl-β-D-galactopyranoside), Resorufin β-D-Galactopyranoside, X-gal (5-Bromo-4-Chloro-3-Indolyl β-D-Galactopyranoside), as well as the following tradename products Galacton-Star or Bluo-Gal. Furthermore, any ELISA-compatible enzyme/substrate pair may be applied.

In an embodiment as disclosed herein, the method further comprises the step of (v) counting the number of the droplets hosting both the labeling and detection reagent.

The counting of droplets exhibiting an optical signal is most conveniently executed with the aid of an imaging device, such as an optical microscope. Using microscopy, individual droplets may be imaged and their signal level evaluated from the relative intensity units of the micrograph. In the case, where the signal is chemiluminescent or fluorescent in nature, the acquired micrographs may be recorded using a fluorescence filterset. Furthermore, as shown in Example 4, fluorescence micrographs may be supplemented with brightfield micrographs acquired on the same position, such as to verify the position and appearance of the droplets and to correlate it to the position of the fluorescence signal.

In the case where the signal is colorimetric in nature, the acquired micrographs may be recorded by brightfield microscopy imaging such as to evaluate the absorbance, reflectance or transmittance of individual droplets.

In the case, where the droplet array covers a large area, such that the field-of-view of a single micrograph cannot contain it, several micrographs may be recorded at several positions in order to reconstruct a larger micrograph displaying the entire array. In order to guide the imaging reconstruction (e.g. micrograph stitching) easily recognizable micro-patterns may be incorporated on the array.

In an embodiment as disclosed herein, the method further comprises repeating steps (iii), (iv) and (v) one or more times.

In an embodiment as disclosed herein, the method further comprises repeating steps (iii), (iv) and (v) by using, instead of the first labeling agent, a second labeling agent specific to a second analyte type to be detected.

In an embodiment as disclosed herein, the method further comprises a step of deactivating the labeling agents present in the previous step before repeating steps (iii), (iv) and (v).

The ability to repeat the steps of labeling, adding detection reagents and counting the signal-positive droplets is a unique property of a SELMA measurement, which poses at least two advantages:

Firstly, by removing labeling and detection agents from a previous measurement and subsequently re-introducing them may increase the signal-to-noise ratio. This is due to the fact that labeling agents may bind non-specifically to the surface of the hydrophilic features without any analytes present. The non-specifically bound labeling agents may thus comprise a background noise in the counting measurement and hence lead to a potentially low signal-to-noise ratio. However, because the non-specific binding takes place at random positions on the array, whereas the specific binding to the analyte takes place only on the array features having an analyte present, then the two binding modes may be distinguished by a repeated measurement. In repeated measurements, a droplet only exhibiting non-specific binding may not provide a positive signal every time the measurement is repeated, whereas a droplet exhibiting specific binding may provide a positive signal each time. In this way, the background noise may be significantly reduced, thus leading to a greater measurement sensitivity.

Secondly, by removing labeling and detection agents specific to a first analyte type from a previous measurement and subsequently introducing labeling and detection agents specific to another analyte type may provide higher multiplexing capacity. In this case, each time the measurement is repeated a new set of analyte types become counted. For example, if the array is functionalized with capture probes specific to 10 different analyte types, then by repeating the measurement 10 times—each time introducing new labeling and detection agents—all 10 analytes may become quantified.

In an embodiment as disclosed herein, the labeling agent is deactivated by detachment from the surface-bound analyte and removed by flushing of the flow system.

As is known to those skilled in the art, there exists numerous approaches to deactivating molecular probes. In the case of a SELMA measurement, the most convenient approach relies on releasing the labeling agent from the analyte, while retaining the analyte bound to the capture probe. Once the labeling agent has become detached it may be removed by flushing the flow channel with a rinsing solution. Detection agents are more readily removed since they are not intended for binding to the array surface, and hence does not require a detachment step.

In an embodiment as disclosed herein, the labeling agent is detached by enzymatic cleavage.

In the case where the capture probe, the analyte and the labeling agent are oligonucleotides it is possible to specifically remove the labeling agent by exonuclease treatment. An exonuclease is an enzyme, which degrades double-stranded DNA, such as the complementary sequence between the analyte and the labeling agent. By rendering the capture probe inert to exonuclease treatment (e.g. by choosing a peptide nucleic acid, a locked nucleic acid or a chemically modified single-stranded DNA as the capture probe) only the binding between analyte and labeling agent may become disrupted.

In one embodiment, the labeling agent is detached by chemical cleavage or desorption, for example by adding or adjusting pH, ionic strength, denaturing salts or detergents.

In one embodiment, the labeling agent is detached by raising the temperature of the flow system.

In one embodiment, the labeling agent is deactivated by changing its chemical or physical state.

In an embodiment, where the analyte and the labeling agent both are oligonucleotides and bound to each other by base-pair sequence complementarity it is possible to specifically remove the labeling agent by changing the pH or the ionic strength of the solution. For example, when the pH is raised the double-stranded structure of DNA is disrupted due to deprotonation of the nucleobases. Furthermore, detachment of duplex DNA may also be achieved by decreasing the ionic strength of the solution, thus enhancing the electrostatic repulsion between the charged phosphate groups on the DNA backbone. Even further, by increasing the temperature to above the melting transition of duplex DNA may lead to separation of the labeling agent from the analyte.

In an embodiment, where the analyte and the labeling agent are protein- or peptide-based, the labeling agent may become detached by disrupting/denaturing the tertiary structure using detergents, denaturing salts or by increasing the temperature.

In one embodiment, the labeling agent comprises an enzyme and the labelling agent may become deactivated by changing the state of the enzyme by chemical or biochemical modification of the active site.

Enzymes may become deactivated by disrupting the active site, such that further enzymatic processing is not possible. For example, in the case where the enzyme belongs to the class of peroxidase enzymes, the active site becomes irreversibly disrupted, when exposed to phenol solutions, see for example the work of Mao, L., Luo, S., Huang, Q. and Lu, J. in "Horseradish peroxidase inactivation: Heme destruction and influence of polyethylene glycol" published in Scientific Reports, vol. 3, article number 3126 (2013) (DOI: 10.1038/srep03126). Furthermore, in the case where the enzyme belongs to the class of phosphatase enzymes, the active site requires a zinc- and magnesium-ion complex to function. Consequently, by removal of these ions using chelating agents such as EDTA (ethylene-diamine-tetraacetic acid) may lead to irreversible inactivation of the enzyme, i.e. termination of enzyme activity, see for example the work of Ackermann, B. P. and Ahlers, J. in "Kinetics of alkaline phosphatase from pig kidney. Influence of complexing agents on stability and activity" published in Biochemical Journal, vol. 153, pp. 151-157 (1976) (DOI: 10.1042/bj1530151).

In one embodiment, the labeling agent comprises an enzyme and wherein the state of the enzyme is changed by chemical or physical disruption of the tertiary structure of the enzyme.

For example, the structure of an enzyme may be changed by increasing the temperature of the solution, by increasing or decreasing the pH, by increasing or decreasing the ionic strength of the solution, by adding detergents or by using chemical crosslinking agents to covalently modify the enzyme.

In one embodiment, the labeling agent comprises an enzyme and a specific analyte recognition moiety, and the analyte recognition moiety is chosen from the following group of molecules: oligonucleotides, proteins, peptides, aptamers, antibodies, complexes thereof or synthetic variants thereof.

In one embodiment, the sample containing the one or more analyte types in a liquid is contacted with the substrate containing the hydrophilic features by full immersion.

In one embodiment, the method further comprises removing the liquid and washing the substrate.

In one embodiment, the labeling is performed by bringing a solution containing a labelling agent for the analyte in contact with the captured analyte by full immersion.

In one embodiment, the method further comprises removing the solution containing residual labelling agents and washing the substrate.

In an embodiment disclosed herein, the substrate hosting the pattern of hydrophilic features is situated inside a flow compartment thus enabling liquid contact by pressure-driven actuation of liquid plugs from the inlet to the outlet. Different solutions containing different reagents (labeling agents, detection agents, deactivation agents, rinsing solutions) may be loaded into the liquid loading pad and actuated into the flow compartment. The liquid contact mode may be classified as (i) a flow-through contact or (ii) as an infuse-stop-withdraw contact. In a flow-through contact mode, a liquid plug is actuated across the flow compartment until the entire volume of the plug has passed through. In an infuse-stop-withdraw contact mode, a liquid plug is actuated until it fills out the entire volume of the flow compartment and then stopped. Following a certain waiting period, the plug is actuated out of the flow channel and into the liquid outlet.

The flow-through contact mode is typically suitable for reaction steps in which the reagents are in excess. The duration of such a step may be determined by the flow-rate (volume/time) and the volume of the liquid plug and may be adjusted in order to achieve the required process time. Steps such as rinsing steps, labeling steps, deactivation steps and detection steps could typically be performed in flow-through contact mode.

The infuse-stop-withdraw contact may be suitable for steps requiring longer incubation times and where the reagents are present at low concentrations. For example, the capture step in which a sample containing a low concentration of analytes is to be bound to the capture probes on the surface of the hydrophilic features. For a capture step, it may be advantageous to prolong the duration of the step in order to ensure complete capture of all analytes from the sample, i.e. a sufficient incubation time to allow for analytes to diffuse from the top to the bottom of the flow compartment, as well as sufficient time to enable successful capture at the surface. The infuse-stop-withdraw contact is equivalent to full immersion of the hydrophilic pattern in a solution.

In one embodiment, the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

In one embodiment, the sample is selected from the following group of samples: blood, plasma, serum, urine, saliva, cerebrospinal fluid, tear fluid, or tissue.

In one embodiment, the sample is selected from laboratory-processed samples of the following sample group: blood, plasma, serum, urine, saliva, cerebrospinal fluid, tear fluid or tissue such as blood.

Depending on the type of sample, different kinds of analyte types may be present, and different laboratory protocols may be required in order to prepare the analytes for the measurement. For example, if the sample is a blood sample, it might be necessary to treat the blood with an anticoagulant (e.g. ethylene-diamine-tetra-acetic acid (EDTA), citrate or oxalate) to prevent clotting. Another example of laboratory processing of a blood sample could be to centrifuge or filter the blood in order to remove cells from the sample. Even another example of laboratory processing of a blood sample could be to dilute the blood or to add active components to facilitate specific extraction of the biomarker of interest. For example, DNA analytes may be purified from liquid samples using solid-phase reversible immobilization, in which the blood is mixed with crowding agents and carboxylic acid coated paramagnetic microparticles. These reaction conditions may favor the selective adsorption of DNA to the surface of the microparticles, which may then become extracted by application of a magnetic field. For other applications, it might be advantageous to subject the diluted—or otherwise processed—sample to (i) an electrophoretic step or (ii) a dialysis step to select molecules from the sample based on their charge, size and molecular weight.

In one embodiment, the one or more captured analytes become covalently crosslinked or coupled to the capture probe subsequent to capture.

It may be advantageous to establish a covalent link between the analyte and the capture probe, because it provides an essentially irreversible immobilization of the analyte to the surface. In this way, detachment of the labelling agent may be more readily achieved, because the link between analyte and labelling agent is non-covalent and thus weaker. For example, if both the capture probe and the analyte are oligonucleotides and bound together by complementary base-pairing and in addition bound together through one or more covalent linkages, and if the labeling agent is also an oligonucleotide, but only bound to the analyte by complementary base-pairing, then the labelling agent may be readily dissociated from the analyte by subjecting the complex to alkaline pH. The alkaline pH is not likely to affect a strong covalent linkage between capture probe/analyte to the same extent as the weaker base-pairing link between analyte/labelling agent.

As another example, consider that the capture probe is an antibody and the analyte is a protein or a peptide, and that a covalent link has been established between the two. If the labelling agent is antibody-based, and bound to the analyte through antibody/antigen-interactions, then it may be readily removed by adding detergents or by adding denaturants, while still retaining the covalent link between the capture probe and the analyte.

In one embodiment, the capture probe is an oligonucleotide or a synthetic oligonucleotide, the analyte is an oligonucleotide bound to the capture probe via a base-pairing to the capture probe sequence and the covalent crosslinking is carried out by using an interstrand crosslinking agent such as platinum complexes, mitomycin C, nitrogen mustards, psoralens or aldehydes. Interstrand crosslinking agents as the ones mentioned above are capable of forming covalent bonds between nucleobases on opposing strands in duplex DNA, duplex DNA/RNA or synthetic variants thereof containing nucleobases. An interstrand covalent linkage provides enhanced stability as compared to the non-covalent interstrand base-pairing linkage, thus providing a virtually irreversible immobilization of the analyte to the capture probe and hence the hydrophilic feature.

In one embodiment, the capture probe is a protein, a peptide or synthetic variants thereof, the analyte is a protein, a peptide or complexes containing proteins or peptides, the analyte is bound to the capture probe by structural recognition of a specific region of the analyte and the covalent crosslinking is carried out by using a chemical fixation agent such as formaldehyde, glutaraldehyde, osmium tetroxide or uranyl acetate. Chemical fixatives as the ones mentioned above are able to crosslink amino acids, thus providing covalent linkages at the contact zone between the analyte and the capture probe. This may lead to a virtually irreversible immobilization of the analyte to the capture probe and hence the hydrophilic feature.

In an embodiment of the method and the flow system described herein, the gas phase is provided by atmospheric air, and/or the capture probes are selected from the group of single-stranded DNA oligos, single-stranded locked nucleic acid oligos or single-stranded peptide nucleic acid oligos, and/or the different types of capture probes are arranged in regions, and/or the analytes are single-stranded DNA extracted from a processed blood sample, and/or the labelling agent comprises a detection modality and a recognition moiety, and/or the detection modality is an enzyme and/or the recognition moiety is selected from the group of single-stranded DNA oligo, a single-stranded locked nucleic acid oligo or a single-stranded peptide nucleic acid oligo.

In another embodiment of the method and the flow system described herein, the gas phase is provided by atmospheric air, the capture probes are selected from the group of single-stranded DNA oligos, single-stranded locked nucleic acid oligos or single-stranded peptide nucleic acid oligos, the different types of capture probes are arranged in regions, the analytes are single-stranded DNA extracted from a processed blood sample, the labelling agent comprises a detection modality and a recognition moiety, the detection modality is an enzyme and the recognition moiety is selected from the group of single-stranded DNA oligo, a single-stranded locked nucleic acid oligo or a single-stranded peptide nucleic acid oligo.

In the following, some non-limiting examples of applications are described:

In an embodiment disclosed herein, use of a solid phase having a plurality of discrete capture sites, each site being capable of capturing the at least one analyte in a method as described herein.

In an embodiment disclosed herein, use of a solid phase having a plurality of discrete capture sites, each site being capable of capturing the at least one analyte in a method as described herein for reducing counting error in a digital counting analysis.

In an embodiment disclosed herein, use of a solid phase having a plurality of discrete capture sites, each site being capable of capturing the at least one analyte for reducing counting error in a digital counting analysis by performing at least two detection cycles as described herein.

Single enzyme-linked immunosorbent assays (sELISA), in which protein or peptide analytes are captured by surface-bound antibody-probes and later labeled and detected by single enzyme-conjugated detection probes.

Single oligonucleotide hybridization assays, in which oligonucleotide analytes are captured by surface-bound complementary oligonucleotide-probes and later labeled and detected by single enzyme-conjugated detection probes.

Another class of applications deals with manipulation and quantification of single biological entities, such as cells, cellular fragments/organelles, bacteria, virus capsids, etc. In these cases, the assay may use surface-bound capture-probes to immobilize any of the aforementioned biological entities and later apply specific detection-probes to quantify their number and kind. Alternatively, after the biological entities have been captured, they may be ruptured and their content of proteins, peptides, lipids or oligonucleotides may be captured by another set of surface-bound capture probes and later labeled and detected by single enzyme-conjugated detection probes.

Furthermore, the invention would be suitable for conducting digital polymerase chain reaction (dPCR) or variants thereof. In one embodiment of the invention, the dPCR assay detects specific oligonucleotide sequences by containing the target sequence as well as amplification reagents and detection probes within a single droplet. As the PCR takes place, the target sequence becomes amplified and thus rendered detectable by the detection probes. In another embodiment of the invention, the target oligonucleotide is first specifically captured by surface-bound probes and next amplification reagents and detection probes are supplied to the individual droplets to allow for the PCR and detection reaction to take place.

In one embodiment, the systems and methods described herein include a channel-shaped flow compartment that has a surface for supporting a plurality of microdroplets. In an embodiment, the systems and methods described herein provide an improved seal for microdroplets and to that end provide a gas-phase seal. In an embodiment, as disclosed herein the channel shaped flow compartment also has a surface that extends over the surface supporting the microdroplets and includes walls so that the channel-shaped flow compartment has two openings, one on either side of the flow compartment. In one embodiment, the channel is rectangular with a square cross-section so that each opening is square. In other embodiments, the flow compartment is cylindrical and each opening is circular. In both these embodiments, the microdroplets are spaced apart from each other, for example in an array, and located centrally within the flow compartment. In an embodiment, the centrally located microdroplets are spaced a length ($L_E$) away from each of the openings. In one embodiment, the height (h) of the flow compartment is selected based in part on the aggregate volume of fluid contained in the microdroplets, the temperature and pressure of the ambient environment contacting the flow compartment and the length $L_E$. In one embodiment, the height h is selected to create a vapor pressure within the flow compartment that reduces the rate at which the microdroplets will evaporate. Not to be bound by theory, but as the microdroplets evaporate, the vapor from the evaporation creates a gas-phase seal that reduces the rate at which evaporation takes place as compared to the rate that the microdroplets would experience if generally exposed to the ambient environment. In one practice, it is understood that for aqueous solutions, a certain fraction of the water will evaporate into the gas-phase. However, the degree of evaporation can be predicted and rationally controlled by choosing (i) the right flow channel depth and geometry, (ii) the right droplet volume and (iii) the right microdroplet array geometry. By selecting the parameters correctly, the microdroplets will not evaporate due to the vapor pressure, and thus increased humidity, in the flow channel. This provides a gas-phase seal, which is similar to a chemical seal, but instead of covering the flow compartments with a liquid phase, the micro-droplets are maintained in a gas-phase, such as air. The advantage of a gas-phase as compared to a liquid phase is that many large biomolecules (proteins, DNA, lipids, etc.) do not partition into air, because their boiling point is significantly higher than water. Unlike the chemical seal, a gas-phase seal allows reagents to be easily introduced on the array without having to remove an oil-phase.

For embodiments where the flow compartments store micro-droplets resting on a planar substrate held in place by surface tension and integrated into a flow channel, a gas-phase seal can be established by contacting the array with a liquid followed by liquid withdrawal. Upon liquid withdrawal the array will retain the micro-droplets and the flow channel will be filled with for example air, thus establishing a gas-phase seal. Thus, the systems and methods described herein provide, among other things, a surface-tension based micro-droplet array embedded in a flow channel, in which the geometry of the flow channel is matched to the geometry of the array, such as to reduce the evaporation below a certain fraction, e.g. less than 5%.

Herein, the feature of the hydrophilic features being configured to support a plurality of liquid nano-to-attoliter droplets may particularly mean that the hydrophilic features form a pattern of material having a first hydrophilic property surrounded by material having a second hydrophilic property, the first property being more hydrophilic than the second property, meaning that the contact angle is lower for droplets on the material with the first hydrophilic property. In one example, the material with the second hydrophilic property is considered to be hydrophobic whereby the droplets are essentially exclusively located at the material having the first hydrophilic property.

The feature of the flow compartment being configured to support a gas phase seal reducing evaporation refers to the volume of the flow compartment relative to the volume of the droplets. A flow compartment having a volume $V_C$ being within the boundaries set by the formula:

$$V_{DA} < V_C < V_{MAX} = V_{DA}\frac{\rho_L RT}{(1-RHI)M_W P_0}\exp\left(\frac{\Delta H_{VAP}}{R}\left(\frac{1}{T} - \frac{1}{T_0}\right)\right)$$

is herein considered to be within the definition of a compartment being configured to support a gas phase seal reducing evaporation.

An example of a gas phase, which reduces evaporation, could be a vapor essentially being at its saturation temperature and pressure such that it is incapable of increasing the relative humidity, i.e. near 100 pct. humidity or at least in the range of 90-100 pct. such as in the range of 95-100 pct. humidity. The term "opening" means an entrance for the sample to enter the hydrophilic features on the hydrophobic substrate. The opening could be formed by one or more inlets of the same or different sizes from outside into the compartment.

The flow compartment is a compartment in which the sample can flow and which houses the hydrophilic features on the hydrophobic substrate. The flow compartment could be formed by one or more distinct chambers. If it is defined by more than one chamber, the chambers are in fluid connection.

A capture probe is a feature which is capable of capturing a specific constituent. The capture probe may e.g. be based on PNA or DNA, e.g. a single-stranded PNA oligo.

In one embodiment, the support for the hydrophilic features is located centrally within the flow compartment. In one example, the support for the hydrophilic features are surrounded in the flow compartment by a hydrophobic material forming a boundary about the support for the hydrophilic features.

Specific Embodiments of the Invention

Flow System for Digital Counting Using a Flow Compartment

Disclosed herein is a flow system useful for digital counting of one or more distinct analyte types in a sample such as in the methods and uses described herein, comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets. In an embodiment, the flow compartment is configured to support a gas phase seal reducing evaporation of each nano-to-attoliter droplet. In an embodiment, the gas phase seal reduces evaporation of each nano-to-attoliter droplet to less than 50 percent of the maximum droplet volume.

In an embodiment disclosed herein, the flow system comprises a droplet region providing a pattern of hydrophilic features in or on a hydrophobic substrate to enable formation of evaporation resistant gas-phase-sealed nano-to-attoliter droplets.

In an embodiment disclosed herein, the flow system comprises one or more flow compartments, such as flow channels, overlaying the droplet region to enable liquid contact to the hydrophilic/hydrophobic pattern.

In an embodiment disclosed herein, the flow system comprises a liquid loading pad for supplying the flow compartment and droplet region with liquids and reagents.

In an embodiment disclosed herein, the flow system comprises a liquid inlet connecting the flow compartment to the liquid loading pad.

In an embodiment disclosed herein, the flow system comprises a liquid outlet connecting the flow compartment to a pressure source providing suction, and hence mediate liquid actuation through the flow compartment.

In a further embodiment disclosed herein, the flow system comprises at least five distinct elements in order to function as a single molecule digital counting device, see also FIG. 10.

These are as follows
- A droplet region providing a pattern of hydrophilic features surrounded by a hydrophobic substrate to enable formation of evaporation resistant gas-phase-sealed nano-to-attoliter droplets
- One or more flow compartments overlaying the droplet region to enable liquid contact to the hydrophilic/hydrophobic pattern
- A liquid loading pad for supplying the flow compartment with liquids and reagents
- A liquid inlet connecting the flow compartment to the liquid loading pad
- A liquid outlet connecting the flow compartment to a pressure source to provide suction, and hence mediate liquid actuation through the flow compartment.

The aforementioned five features define an exemplary flow system, where liquid is actuated across the flow compartment by means of a pressure drop from the inlet to the outlet. Instead of applying suction, the liquid reagents in the loading pad may be pushed through the flow channel. This would require the loading pad to be connected on one side to a pressure source and on the other side to the liquid inlet. In this case, the liquid outlet would not be required to be connected to a pressure source. Alternative means of actuating the liquid flow could be by gravity, in which case no pressure source would be necessary, or by dielectrophoretic actuation, which requires electrodes to be embedded in the flow channel. In one embodiment disclosed herein, liquid actuation is suction-driven.

As is known to those skilled in the arts, similar functional flow systems may be fabricated by a multitude of different approaches. These include but are not limited to:
1. Using computer numeric controlled (CNC) milling, injection molding, hot embossing or 3D printing to fabricate flow compartments in solid substrates.
2. Applying any solid substrate compatible with CNC milling, injection molding, hot embossing or 3D printing.
3. Producing the flow system out of one or more components and subsequently bonding the components together to achieve the desired geometry or functionality. Bonding techniques include pressure sensitive adhesive film, spray coating of liquid adhesives, thermal bonding, ultrasonic welding or laser welding. Instead of bonding, the individual components may be mechanically, electromechanically or magnetically clamped such as to produce a final assembly. For an overview of bonding and fabrication processes utilized for microfluidic applications, see the review by Temiz, Y., Lovchik, R., Kaigala, G. V. and Delamarche, E. in "Lab-on-a-chip devices: How to close and plug the lab" published in Microelectronics Engineering, vol. 132, pp. 156-175 (2015) (DOI: 10.1016/j.mee.2014.10.013).

As disclosed herein, the hydrophilic features on the substrate are configured to support a plurality of liquid nano-to-attoliter droplets each having a maximum droplet volume. The hydrophilic surface may be any kind which is capable of holding a droplet having that maximum droplet volume. I.e. as long as a droplet of that maximum volume will remain on a hydrophilic feature, the hydrophilic feature is configured to support such a droplet.

In an embodiment disclosed herein, the droplet region consists of a pattern of hydrophilic features surrounded by a hydrophobic medium. In this embodiment, the geometry of a hydrophilic feature, the physical/chemical properties of the liquid and the hydrophobic substrate determine the maximum droplet volume, which a single feature is able to retain, such that the liquid does not contact the surrounding hydrophobic medium. One way to experimentally determine the maximum droplet volume would be to deposit increasing amounts of liquid onto an initially dry hydrophilic feature. Liquid deposition could be conducted with the aid of an automated micro-dispenser, or in the case of micron-sized features with the aid of a piezo-actuated micro-manipulator, but should be done in a humidified chamber, such that evaporation cannot take place. Furthermore, with the aid of a microscope, the footprint of the deposited droplet may be measured. Consequently, once the measured footprint transgresses the perimeter defined by the hydrophilic feature the maximum droplet volume has been reached and exceeded.

Apart from the experimental approach, the maximum droplet volume may also be estimated from a simple theoretical model. In this case, it is to be assumed that the hydrophilic feature is circular having a radius of $R_D$, and that the liquid exhibits a contact angle of $\gamma$ when in contact with the hydrophobic medium, and that the droplet rests on a planar surface, see FIGS. 5-6. It is further assumed, that the droplet is sufficiently small such that gravity does not affect the shape of the droplet significantly. When liquid is deposited onto the hydrophilic feature, it will spread out to the perimeter and the liquid will hence form a contact angle $\alpha$. The contact angle $\alpha$ is defined as the angle, the tangent to the droplet surface forms with the planar hydrophilic surface at the perimeter. As the volume of the droplet increases, so does a, but only to a certain point. If $\alpha$ exceeds $\gamma$, it will be energetically more favorable for the droplet to spread onto the hydrophobic medium, thus transgressing the hydrophilic perimeter. Consequently, at the maximum droplet volume $\alpha$ equals $\gamma$, and the volume ($V_D$) may be obtained from the geometrical description of a capped sphere as $$V_D = \pi R_D^3 G(\gamma) \qquad \text{Eqn. 1}$$

$$G(\gamma) = \frac{2 - 3\sin\left(\frac{\pi}{2} - \gamma\right) + \sin^3\left(\frac{\pi}{2} - \gamma\right)}{3\cos^3\left(\frac{\pi}{2} - \gamma\right)}$$

For $\gamma$-values sufficiently close to 90°, Eqn. 1 may be further simplified by assuming the droplet to be a semi-spherical cap, thus exhibiting a $V_D$-value of $2\pi R_D^3/3$.

In yet another case, where the hydrophilic feature is shaped as a circular cavity with radius $R_D$ and depth d, then the maximum volume is found by adding the cavity volume of $\pi dR_D^2$ to Eqn. 1.

In one embodiment, the hydrophilic features are configured to support the nano-to-attoliter droplets and the liquid exhibits a contact angle on the hydrophobic substrate of at least 90 degrees and at most 150 degrees. In one embodiment, the hydrophilic features are configured to support the nano-to-attoliter droplets having a radius ($R_D$) of at least 0.1 µm and at most 100 µm.

Even though a number of approaches can be taken to fabricate an array of hydrophilic features surrounded by a hydrophobic medium, the most readily applicable one would involve photolithography. Photolithography is able to accurately produce micron-sized chemical and/or physical structures, and relies on coating of a flat wafer substrate with a photosensitive thin film. In subsequent steps the thin film is selectively removed by exposure to high-intensity ultraviolet light through a photomask providing the intended pattern.

Sketches of exemplary fabrication processes are provided in FIG. 7. However, due to the optical resolution of UV photolithography, it remains technically challenging to accurately produce features below 0.1 µm. In the case, where the patterned hydrophilic feature is planar circular and exhibits an $R_D$-value of 0.1 µm, the corresponding maximum droplet volume would be $V_D$=2.9 attoliter for a $\gamma$-value of 90° and would be $V_D$=33.1 attoliter for a $\gamma$-value of 150°, according to Eqn. 1.

Hydrophilic features exhibiting $R_D$-values down to 0.1 µm allows for highly dense arrays, which in the context of single molecule digital counting translates into (i) extended dynamic range and (ii) faster detection times.

The extended dynamic range is due to the fact that for digital counting, the number of droplet compartments present in the measurement determines the signal linearity. The signal is considered linear until all droplet compartments produce a signal, i.e. the array has been saturated. For example, a regular rectangular array covering 10 mm×10 mm having a $R_D$-value of 0.1 µm and an inter-feature spacing of 0.4 µm would host 625 million droplets, thus exhibiting a linear dynamic range spanning approximately 8 orders of magnitude.

The faster detection time relies on the fact that for digital counting, the molecular reporter is usually produced by an enzyme or an enzymatically coupled system. In this embodiment, the single enzyme produces a signal by the repeated conversion of a non-fluorescent/-chemiluminescent/-colorimetric molecule into a fluorescing/luminescing/absorbing one (the molecular reporter). The minimum detectable concentration of the reporter molecule depends on the droplet volume; the smaller the volume is, the faster the concentration is reached, assuming a constant enzymatic turnover rate.

On the other hand, droplets exhibiting larger volumes in the nanoliter range (e.g. a circular planar hydrophilic feature with a $R_D$-value of 100 μm has a maximum volume of 2.1 nanoliter for a γ-value of 90° and a maximum volume of 33.1 nanoliter for a γ-value of 150°) would be advantageous in situations, (i) where a large dynamic range is not necessary, e.g. the analyte concentration is expected to be too low to saturate the array or (ii) where sub-nanoliter droplets cannot be resolved by the imaging sensor.

Alternatively, nanoliter volume droplets may be used for arraying and organizing larger biological entities such as cells, cell fragments, virus particles, vesicles, organelles, etc. prior to a measurement.

In one embodiment, the hydrophilic substrate is a glass, a hydrophilic polymer or a metaloxide compound.

The main requirement for the hydrophilic substrate is that the liquid should form a contact angle on it, which is less than for the hydrophobic substrate. Furthermore, the substrate should preferably be amenable to micro-fabrication approaches, such as photolithography, soft lithography or micro-imprinting. Silicondioxide and pure and doped variants thereof is a suitable choice for this purpose, not only because it serves as a well-characterized substrate for photolithography, but also because a great number of chemical and biochemical surface functionalization protocols are available. For example, is a wide range of silane compounds commercially available (e.g. see "Silane coupling agents, version 3.0" as published by Gelest Inc.), which may be used for straightforward derivatization of silicondioxide surfaces. Although silanization is most efficient for materials presenting silanol groups at their surface, such as silicondioxide, many other materials may be amenable to this process. These include but are not limited to aluminum, aluminosilicates, silicon, copper, tin, talc, inorganic oxides (e.g. ferrous oxides, titaniumoxide, chromiumoxide), steel, iron, nickel and zinc.

Upon silane derivatization of a substrate, a new chemical functionality is introduced to the material and hence liquid may exhibit altered contact angles on the substrate after functionalization. For this reason, an initially hydrophilic substrate such as glass might be rendered hydrophobic by functionalization with a hydrophobic silane moiety, e.g. a fluorocarbon silane. Alternatively, an initially slightly hydrophilic substrate might be rendered even more hydrophilic by functionalization with a highly hydrophilic silane moiety, e.g. a poly(ethylene glycol) silane. This is well known to those skilled in the art, and thus the liquid/solid contact angle, which is referred to in this document only relates to the resulting liquid/solid contact angle subsequent to any surface modification of any initial substrate material.

Silane-derivatization of inorganic substrates constitutes only one out of many procedures to introduce new chemical function to a substrate. Another approach includes adsorption of monothiolated compounds to gold substrates, such as to produce a self-assembled monolayer. Yet another approach, which is amenable to soft organic substrates, such as plastics would be plasma polymerization, in which thin layers of a desired chemical polymer is deposited on the plastic surface from a plasma of the corresponding monomers.

The configuration of the hydrophilic features may relate to at least one of:
- the hydrophilicity of the material constituting the hydrophilic feature;
- the hydrophobicity of the material constituting the hydrophobic substrate;
- the area of the feature; and
- the thickness of the feature In one embodiment, the maximum droplet volume is $V_D$ as calculated by Eqn. 1. Accordingly, the hydrophilic features may be provided such that a droplet of this volume can be held at each of the hydrophilic features.

As examples of how to get from the maximum droplet volume to the specific configuration of the individual hydrophilic feature, the following steps may be carried out by
1. First choosing a suitable droplet volume for the application at hand, cf. the aforementioned discussion on droplet volumes.
2. Next, obtain the solid/liquid contact angle γ for the liquid applied in the present application.
3. Next, decide on a desired geometrical shape of the hydrophilic feature, i.e. a circle, a square, a hexagon, etc. The shape is likely to depend on the fabrication procedure applied to produce the pattern.
4. Calculate the relationship between the perimeter length of the particular shape from step 3 and the corresponding maximum droplet volume. In the case of a circular shape, the relationship is provided in Eqn. 1. For other geometrical shapes, the relationship would have to be derived in a similar fashion as that stated for the derivation of Eqn. 1.
5. Obtain the perimeter length corresponding to the chosen droplet volume from the relationship in step 4. In the case of a circular shape, it is sufficient to solve Eqn. 1 for $R_D$.

In a further embodiment, the configuration of the flow compartment in which the pattern of hydrophilic features resides needs to be determined in order to provide a functional gas phase seal to reduce evaporation from the micron-sized droplets. For example, if an attoliter aqueous droplet is deposited on a substrate at ambient conditions, it will evaporate within seconds due to the high surface/volume ratio. Consequently, for applications where droplet contents need to be measured, the droplets are required to be stable for extended periods of time, and hence evaporation should be greatly reduced or completely negated.

In a further embodiment disclosed herein, is a flow compartment hosting a pattern of hydrophilic features, the hydrophilic features configured to support droplets of a certain maximum volume as described above, wherein the flow compartment exhibits a volume $V_C$ and the maximum attainable aggregate volume of a droplet-bearing hydrophilic pattern is denoted $V_{DA}$. If the pattern hosts a number of droplets ($N_D$) each exhibiting the same maximum droplet volume ($V_D$), then $V_{DA}=V_D \cdot N_D$. If the pattern hosts droplets of varying sizes, then the corresponding $V_{DA}$-value is given as $$V_{DA} = \sum_{i=1}^{N_D} V_{D,i} \qquad \text{Eqn. 2}$$

where $V_{D,i}$ is the maximum volume of the i'th droplet on the pattern. Consequently, the corresponding molar amount of liquid ($n_{DA}$) is then $$n_{DA} = \frac{V_{DA} \rho_L}{M_W} \qquad \text{Eqn. 3}$$

where $M_W$ is the molar weight of the liquid and $\rho_L$ is the density of the liquid. If all droplets were to evaporate completely, and assuming the evaporated vapor behaves as an ideal gas, the resulting vapor would produce a corresponding vapor pressure ($P_{VAP}$) in the flow compartment given as $$P_{VAP} = \frac{n_{DA}RT}{V_C} \qquad \text{Eqn. 4}$$

where R is the molar gas constant and T is the temperature. However, complete droplet evaporation is only possible for $V_C \gg V_{DA}$, because in that case the amount of vapor produced by complete droplet evaporation would not change the initial vapor pressure of the flow compartment significantly. However, for a flow compartment volume approaching that of $V_{DA}$, the droplet vapor would increase the pressure in the flow compartment until the saturation vapor pressure ($P_{SAT}$) has become established. Once P SAT has been reached further evaporation is not possible. The $P_{SAT}$-value, i.e. the vapor pressure exerted by the gas-component of the liquid at thermodynamic equilibrium, is given by the Clausius-Clapeyron equation as $$P_{SAT} = P_0 \exp\left(\frac{\Delta H_{VAP}}{R}\left(\frac{1}{T_0} - \frac{1}{T}\right)\right) \qquad \text{Eqn. 5}$$

where $\Delta H_{VAP}$ is the enthalpy of evaporation of the liquid and $P_0$ is a reference vapor pressure of the liquid at a corresponding reference temperature $T_0$.

Consequently, the maximum allowed molar amount of liquid able to evaporate ($n_{VAP}$) can be obtained from the ideal gas equation as $$n_{VAP} = \frac{V_C P_{SAT}}{RT} = \frac{V_C P_0}{RT}\exp\left(\frac{\Delta H_{VAP}}{R}\left(\frac{1}{T_0} - \frac{1}{T}\right)\right) \qquad \text{Eqn. 6}$$

For $n_{VAP} \geq n_{DA}$ complete droplet evaporation takes place. An expression for the maximum flow compartment volume ($V_{MAX}$), i.e. the greatest possible flow compartment volume where droplets are not completely evaporated, may now be obtained as $$n_{VAP}(V_C = V_{MAX}) = \qquad \text{Eqn. 7}$$
$$n_{DA} \Rightarrow V_{MAX} = V_{DA}\frac{\rho_L RT}{M_W P_0}\exp\left(\frac{\Delta H_{VAP}}{R}\left(\frac{1}{T} - \frac{1}{T_0}\right)\right)$$

Consequently, any flow compartment able to host a functional and long-term stable droplet pattern should be configured such that $V_C < V_{MAX}$.

The expression in Eqn. 7 refers to a state of equilibrium. The paths to equilibrium are numerous, but may be described as; (i) a pattern of hydrophilic features are contacted with liquid such as to produce a pattern of droplets, each droplet initially exhibiting the maximum possible volume, (ii) liquid will evaporate from the droplets until the saturation pressure is established in the flow compartment and (iii) the droplets, now having a reduced volume due to the evaporation, remain stable.

Importantly, the pattern needs to be contacted with liquid in a suitable fashion to produce a functional gas phase seal. For example, by actuating a liquid plug across the pattern, thus depositing liquid micro-droplets on the hydrophilic features. Once the liquid plug has contacted all features on the array, the liquid inlet and outlet needs to be blocked such as to provide a closed environment. This may be achieved in a number of ways, for example (i) by having installed valves at the liquid inlet and outlet or (ii) by synchronizing the liquid flow such that the first liquid plug is followed by a second plug, the first one being actuated to the liquid outlet and then stopped, the second being actuated into the liquid inlet, thus blocking inlet and outlet with liquid. In this way, the evaporated liquid from the droplets will establish the saturation pressure in the flow compartment and hence become evaporation resistant. This is exemplified in Examples 1 and 2.

Furthermore, in Eqn. 7 and the following discussion, it was assumed that the gas phase in which the flow system is prepared did not contain any evaporated liquid (i.e. the gas-component of the liquid) prior to contacting the pattern of hydrophilic features with liquid.

However, this may not always be the case. For example, in the case where the liquid is water and the gas phase is atmospheric air, the air may initially contain a certain fraction of water vapor. For atmospheric air, the relative humidity (RH) provides the water vapor pressure relative to the saturation pressure, i.e. RH=$P_W/P_{SAT}$, where $P_W$ is the partial pressure of water vapor in atmospheric air. If the initial relative water vapor saturation of the atmospheric air (RHI) is equal to 0, the air will have no water vapor content and hence Eqn. 7 may be applied. On the other hand, if RHI>0, Eqn. 7 requires modification, because less of the liquid droplet needs to evaporate in order to establish the saturation pressure, thus cf. Eqn. 6

$$n_{VAP} = \qquad \text{Eqn. 8}$$
$$\frac{V_C}{RT}(1-RHI)P_{SAT} = \frac{V_C(1-RHI)P_0}{RT}\exp\left(\frac{\Delta H_{VAP}}{R}\left(\frac{1}{T_0} - \frac{1}{T}\right)\right)$$

This translates into the following solution for $V_{MAX}$:

$$V_{MAX} = V_{DA}\frac{\rho_L RT}{(1-RHI)M_W P_0}\exp\left(\frac{\Delta H_{VAP}}{R}\left(\frac{1}{T} - \frac{1}{T_0}\right)\right) \qquad \text{Eqn. 9}$$

In the present context, RHI is to be understood as general as possible, i.e. thus not only relating to water, but also to any other liquid (see the above section on Definitions). In this case, the more general definition of RHI is RHI=$P_L/P_{SAT}$, where $P_L$ is the initial vapor pressure of the gas component of the liquid applied. The $P_L$-value refers to the gas phase in which the flow system is used prior to the formation of the droplet array. The gas phase seal becomes established once the saturation pressure is reached inside the flow compartment. Thus, locally in the flow compartment, the RH-value will rise from the initial value to 1, indicating complete saturation and a functional gas phase seal.

In one embodiment, the flow compartment disclosed herein has a volume ($V_C$), where the volume ($V_C$) is greater than the aggregate maximum droplet volume ($V_{DA}$) of all liquid nano-to-attoliter droplets and is less than $V_{MAX}$ as calculated in Eqn. 9.

In an embodiment as disclosed herein, to obtain the optimal configuration of a flow system for digital counting of analytes comprising a pattern of hydrophilic features in or on a hydrophobic substrate, it is necessary to consider (i) the configuration of the individual hydrophilic feature, (ii) the configuration of the pattern of the features and (iii) the configuration of the compartment in which the pattern is residing. Collectively, these three configurations provide the flow system with the ability to maintain an evaporation resistant pattern of micro-droplets by way of a gas phase seal. The configuration of the individual hydrophilic feature has been outlined above. Exemplary next steps to determine the flow system configuration is as follows:

1) Decide on the total number of droplets required for the application. As discussed above, the total number of droplets determines the dynamic range of the measurement, and should thus be matched to the expected concentration range of the analyte.
2) The $V_{DA}$-value for the pattern may now be calculated from Eqn. 2, thus providing the lower bound for the flow compartment volume, i.e. the $V_C$-value.
3) Determine the nominal molar weight ($M_W$) and the volume density ($\rho_L$) of the liquid applied, as well as the temperature (T) and RHI-value at which the measurement will take place. Apply a suitable set of values for the reference temperature, pressure and enthalpy of vaporization to calculate the $V_{MAX}$-value for the flow compartment volume using Eqn. 9. For example, is $P_0$=1.0 atm at $T_0$=373 K for water, which exhibits a $\Delta H_{VAP}$-value of 40.7 kJ/mol.
4) Decide on the specific arrangement of the pattern of hydrophilic features, e.g. a square lattice array, a hexagonal lattice array, a rectangular lattice array, a rhombic lattice array, etc. The preferred array geometry will usually be determined by the fabrication method. Decide on the length and width of the array in order to accommodate the total number of droplets.
5) Decide on the flow compartment geometry, e.g. a rectangular channel, a circular channel, a semi-circular channel, etc. The preferred array geometry will usually be determined by the fabrication method.
6) Scale the flow compartment geometry, such that the total volume is less than $V_{MAX}$. An example of this is provided in Example 2. Briefly, in the case of a rectangular channel, the total volume is given as the width×length×height of the channel. The width and length of the channel could for example be matched to that of the array, thus leaving the height variable. The height may thus be chosen to provide a total volume less than $V_{MAX}$.

In a further embodiment disclosed herein, is a flow system wherein the hydrophilic features are circular having a radius ($R_D$), and where the maximum droplet volume ($V_D$) a single hydrophilic circle can support is provided in Eqn. 1.

In an embodiment, the evaporation of each nano-to-attoliter droplet is less than 50 percent, less than 40 percent, less than 30 percent, less than 20 percent, less than 10 percent, less than 5 percent, less than 1 percent of the maximum droplet volume of each nano-to-attoliter droplet.

For a given configuration of the flow system, i.e. a specified set of $V_C$- and $V_{DA}$-values, the corresponding evaporated fraction $\theta_{VAP}$ may be calculated. The evaporated fraction is defined as the droplet volume fraction evaporated into the gas phase, i.e. $\theta_{VAP} = n_{VAP}/n_{DA}$. Inserting Eqn. 3 and Eqn. 8 in to this expression yields $$\theta_{VAP} = \frac{(1-RHI)V_C}{RT}\frac{M_W}{V_{DA}\rho_L}P_{SAT} = \frac{V_C}{V_{DA}}\frac{(1-RHI)M_W P_0}{\rho_L RT}\exp\left(\frac{\Delta H_{VAP}}{R}\left(\frac{1}{T_0}-\frac{1}{T}\right)\right)$$

Eqn. 10

If $\theta_{VAP}$ assumes values greater than 1, then the entire droplet array has evaporated due to e.g. a too large flow compartment volume, too few droplets on the array, a too high temperature, a too small hydrophilic feature, etc. On the other hand, if $\theta_{VAP}$ is less than 1, then the gas phase seal is considered functional, because intact droplets—although exhibiting a reduced volume—may remain on the hydrophilic features.

In principle, any gas known to the skilled person able to seal the droplets against evaporation may be used. Examples of a gas phase seal is atmospheric air, nitrogen, argon or helium or mixes thereof. In one embodiment, the gas phase seal is provided by atmospheric air, nitrogen, argon or helium. In a further embodiment, the gas phase seal is provided by atmospheric air.

In one embodiment, the hydrophobic support having the pattern of hydrophilic features substrate is planar. In a further embodiment, the pattern of hydrophilic features comprises at least one region in which the hydrophilic features are arranged in an array.

In an embodiment, the hydrophilic features are organized in a quadratic planar array, the features being shaped as circles having a radius ($R_D$), the array having a pitch ($\delta$) between neighboring features, where $\delta$ is at least $3R_D$, the array extending a length ($L_{AX}$) along the flow direction, the array extending a length ($L_{AY}$) perpendicular to the flow direction, the channel having a length ($L_{CX}$) along the flow direction, where $L_{CX}$ is greater than or equal to $L_{AX}$, the channel having a length ($L_{CY}$) perpendicular to the flow direction, where $L_{CY}$ is greater than or equal to $L_{AY}$, the channel having a height (h), which is at least $2R_D$ and at most $h_{MAX}$, where $h_{MAX}$ is calculated from the following equation $$h_{MAX} = \theta_{MAX}\frac{L_{AX}L_{AY}}{L_{CX}L_{CY}\delta^2}\frac{\rho_L RT}{(1-RHI)M_W P_0}\exp\left(\frac{\Delta H_{VAP}}{R}\left(\frac{1}{T}-\frac{1}{T_0}\right)\right)V_D(R_D,\gamma)$$

Eqn. 11 where $\theta_{MAX}$ is the maximum acceptable evaporated volume fraction of the droplets and $V_D(R_D, \gamma)$ is the maximum droplet volume according to Eqn. 1. In order to arrive at Eqn. 11, it is necessary to consider Eqn. 10, which expresses the evaporated fraction ($\theta_{VAP}$) as a function of the flow compartment volume ($V_C$) and the maximum aggregate volume of the droplet array ($V_{DA}$). For a flow compartment exhibiting the abovementioned geometry, the flow compartment volume is $V_C=hL_{CX}L_{CY}$ and the maximum aggregate droplet array volume is $V_{DA}=V_D(R_D,\gamma)L_{AX}L_{AY}\delta^{-2}$. One approach to establishing a functional configuration of the flow compartment in order to provide a gas phase seal is to set the maximum acceptable evaporated volume fraction of the droplets to a suitable value, e.g. $\theta_{MAX}=0.05$. Next, by leaving the flow compartment height as the only variable parameter, the maximum allowed height ($h_{MAX}$) may be obtained by inserting $V_C=V_{MAX}=h_{MAX}L_{CX}L_{CY}$, $V_{DA}$ and $\theta_{MAX}$ into Eqn. 10 and solving for $h_{MAX}$, thus arriving at the result in Eqn. 11.

In one embodiment, the pattern of hydrophilic features comprises at least two regions, and the array of one region differs from the array of another region.

In the case where the hydrophilic features are configured to support droplets of various sizes, the calculation of $h_{MAX}$ in Eqn. 11 should be carried out using the $V_D$-value corresponding to the smallest of the droplet volumes on the pattern. In this way, both the smallest and largest droplets on the array may remain stable without evaporating more than set forth by the $\theta_{MAX}$-value.

In one embodiment, the support for the hydrophilic features is located centrally within the flow compartment.

Even though a central location in the flow compartment of the array comprising the hydrophilic features would usually be the preferred, the exact location of the array does not influence the results of the previous calculations. This is due to the calculations are based on the assumption that thermodynamic equilibrium becomes established within the flow compartment, i.e. an equilibrium where the evaporation rate from the liquid droplets supported by the hydrophilic features equals the condensation rate of the vapor in the flow compartment onto the droplets. However, a centrally located array may reach equilibrium faster compared to a decentrally located one due to the transport kinetics of vapor within the compartment.

In one embodiment, the number of hydrophilic features is at least 1,000, at least 10,000, at least 100,000, at least 1,000,000, at least 10,000,000.

In one embodiment, the hydrophobic layer is a molecular monolayer covalently grafted to the substrate. In one embodiment, the hydrophobic layer is a molecular monolayer chemisorbed on a metal substrate.

In one embodiment, the flow compartment is channel shaped and forms a flow direction between two openings in opposite ends of the flow compartment. In one embodiment, the flow compartment and the openings have a rectangular shape in a cross section perpendicular to the flow direction. In one embodiment, the flow compartment has a rectangular shape and the openings have a circular shape in a cross section perpendicular to the flow direction.

In one aspect disclosed herein is a method of preparing a flow system.

To provide an overall understanding of the invention, certain illustrative embodiments will now be described, including a system that supports an array of microdroplets to allow sELISA analysis of an enzyme. However, it will be understood by one of ordinary skill in the art that the systems and methods described herein can be adapted and modified for other suitable applications and that such other additions and modifications will not depart from the scope hereof.

Figure 1:
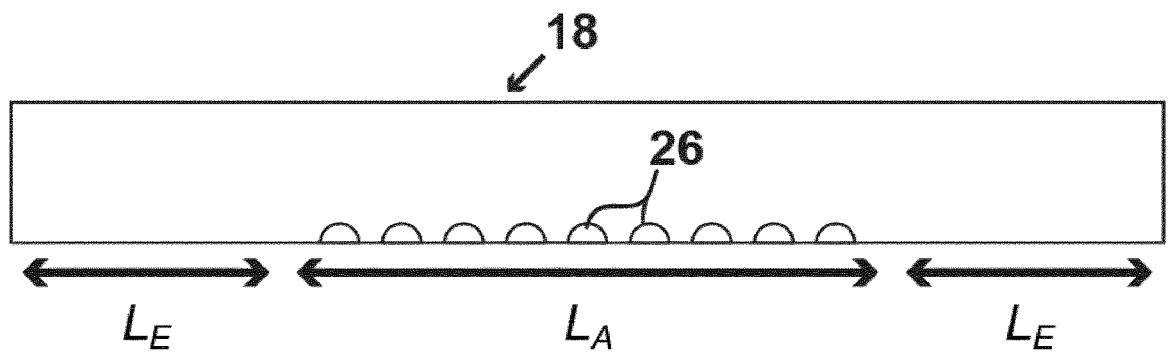
FIG. 1 depicts one example of a flow compartment 18 having a plurality of microdroplets 26. The sketch is not drawn to scale.

FIG. 1 depicts one embodiment of a system for supporting a plurality of microdroplets with reduced rate of evaporation. Specifically, FIG. 1 illustrates a system 18 wherein a rectangular flow compartment houses a plurality of microdroplets. The microdroplets are placed on a bottom surface of the flow compartment. Each end of the flow compartment is open to the ambient environment.

Figure 2:
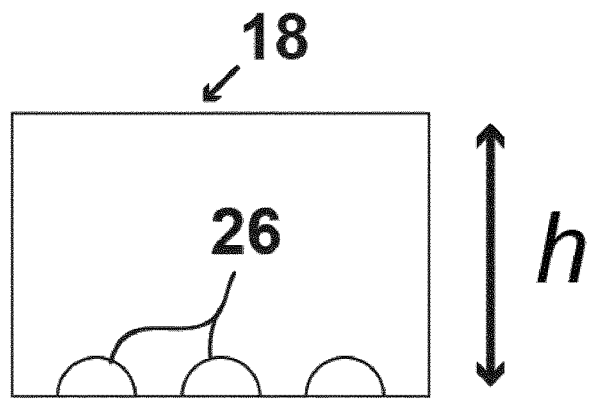
FIG. 2 depicts one example of an end of the flow compartment 18 in FIG. 1. The sketch is not drawn to scale.

FIG. 2 is a cross-sectional view of an end of the flow compartment. FIG. 2 shows that for this embodiment the end is square in shape of height h (depicted by the vertical arrow). Returning to FIG. 1, it is shown that each end of the array of microdroplets is spaced a distance $L_E$ (illustrated by the double arrow) from the end of the flow compartment.

The flow compartment of FIG. 1 is a flowchannel that supports an array of microdroplets. The microdroplets may be inserted into the flowchannel using any known technique. The dimensions of the depicted flowchannel can be generally understood from FIG. 1 and are characterized by the height h, of the channel, $L_A$, which is the length of the flowchannel covered by the array of microdroplets, $L_E$, which is the length of the channel that separates the microarray from the inlet and the outlet (and not supporting any portion of the array of microdroplets). Given the length and height and shape of the flowchannel, it is possible to calculate the volume of that flow channel. Details of one such calculation are set out in Example 2.

Each droplet is essentially a hemisphere and can be modeled as such. The hemispherical droplet will have a radius. The drops are spaced apart essentially a standard pitch. The dots may be in a linear array, a square array, or any other suitable arrangement. It is of course possible to estimate the total aggregate volume of liquid contained in the array of microdroplets as a function of the radius and the number of droplets. Details of one such calculation are set out in Example 2.

Figure 3:
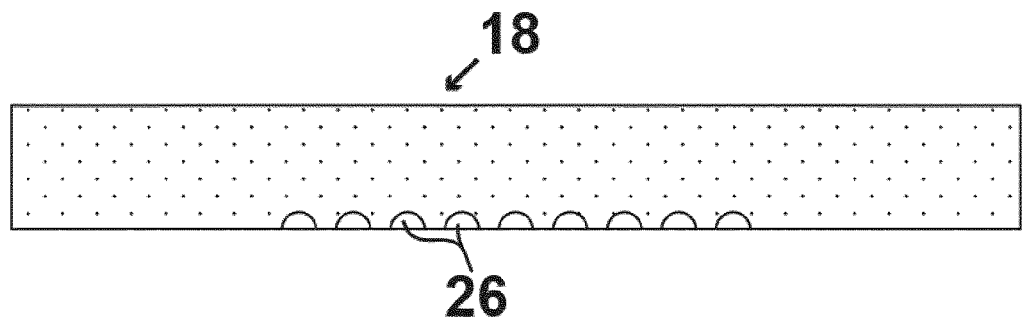
FIG. 3 depicts an exemplary representation of a flow compartment 18 with a vapor phase forming a gas seal. The sketch is not drawn to scale.

Once the geometry of the flowchannel is known, the available volume can be calculated. The volume and the equilibrium water vapor pressure ($P_W$) determines the amount of water, which will evaporate, as stated by the Clausius-Clapeyron equation. Details of one such calculation are set out in Example 2. Because the vapor pressure is generated by the evaporated water from the droplets, it thus humidifies and saturates the air in the flowchannel. Consequently, if only a small fraction of the aggregate droplet volume is sufficient to establish the equilibrium vapor pressure, then the remaining water volume will be preserved on the surface as droplets. In this way, the humidified air provides a gas-phase seal as shown in FIG. 3 (shown by the dotted filling surrounding the microdroplets).

By selecting, for example, a particular height, h, for a certain volume of solution, the amount of evaporated water can be held at about 5%, as shown in FIG. 11B.

The process by which a gas-phase seal is established is shown on a micrograph in FIG. 4. Here, a plug of water is actuated from one end of the flowchannel to the other, leaving behind well-defined micron-sized aqueous droplets. The receding water-front can be seen on the left side of the micrograph, and the array of droplets can be seen to the right of the water-front. The black arrow indicates the direction in which the liquid is being actuated.

Applications

The invention described here has many possible applications, which are known to those skilled in the art, e.g. see Witters et al. in Digital Biology and Chemistry (DOI: 10.1039/C4LC00248B, (Frontier) Lab on a Chip, 2014, 14, pp. 3225-3232). These include a class of assays, which we term single enzyme-linked molecular analysis (SELMA). SELMA-based assays rely on manipulation and detection of single peptide, protein and/or oligonucleotide molecules.

In one aspect, the flow system as disclosed herein may be used in a method of digital counting of at least one or more distinct analyte types.

A SELMA-based measurement is a digital counting assay in which the analytes become immobilized inside gas phase sealed droplets, and where the analytes subsequently in one or more steps undergo labeling with an enzyme-conjugated agent. Due to the nano-to-attoliter volume of the droplets, a single enzyme is able to produce a detectable optical signal within seconds-to-minutes by continuous enzymatic conversion of a detection agent. In FIG. 9 a sketch on an exemplary SELMA-based measurement is provided and in Example 4 an experimental demonstration of SELMA is described.

In one aspect disclosed herein is a method for digital counting of at least one or more distinct analyte types, the method comprising counting the analyte types contained in a plurality of liquid nano-to-attoliter droplets under a gas phase seal.

In an embodiment as disclosed herein, the gas phase seal establishes a vapor pressure within the flow compartment capable of reducing evaporation of the microdroplets.

In an embodiment as disclosed herein, the digital counting is performed in a flow system, which flow system comprises a support having a pattern of hydrophilic features in or on a hydrophobic substrate, the hydrophobic substrate being embedded in a flow compartment comprising at least one opening, the hydrophilic features configured to support the plurality of liquid nano-to-attoliter droplets.

In an embodiment as disclosed herein, the hydrophilic features are circular having a radius ($R_D$), and where the maximum droplet volume ($V_D$) a single hydrophilic circle can support is $$V_D = \pi R_D^3 G(\gamma)$$

$$G(\gamma) = \frac{2\text{-}3\sin(\frac{\pi}{2}-\gamma) + \sin^3(\frac{\pi}{2}-\gamma)}{3\cos^3(\frac{\pi}{2}-\gamma)}$$

where $\gamma$ is the liquid contact angle on the hydrophobic substrate.

In an embodiment as disclosed herein, the gas phase seal reduces evaporation of each nano-to-attoliter droplet to less than 50 percent of the maximum droplet volume.

In an embodiment as disclosed herein, the flow system as described herein is used in the method disclosed herein.

Those skilled in the art will know or be able to ascertain using no more than routine experimentation, many equivalents to the embodiments and practices described herein.

Accordingly, it will be understood that the invention is not to be limited to the embodiments disclosed herein, but is to be understood from the following claims, which are to be interpreted as broadly as allowed under the law.

In particular, the invention relates to the following numbered items:

Numbered item 1. A method for digital counting analysis of a sample potentially containing at least one analyte, wherein the sample has been contacted with a solid phase having a plurality of discrete capture sites, each site being capable of capturing the at least one analyte, which method comprises at least two detection cycles, where each detection cycle comprises the steps of
 a) triggering a signal from captured and labelled analyte(s),
 b) recordation of the number and positions of capture sites exhibiting a signal from the captured and labelled analyte(s),
 c) and before a further detection cycle is performed, deactivation of signal(s).

Numbered item 2. The method according to numbered item 1, wherein the sample and the solid phase having a plurality of discrete capture sites are compartmentalized prior to or during capturing of the at least one analyte.

Numbered item 3. The method according to numbered item 1, wherein the captured analyte(s) and labelling agent are compartmentalized prior to or during labelling of the at least one analyte.

Numbered item 4. The method according to any one of numbered items 1-3, wherein the analyte(s) is labelled by adding a labelling agent in a labelling step in each detection cycle before step a).

Numbered item 5. The method according to any one of numbered items 1-4, wherein the captured analyte(s) is labelled by adding a labelling agent in a labelling step prior to or during capturing of the analyte(s) on the solid phase, and wherein step c) before a further detection cycle is performed is followed by a re-labelling step, wherein the captured analyte(s) is labelled by adding a labelling agent.

Numbered item 6. The method according to any one of numbered items 1-5, wherein the captured and labelled analyte(s) is compartmentalized to produce liquid compartments containing at least one analyte.

Numbered item 7. A method for digital counting analysis of a sample potentially containing at least one analyte, wherein the sample has been contacted with a solid phase having a plurality of discrete capture sites, each site being capable of capturing the at least one analyte, which method comprises at least two detection cycles, where each detection cycle comprises the steps of labelling the at least one analyte by adding a labelling agent and compartmentalize the at least one captured and labelled analyte to produce liquid compartments containing at least one analyte followed by steps a)-c):
 a) triggering a signal from the captured and labelled analyte(s),
 b) recordation of the number and positions of capture sites exhibiting a signal from the captured and labelled analyte(s),
 c) and before a further detection cycle is performed, deactivation of signal(s).

Numbered item 8. A method for digital counting analysis of a sample potentially containing at least one analyte, wherein the sample has been contacted with a solid phase having a plurality of discrete capture sites, each site being capable of capturing the at least one analyte, wherein the at least one analyte is labelled by adding a labelling agent in a labelling step prior to or during capture of the at least one analyte on the solid phase, which method comprises at least two detection cycles, wherein the at least one captured and labelled analyte is compartmentalized to produce liquid compartments containing at least one analyte followed by steps a)-c):
 a) triggering a signal from the captured and labelled analyte(s),
 b) recordation of the number and positions of capture sites exhibiting a signal from the captured and labelled analyte(s),
 c) and before a further detection cycle is performed, deactivation of signal(s),
wherein step c) before a further detection cycle is performed is followed by a re-labelling step, wherein the at least one captured analyte is labelled by adding a labelling agent.

Numbered item 9. The method according to any of the previous numbered items, wherein the analysis is a single molecule digital counting analysis.

Numbered item 10. The method according to any of the previous numbered items for reduction of false-positive detections and/or background noise in single molecule digital counting analysis of a sample.

Numbered item 11. The method according to any of the previous numbered items, where the sample contains or potentially contains a target analyte and a non-target compound, where the target analyte is captured by the capture site with capture efficiency $C_1$, where the non-target compound is captured by the capture site with capture efficiency $C_2$ and $C_1 \geq C_2$, where the target analyte is labelled by a first labelling agent with labelling efficiency $L_1$, where the non-target compound is labelled by the first labelling agent with labelling efficiency $L_2$ and $L_1 \geq L_2$, where the number of detection cycles $N_C$ is adjusted such that the ratio $\alpha = C_1 N_1^{N_C}/C_2 N_2^{N_C}$ is between 1-10, preferably between 10-100, preferably between 100-1000, preferably between 1,000-10,000, preferably between 10,000-100,000, preferably greater than 100,000, and where each detection cycle applies the first labelling agent in the labelling step.

Numbered item 12. The method according to numbered item 11, which includes a false-positive detection cycle, where a second labelling agent is applied instead of the first labelling agent in the labelling step, where the non-target compound is labelled by the second labelling agent with labelling efficiency $L_1$, where the target analyte is labelled by the second labelling agent with labelling efficiency $L_2$ and $L_1 \geq L_2$.

Numbered item 13. The method according to numbered item 12, where the number of non-target compounds present in the sample is estimated from the number of capture sites exhibiting a signal in the false-positive detection cycle.

Numbered item 14. The method according to numbered item 13, where the number of target analytes present in the sample is estimated from the number of capture sites repeatedly exhibiting a signal in all detection cycles prior to the false-positive detection cycle and from the estimated number of non-target compounds present in the sample.

Numbered item 15. The method according to any one of the previous numbered items, wherein at most 99%, such as at most 95%, such as at most 90%, such as at most 85%, such as at most 80%, such as at most 75%, such as at most 70%, such as at most 65% of the liquid compartments contain captured and labelled analyte.

Numbered item 16. The method according to any one of the previous numbered items, which includes a false-positive detection cycle, wherein the method does not comprise any labelling steps.

Numbered item 17. The method according to any one of the previous numbered items, wherein the labelling agent comprises a detection modality, and where the step of triggering a signal(s) is by delivering detection agents to the detection modality.

Numbered item 18. The method according to any one of the previous numbered items, wherein the detection cycle comprises the step of subsequently removing labelling agents that has not labelled the analyte before triggering a signal from the at least one captured and labelled analyte.

Numbered item 19. The method according to any one of the previous numbered items, where non-bound sample components are removed from the captured analyte or the captured and labelled analyte.

Numbered item 20. The method according to any one of the previous numbered items, wherein the step of deactivation of signal(s) is selected from
  a) detaching the labelling agent from the captured analyte,
  b) deactivating the ability of the labelling agent to facilitate a signal or
  c) the combination of a) and b),
and wherein the step of deactivation of signal(s) is optionally followed by a rinsing step.

Numbered item 21. The method according to any one of the previous numbered items, wherein the capturing of the at least one analyte from the sample is by immobilization on the solid phase.

Numbered item 22. The method according to any one of the previous numbered items, wherein the capturing of the at least one analyte from the sample is by using one or more capture probes specific to the analyte and where the capture probes are attached to the solid phase.

Numbered item 23. The method according to any one of the previous numbered items, where a first number and a second number of detection cycles are used, and where the first number of detection cycles uses labelling agents differing from the second number of detection cycles.

Numbered item 24. The method according to any one of the previous numbered items, wherein one or more different capture probes for one or more distinct analyte types are attached to the solid phase.

Numbered item 25. The method according to any one of the previous numbered items, wherein one or more different labelling agents are used to label one or more distinct analyte types.

Numbered item 26. The method according to any one of the previous numbered items, where the number of detection cycles is at least 3 cycles, at least 4 cycles, at least 5 cycles, at least 6 cycles, at least 7 cycles, at least 8 cycles, at least 9 cycles, or at least 10 cycles.

Numbered item 27. The method according to any one of the previous numbered items, where the number of detection cycles is between 3-20 cycles, between 3-15 cycles, between 3-10 cycles, between 3-9 cycles, between 3-8 cycles, between 3-7 cycles, between 3-6 cycles, or between 3-5 cycles.

Numbered item 28. The method according to any one of the previous numbered items, wherein the labeling agent is deactivated by detachment from the captured analyte and removed by flushing.

Numbered item 29. The method according to any one of the previous numbered items, wherein the step of deactivating the signals is conducted in the plurality of liquid compartments.

Numbered item 30. The method according to any one of the previous numbered items, wherein the labeling agent is deactivated by detachment from the captured analyte and where the detachment is by enzymatic cleavage.

Numbered item 31. The method according to any one of the previous numbered items, wherein the labeling agent is deactivated by detachment from the captured analyte and where the detachment is by chemical cleavage or desorption by adjusting the pH, adjusting the ionic strength, adding denaturing salts or adding detergents.

Numbered item 32. The method according to any one of the previous numbered items, wherein the labeling agent is deactivated by detachment from the captured analyte and where the detachment is by heating.

Numbered item 33. The method according to any one of the previous numbered items, wherein the labeling agent is deactivated by changing its chemical or physical state.

Numbered item 34. The method according to any one of the previous numbered items, wherein the labeling agent comprises an enzyme and wherein the state of the enzyme is changed by chemical or biochemical modification of the active site.

Numbered item 35. The method according to any one of the previous numbered items, wherein the labeling agent comprises an enzyme and wherein the state of the enzyme is changed by chemical or physical disruption of the tertiary structure of the enzyme.

Numbered item 36. The method according to any one of the previous numbered items, wherein the captured and labelled analyte is compartmentalized to produce liquid compartments hosting the captured and labelled analyte by introducing and withdrawing a hydrophilic liquid on the plurality of discrete capture sites, where each discrete capture site is rendered hydrophilic and where the plurality of discrete capture sites is placed on a hydrophobic substrate, such that upon withdrawing of the hydrophilic liquid a plurality of liquid droplets is formed and each droplet occupies one discrete capture site.

Numbered item 37. The method according to any one of the previous numbered items, wherein the captured and labelled analyte is compartmentalized to produce liquid compartments hosting analyte by introducing a first hydrophilic liquid on the plurality of discrete capture sites followed by displacing the first hydrophilic liquid with a second liquid, where the two liquids are immiscible and where the second liquid is lighter than the first, and where each discrete capture site is rendered hydrophilic, and the plurality of discrete capture sites is placed on a hydrophobic substrate, such that upon displacement of the first hydrophilic liquid with the second liquid, a plurality of liquid droplets comprising the first hydrophilic liquid is formed and each droplet occupies one discrete capture site.

Numbered item 38. The method according to any one of the previous numbered items, wherein captured and labelled analyte is compartmentalized to produce liquid compartments hosting analyte by introducing a first liquid to the plurality of discrete capture sites, where each discrete capture site is well-shaped or capillary-shaped, and where the first liquid is displaced by a second liquid, where the two liquids are immiscible and where the second liquid is lighter than the first, such that upon displacement of the first liquid, a plurality of liquid droplets comprising the first liquid is formed and each droplet occupies one discrete capture site.

Numbered item 39. The method according to any one of the previous numbered items, wherein the captured and labelled analyte is compartmentalized to produce liquid compartments hosting analyte by introducing a liquid to the plurality of discrete capture sites, where each discrete capture site is well-shaped or capillary-shaped, and where the liquid is dispensed into the discrete capture site, such that each liquid compartment occupies one discrete capture site.

Numbered item 40. The method according to any one of the previous numbered items, wherein the captured and labelled analyte is compartmentalized to produce liquid compartments hosting analyte by introducing a liquid to the plurality of discrete capture sites, where each discrete capture site is well-shaped, and where the liquid is displaced by applying a lid on the plurality of capture sites, such that a plurality of liquid droplets is formed and each droplet occupies one well-shaped capture site bounded by the lid.

Numbered item 41. The method according to any one of the previous numbered items, wherein the captured and labelled analyte is compartmentalized to produce liquid compartments hosting the captured and labelled analyte by introducing a first liquid containing the plurality of discrete capture sites and the captured and the labelled analyte to a second liquid, where the second liquid is immiscible with the first liquid, such that a plurality of emulsion droplets consisting of the first liquid and enclosed by the second liquid is formed, and where each emulsion droplet contains at least one discrete capture site and at least one captured and labelled analyte.

Numbered item 42. The method according to any one of the previous numbered items, wherein the positions of liquid compartments exhibiting a signal in each detection cycle are compared to the positions of liquid compartments exhibiting a signal in the other detection cycles, such that the number of consecutive detection cycles a liquid compartment exhibits a signal is counted, and where liquid compartments are classified in at least two categories, the first category of liquid compartments exhibiting a greater count than the second category.

Numbered item 43. The method according to numbered item 42, wherein the number of liquid compartments repeatedly exhibiting a signal in consecutive detection cycles is applied to calculate the concentration of target analytes in the sample.

Numbered item 44. The method according to any of the previous numbered items, where the number of discrete capture sites is at least 1,000, preferably at least 10,000, preferably at least 100,000, preferably at least 1,000,000, preferably at least 10,000,000.

Numbered item 45. The method according to any of the previous numbered items, where the discrete capture sites are circular or spherical and where the diameter of the individual discrete site is less than 1 mm, preferably less than 100 µm, preferably less than 10 µm, preferably less than 1 µm.

Numbered item 46. The method according to any of the previous numbered items, where the discrete capture sites are circular or spherical and where the diameter of the discrete sites is between 0.5-5 µm, between 0.5-10 µm, between 0.5-50 µm, between 0.5-100 µm, between 10-1000 µm, between 50-1000 µm, between 100-1000 µm.

Numbered item 47. The method according to any of the previous numbered items, where the discrete capture sites are quadratic and where the length of the individual discrete site is less than 1 mm, preferably less than 100 µm, preferably less than 10 µm, preferably less than 1 µm.

Numbered item 48. The method according to any of the previous numbered items, where the discrete capture sites are quadratic and where the length of the discrete sites is between 0.5-5 µm, between 0.5-10 µm, between 0.5-50 µm, between 0.5-100 µm, between 10-1000 µm, between 50-1000 µm, between 100-1000 µm.

Numbered item 49. The method according to any of the previous numbered items, where the solid phase is
  a) a solid substrate,
  b) a colloid bead, or
  c) a collection of colloid beads.

Numbered item 50. The method according to any one of the previous numbered items, wherein the liquid compartments are in the form of a plurality of liquid nano-to-attoliter droplets under a gas phase seal.

Numbered item 51. The method according to any one of the previous numbered items, wherein the liquid compartments occupy well-shaped capture sites, cavity-shaped capture sites or capillary-shaped capture sites.

Numbered item 52. The method according to any one the previous numbered items, wherein the liquid compartments are in the form of a plurality of water-in-oil emulsion droplets.

Numbered item 53. The method according to any one the previous numbered items, wherein the liquid compartments are in the form of a plurality of liquid nano-to-attoliter droplets under a water-immiscible liquid phase.

Numbered item 54. The method according to any one of the previous numbered items, wherein the digital counting is performed in a flow system (10) for digital counting of one or more analyte types in a sample, the flow system comprising a support (12) having a pattern of hydrophilic features (14) in or on a hydrophobic substrate (16), the hydrophobic substrate (16) being embedded in a flow compartment (18) comprising at least one opening (20), the hydrophilic features (14) configured to support a plurality of liquid nano-to-attoliter droplets each having a maximum droplet volume, and the flow compartment (18) configured to support a gas phase seal reducing evaporation of each nano-to-attoliter droplet.

Numbered item 55. The method according to numbered item 54, wherein the gas phase seal establishes a vapor pressure within the flow system capable of reducing evaporation of the microdroplets.

Numbered item 56. The method according to any one of numbered items 54-55, wherein the gas phase seal reduces evaporation of each nano-to-attoliter droplet to less than 50 percent of the maximum droplet volume.

Numbered item 57. The method according to any one of numbered items 54-56, comprising the step of (i) contacting a pattern of hydrophilic features (14) in or on the hydrophobic substrate (16) with a sample containing the one or more analyte types.

Numbered item 58. The method according to any one of numbered items 54-57, comprising the step of (ii) capturing the one or more analyte types on the hydrophilic features (14).

Numbered item 59. The method according to any one of numbered items 54-58, comprising the step of (iii) labeling the at least one captured analyte type with a labeling agent specific to the analyte type to be detected.

Numbered item 60. The method according to any one of numbered items 54-59, wherein the captured and labelled analyte is compartmentalized to produce liquid compartments hosting at least one analyte by step (iv) flowing across and withdrawing from the pattern a detection agent to produce the individual droplets in the form of nano-to-attoliter droplets.

Numbered item 61. The method according to any one of numbered items 54-60, comprising the step of (v) counting the number of the droplets hosting both the labeling and detection agent.

Numbered item 62. The method according to any one of numbered items 54-61, comprising repeating steps (iii), (iv) and (v) one or more times.

Numbered item 63. The method according to any one of numbered items 54-62, comprising repeating steps (iii), (iv) and (v) by using, instead of the first labeling agent, a second labeling agent specific to a second analyte type to be detected.

Numbered item 64. The method according to any one of numbered items 54-63, comprising a step of deactivating the labeling agents present in the previous step before repeating steps (iii), (iv) and (v).

Numbered item 65. The method according to any one of numbered items 54-64, wherein the labeling agent is deactivated by detachment from the captured analyte and removed by flushing of the flow system.

Numbered item 66. The method according to any one of the previous numbered items, wherein the labeling agent comprises an enzyme and a specific analyte recognition moiety, and the analyte recognition moiety is chosen from the following group of molecules: oligonucleotides, proteins, peptides, aptamers, antibodies, complexes thereof or synthetic variants thereof.

Numbered item 67. The method according to any one of the previous numbered items, wherein the discrete capture site is the hydrophilic feature.

Numbered item 68. The method according to any one of the previous numbered items, wherein one or more capture probes (22) for one or more distinct analyte types are attached to the hydrophilic features (14).

Numbered item 69. The method according to any one of the previous numbered items, comprising more than one type of capture probe (22) attached to the hydrophilic features (14), and wherein the different types of capture probes (22) are arranged in regions (24).

Numbered item 70. The method according to any one of the previous numbered items, wherein the capture probes (22) are selected from the following group of probes: oligonucleotides, aptamers, proteins, antibodies, peptides or synthetic variants thereof.

Numbered item 71. The method according to any one of the previous numbered items, wherein the sample containing the one or more analyte types in a liquid is contacted with the substrate containing the hydrophilic features (14) by full immersion.

Numbered item 72. The method according to any one of the previous numbered items, wherein the labelling is performed by bringing a solution containing a labelling agent for the analyte in contact with the captured analyte by full immersion.

Numbered item 73. The method according to any one of the previous numbered items, wherein the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

Numbered item 74. The method according to any one of the previous numbered items, wherein the sample is selected from the following group of samples: blood, plasma, serum, urine, saliva, cerebrospinal fluid, tears fluid, or tissue.

Numbered item 75. The method according to any one of the previous numbered items, wherein the sample is selected from laboratory-processed samples of the following sample group: blood, plasma, serum, urine, saliva, cerebrospinal fluid, tears fluid or tissue.

Numbered item 76. The method according to any one of the previous numbered items, wherein the digital counting analysis involves both single-molecule detection and quantification.

Numbered item 77. The method according to any one of the previous numbered items, wherein the captured analytes become covalently coupled to the capture probe(s) (22) subsequent to capture.

Numbered item 78. The method according to any one of the previous numbered items, wherein the capture probe is an oligonucleotide or a synthetic oligonucleotide, the analyte is an oligonucleotide or a molecular complex containing oligonucleotides, where the analyte is bound to the capture probe via a sequence complementary to the capture probe sequence and where the covalent crosslinking is carried out by using an interstrand crosslinking agent such as platinum complexes, mitomycin C, nitrogen mustards, psoralens or aldehydes.

Numbered item 79. The method according to any one of the previous numbered items, wherein the capture probe is a protein, an aptamer, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide, methylglyoxal or uranyl acetate.

Numbered item 80. The method according to any of the previous numbered items, where the capture probe is a synthetic oligonucleotide, where the synthetic modification incorporates a chemical group reactive towards the analyte such that covalent linkage can be established between analyte and capture probe subsequent to capture.

Numbered item 81. The method according to numbered item 80, where the covalent linkage between analyte and capture probe is triggered by contacting the analyte/capture probe-complex with a chemical agent.

Numbered item 82. The method according to numbered item 80, where the covalent linkage between analyte and capture probe is triggered by contacting the analyte/capture probe-complex with electromagnetic radiation.

Numbered item 83. The method according to any one of the previous numbered items, wherein the digital counting measurement comprises a single-enzyme linked molecular analysis (SELMA), digital polymerase chain reaction (dPCR), single enzyme-linked immunosorbent assay (sELISA) or digital single-enzyme linked immunosorbent assay (dELISA).

Numbered item 84. The method according to any one of the previous numbered items, wherein the at least one analyte is an oligonucleotide, where the sequence of the oligonucleotide is a genomic sequence or a transcribed genomic sequence having one or more base-pair changes such as single nucleotide polymorphisms, insertions or deletions, and where the sample potentially contains more than one non-target oligonucleotide(s), the non-target oligonucleotide(s) having the same genomic sequence or transcribed genomic sequence as the target, but without the one or more base-pair changes.

Numbered item 85. The method according to any one of the previous numbered items, wherein the sample contain a first and a second analyte type, where the first analyte type has a first sequence and a first concentration in the sample, where the second analyte type has a second sequence and a second concentration in the sample, where the first and the second sequence are different, where the first and the second sequence are genomic sequences or transcribed genomic sequences, and where according to any of the previous numbered items the first and the second concentration is measured and compared to each other to identify copy number variations.

Numbered item 86. The method according to any one of the previous numbered items, wherein the gas phase is provided by atmospheric air, and wherein the capture probes are selected from the group of single-stranded DNA oligos, single-stranded locked nucleic acid oligos or single-stranded peptide nucleic acid oligos, where different types of capture probes are arranged in regions, where the analytes are single-stranded DNA extracted from a processed blood sample, where the labelling agent comprises a detection modality and a recognition moiety, where the detection modality is an enzyme and the recognition moiety is selected from the group of single-stranded DNA oligo, a single-stranded locked nucleic acid oligo or a single-stranded peptide nucleic acid oligo.

Numbered item 87. Use of a solid phase having a plurality of discrete capture sites, each site being capable of capturing the at least one analyte in a method according to any one of the preceding numbered items.

Numbered item 88. Use of a solid phase having a plurality of discrete capture sites, each site being capable of capturing the at least one analyte in a method according to any one of the preceding numbered items for reducing counting error in a digital counting analysis such as reduction of false-positive detections and/or reducing background noise.

Numbered item 89. Use of a solid phase having a plurality of discrete capture sites, each site being capable of capturing the at least one analyte for reducing counting error such as reduction of false-positive detections and/or reducing background noise in a digital counting analysis by performing at least two detection cycles as defined in any one of numbered items 1-86.

Further Specific Embodiments of the Invention

A process for holding microdroplets of a picoliter or less in volume in place on a substrate and in the liquid phase, comprising, placing the microdroplets within a channel having at least one opening, setting the volume of the channel to a value that establishes a vapor pressure within the channel capable of reducing evaporation of the microdroplets.

The invention further relates to the following embodiments:

Embodiment 1

A flow system for digital counting of one or more analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets each having a maximum droplet volume, and the flow compartment configured to support a gas phase seal reducing evaporation of each nano-to-attoliter droplet.

Embodiment 2

The flow system according to embodiment 1, wherein the flow compartment has a volume ($V_C$), where the volume ($V_C$) is greater than the aggregate maximum droplet volume ($V_{DA}$) of all liquid nano-to-attoliter droplets and is less than $V_{MAX}$ calculated by the following equation:

$$V_{MAX} = V_{DA} \frac{\rho_L RT}{(1-RHI)M_W P_0} \exp\left(\frac{\Delta H_{VAP}}{R}\left(\frac{1}{T} - \frac{1}{T_0}\right)\right)$$

where $\rho_L$ is the volume density of the liquid, R is the molar gas constant, T is the temperature, RHI is the initial relative vapor saturation of the gas component of the liquid, $P_0$ is a reference vapor pressure of the liquid at a corresponding reference temperature $T_0$, $M_W$ is the molar weight of the liquid and $\Delta H_{VAP}$ is the enthalpy of evaporation of the liquid.

Embodiment 3

The flow system according to any one of embodiments 1-2, wherein the hydrophilic features are circular having a radius ($R_D$), and where the maximum droplet volume ($V_D$) a single hydrophilic circle can support is $$V_D = \pi R_D^3 G(\gamma)$$

$$G(\gamma) = \frac{2 - 3\sin\left(\frac{\pi}{2} - \gamma\right) + \sin^3\left(\frac{\pi}{2} - \gamma\right)}{3\cos^3\left(\frac{\pi}{2} - \gamma\right)}$$

where $\gamma$ is the liquid contact angle on the hydrophobic substrate.

Embodiment 4

The flow system according to any one of the preceding embodiments, wherein the evaporation of each nano-to-attoliter droplet is less than 50 percent of the maximum droplet volume, less than 40 percent, preferably less than 30 percent, preferably less than 20 percent, preferably less than 10 percent, preferably less than 5 percent, preferably less than 1 percent of the maximum droplet volume of each nano-to-attoliter droplet.

Embodiment 5

The flow system according to any one of the preceding embodiments, wherein the gas phase seal is comprised by atmospheric air, nitrogen, argon and/or helium.

Embodiment 6

The flow system according to any one of the preceding embodiments, wherein the gas phase seal is comprised by atmospheric air.

Embodiment 7

A flow system for digital counting of one or more distinct analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets.

Embodiment 8

The flow system according to any one of the preceding embodiments comprising one or more flow compartments overlaying the droplet region to enable liquid contact to the hydrophilic/hydrophobic pattern.

Embodiment 9

The flow system according to any one of the preceding embodiments comprising one or more liquid loading pads for supplying the flow system with liquids and reagents.

Embodiment 10

The flow system according to any one of the preceding embodiments comprising a liquid inlet connecting the flow compartment(s) to the liquid loading pad(s).

Embodiment 11

The flow system according to any one of the preceding embodiments, where liquid is actuated across the flow channel by means of a pressure drop from the inlet to the outlet

Embodiment 12

The flow system according to any one of the preceding embodiments comprising a liquid outlet connecting the flow channel to a pressure source to provide suction, and hence mediate liquid actuation through the flow channel.

Embodiment 13

The flow system according to any one of the preceding embodiments, wherein the gas phase seal is comprised by atmospheric air, nitrogen, argon and/or helium.

Embodiment 14

The flow system according to any one of the preceding embodiments, wherein the gas phase is comprised by atmospheric air.

Embodiment 15

The flow system according to any one of the preceding embodiments, comprising at least one capture probe for one or more distinct analyte types, the capture probe(s) being attached to the hydrophilic features.

Embodiment 16

The flow system according to anyone of the preceding embodiments, wherein different types of capture probe(s) are arranged in regions.

Embodiment 17

The flow system according to anyone of the preceding embodiments, wherein the support is planar.

Embodiment 18

The flow system according to any one of the preceding embodiments, wherein the hydrophilic feature(s) is planar.

Embodiment 19

The flow system according to anyone of the preceding embodiments, wherein the pattern of hydrophilic features comprises at least one region in which the hydrophilic features are arranged in an array.

Embodiment 20

The flow system according to anyone of the preceding embodiments, wherein the hydrophilic features are organized in a quadratic planar array, the features being shaped as circles having a radius ($R_D$), the array having a pitch ($\delta$) between neighboring features, where $\delta$ is at least $3R_D$, the array extending a length ($L_{AX}$) along the flow direction, the array extending a length ($L_{AY}$) perpendicular to the flow direction, the channel having a length ($L_{CX}$) along the flow direction, where $L_{CX}$ is greater than or equal to $L_{AX}$, the channel having a length ($L_{CY}$) perpendicular to the flow direction, where $L_{CY}$ is greater than or equal to $L_{AY}$, the channel having a height (h), which is at least $2R_D$ and at most $h_{MAX}$, where $h_{MAX}$ is calculated from the following equation $$h_{MAX} = \theta_{MAX} \frac{L_{AX} L_{AY}}{L_{CX} L_{CY} \delta^2} \frac{\rho_L RT}{(1-RHI)M_W P_0} \exp\left(\frac{\Delta H_{VAP}}{R}\left(\frac{1}{T}-\frac{1}{T_0}\right)\right)\pi R_D^3 G(\gamma)$$

$$G(\gamma) = \frac{2-3\sin\left(\frac{\pi}{2}-\gamma\right)+\sin^3\left(\frac{\pi}{2}-\gamma\right)}{3\cos^3\left(\frac{\pi}{2}-\gamma\right)}$$

where γ is the liquid contact angle for the hydrophobic material, $\theta_{MAX}$ is the maximum acceptable evaporated volume fraction of the droplets, $\rho_L$ is the volume density of the liquid, R is the molar gas constant, T is the temperature, RHI is the initial relative vapor saturation of the gas component of the liquid, $P_0$ is a reference vapor pressure of the liquid at a corresponding reference temperature $T_0$, $M_W$ is the molar weight of the liquid and $\Delta H_{VAP}$ is the enthalpy of evaporation of the liquid.

Embodiment 21

The flow system according to anyone of the preceding embodiments, wherein the pattern of hydrophilic features comprises at least two regions, and where the array of one region differs from the array of another region.

Embodiment 22

The flow system according to anyone of the preceding embodiments, wherein the region supporting the hydrophilic features is located centrally within the flow compartment.

Embodiment 23

The flow system according to anyone of the preceding embodiments, wherein the number of hydrophilic features is at least 1,000, preferably at least 10,000, preferably at least 100,000, preferably at least 1,000,000, preferably at least 10,000,000.

Embodiment 24

The flow system according to anyone of the preceding embodiments, wherein the flow compartment is channel shaped and forms a flow direction between two openings in opposite ends of the compartment.

Embodiment 25

The flow system according to embodiment 13, wherein the flow compartment and the openings have a rectangular shape in a cross section perpendicular to the flow direction.

Embodiment 26

The flow system according to embodiment 13, wherein the flow compartment has a rectangular shape and the openings have a circular shape in a cross section perpendicular to the flow direction.

Embodiment 27

The flow system according to anyone of the preceding embodiments, wherein the hydrophilic features is configured to support the nano-to-attoliter droplets and where the liquid exhibits a contact angle on the hydrophobic substrate of at least 90 degrees and at most 150 degrees.

Embodiment 28

The flow system according to anyone of the preceding embodiments, wherein the hydrophilic features is configured to support the nano-to-attoliter droplets having a radius of at least 0.1 μm and at most 100 μm.

Embodiment 29

The flow system according to anyone of the preceding embodiments, wherein the hydrophilic substrate is glass, a hydrophilic polymer or a metaloxide compound.

Embodiment 30

The flow system according to anyone of the preceding embodiments, wherein the hydrophobic layer is a molecular monolayer covalently grafted to the substrate.

Embodiment 31

The flow system according to anyone of the preceding embodiments, wherein the hydrophobic layer is a molecular monolayer chemisorbed on a metal substrate.

Embodiment 32

The flow system according to anyone of the preceding embodiments, wherein the one or more captured analytes become covalently crosslinked or coupled to the capture probe subsequent to capture.

Embodiment 33

The flow system according to anyone of the preceding embodiments, wherein the capture probe is an oligonucleotide or a synthetic oligonucleotide, the analyte is an oligonucleotide or a molecular complex containing oligonucleotides, where the analyte is bound to the capture probe via a sequence complementary to the capture probe sequence and where the covalent crosslinking is carried out by using an interstrand crosslinking agent such as platinum complexes, mitomycin C, nitrogen mustards, psoralens or aldehydes.

Embodiment 34

The flow system according to anyone of the preceding embodiments, wherein the capture probe is a protein, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide or uranyl acetate.

Embodiment 35

The flow system according to anyone of the preceding embodiments, wherein the digital counting is a digital counting measurement.

Embodiment 36

The flow system according to anyone of the preceding embodiments, wherein the digital counting measurement is a single-enzyme linked molecular analysis (SELMA), digital polymerase chain reaction (dPCR), single enzyme-linked immunosorbent assay (sELISA) or digital single-enzyme linked immunosorbent assay (dELISA).

Embodiment 37

A method of preparing a flow system as defined in any one of the preceding embodiments.

Embodiment 38

A method of using a flow system as defined in any one of the preceding embodiments for digital counting of at least one or more distinct analyte types.

Embodiment 39

A method for digital counting of at least one or more distinct analyte types, the method comprising counting the analyte types contained in a plurality of liquid nano-to-attoliter droplets under a gas phase seal.

Embodiment 40

The method according to embodiment 39, wherein the gas phase seal establishes a vapor pressure within the flow system capable of reducing evaporation of the microdroplets.

Embodiment 41

The method according to any one of embodiments 39-40, wherein the digital counting is performed in a flow system, which flow system comprises a support having a pattern of hydrophilic features in or on a hydrophobic substrate, the hydrophobic substrate being embedded in a flow compartment comprising at least one opening, the hydrophilic features configured to support the plurality of liquid nano-to-attoliter droplets.

Embodiment 42

The method according to any one of embodiments 39-41, wherein the hydrophilic features are circular having a radius ($R_D$), and where the maximum droplet volume ($V_D$) a single hydrophilic circle can support is $$V_D = \pi R_D^3 G(\gamma)$$

$$G(\gamma) = \frac{2 - 3\sin\left(\frac{\pi}{2} - \gamma\right) + \sin^3\left(\frac{\pi}{2} - \gamma\right)}{3\cos^3\left(\frac{\pi}{2} - \gamma\right)}$$

where $\gamma$ is the liquid contact angle on the hydrophobic substrate.

Embodiment 43

The method according to any one of embodiments 39-42, wherein the gas phase seal reduces evaporation of each nano-to-attoliter droplet to less than 50 percent of the maximum droplet volume.

Embodiment 44

The method according to any one of embodiments 39-43, wherein the flow system is as defined in any one of embodiments 1-36.

Embodiment 45

The method according to any one of embodiments 39-44, further comprising the step of (i) contacting a pattern of hydrophilic features in or on a hydrophobic substrate with a sample containing the one or more analyte types.

Embodiment 46

The method according to any one of embodiments 39-45, comprising the step of (ii) capturing at least one analyte type on the hydrophilic features.

Embodiment 47

The method according to any one of embodiments 39-46, comprising the step of (iii) labeling the at least one captured analyte type with a labeling agent specific to the analyte type to be detected.

Embodiment 48

The method according to any one of embodiments 39-47, comprising the step of (iv) flowing across and withdrawing from the pattern a detection agent to produce the individual droplets in the form of nano-to-attoliter droplets.

Embodiment 49

The method according to any one of embodiments 39-48, comprising the step of (v) counting the number of the droplets hosting both the labeling and detection agent.

Embodiment 50

The method according to any one of embodiments 39-49, comprising repeating steps (iii), (iv) and (v) one or more times.

Embodiment 51

The method according to any one of embodiments 39-50, comprising repeating steps (iii), (iv) and (v) by using, instead of the first labeling agent, a second labeling agent specific to a second analyte type to be detected.

Embodiment 52

The method according to any one of embodiments 39-51, comprising a step of deactivating the labeling agents present in the previous step before repeating steps (iii), (iv) and (v).

Embodiment 53

The method according to any one of embodiments 39-52, wherein the labeling agent is deactivated by detachment from the surface-bound analyte and removed by flushing of the flow system.

Embodiment 54

The method according to any one of embodiments 39-53, wherein the labeling agent is detached by enzymatic cleavage.

Embodiment 55

The method according to any one of embodiments 39-54, wherein the labeling agent is detached by chemical cleavage or desorption by adjusting the pH, adjusting the ionic strength, adding denaturing salts or adding detergents.

Embodiment 56

The method according to any one of embodiments 39-55, wherein the labeling agent is detached by raising the temperature of the flow system.

Embodiment 57

The method according to any one of embodiments 39-56, wherein the labeling agent is deactivated by changing its chemical or physical state.

Embodiment 58

The method according to any one of embodiments 39-57, wherein the labeling agent comprises an enzyme and wherein the state of the enzyme is changed by chemical or biochemical modification of the active site.

Embodiment 59

The method according to any one of embodiments 39-58, wherein the labeling agent comprises an enzyme and wherein the state of the enzyme is changed by chemical or physical disruption of the tertiary structure of the enzyme.

Embodiment 60

The method according to any one of embodiments 39-59, wherein the labeling agent comprises an enzyme and a specific analyte recognition moiety, and the analyte recognition moiety is chosen from the following group of molecules: oligonucleotides, proteins, peptides, aptamers, antibodies, complexes thereof or synthetic variants thereof.

Embodiment 61

The method according to any one of embodiments 39-60, wherein one or more capture probes for one or more distinct analyte types are attached to the hydrophilic features.

Embodiment 62

The method according to any one of embodiments 39-61, wherein one or more capture probes for one or more distinct analyte types are attached to the hydrophilic features by a linker moiety, the linker moiety being chosen from the following group of molecules: poly(ethylene glycols), linear or branched alkanes, peptides, oligonucleotides or synthetic variants thereof.

Embodiment 63

The method according to any one of embodiments 39-62, comprising more than one type of capture probe attached to the hydrophilic features, and wherein the different types of capture probes are arranged in the regions.

Embodiment 64

The method according to any one of embodiments 39-63, wherein the capture probes are selected from the following group of probes: oligonucleotides, proteins, peptides or synthetic variants thereof.

Embodiment 65

The method according to any one of embodiments 39-64, wherein the sample containing the one or more analyte types in a liquid is contacted with the substrate containing the hydrophilic features by full immersion.

Embodiment 66

The method according to any one of embodiments 39-65, comprising removing the liquid and washing the substrate.

Embodiment 67

The method according to any one of embodiments 39-66, wherein the labeling is performed by bringing a solution containing a labelling agent for the analyte in contact with the captured analyte by full immersion.

Embodiment 68

The method according to any one of embodiments 39-67, comprising removing the solution containing residual probes and washing the substrate.

Embodiment 69

The method according to any one of embodiments 39-68, wherein the liquid is actuated across the flow channel by means of a pressure drop from the inlet to the outlet.

Embodiment 70

The method according to any one of embodiments 39-69, wherein the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

Embodiment 71

The method according to any one of embodiments 39-70, wherein the sample is selected from the following group of samples: blood, plasma, serum, urine, saliva, cerebrospinal fluid, tear fluid, or tissue.

Embodiment 72

The method according to any one of embodiments 39-71, wherein the sample is selected from laboratory-processed samples of the following sample group: blood, plasma, serum, urine, saliva, cerebrospinal fluid, tear fluid or tissue such as a processed blood sample.

Embodiment 73

The method according to any one of embodiments 39-72, wherein the one or more captured analytes become covalently crosslinked or coupled to the capture probe subsequent to capture.

Embodiment 74

The method according to any one of embodiments 39-73, wherein the capture probe is an oligonucleotide or a synthetic oligonucleotide, the analyte is an oligonucleotide bound to the capture probe via a sequence complementary to the capture probe sequence and where the covalent crosslinking is carried out by using an interstrand crosslinking agent such as platinum complexes, mitomycin C, nitrogen mustards, psoralens or aldehydes.

Embodiment 75

The method according to any one of embodiments 39-74, wherein the capture probe is a protein, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide or uranyl acetate.

Embodiment 76

The method according to any one of embodiments 39-75, wherein the digital counting is a digital counting measurement.

Embodiment 77

The method according to any one of embodiments 39-76, wherein the digital counting measurement is a single-enzyme linked molecular analysis (SELMA), digital polymerase chain reaction (dPCR), single enzyme-linked immunosorbent assay (sELISA) or digital single-enzyme linked immunosorbent assay (dELISA).

Embodiment 78

The flow system according to any one of embodiments 1-38, wherein the gas phase is provided by atmospheric air, and/or wherein the capture probes are selected from the group of single-stranded DNA oligos, single-stranded locked nucleic acid oligos or single-stranded peptide nucleic acid oligos, and/or where different types of capture probes are arranged in regions, and/or where the analytes are single- or double-stranded DNA extracted from a processed blood sample, and/or where the labelling agent comprises a detection modality and a recognition moiety, and/or where the detection modality is an enzyme and/or the recognition moiety is selected from the group of single-stranded DNA oligo, a single-stranded locked nucleic acid oligo or a single-stranded peptide nucleic acid oligo.

Embodiment 79

The method according to any one of embodiments 39-77, wherein the gas phase is provided by atmospheric air, and/or wherein the capture probes are selected from the group of single-stranded DNA oligos, single-stranded locked nucleic acid oligos or single-stranded peptide nucleic acid oligos, and/or where different types of capture probes are arranged in regions, and/or where the analytes are single- or double-stranded DNA extracted from a processed blood sample, and/or where the labelling agent comprises a detection modality and a recognition moiety, and/or where the detection modality is an enzyme and/or the recognition moiety is selected from the group of single-stranded DNA oligo, a single-stranded locked nucleic acid oligo or a single-stranded peptide nucleic acid oligo.

Embodiment 80

Use of a plurality of liquid nano-to-attoliter droplets under a gas phase seal for digital counting of at least one or more distinct analyte types.

Embodiment 81

The use according to embodiment 80, which is carried out by the method according to any one of the embodiments 39-77 and 79.

Embodiment 82

The use according to any one of embodiments 80-81, which is carried out in a flow system according to any one of the embodiments 1-38 and 78.

In the following, some non-limiting examples of applications are described:

Example 1

Formation and Preservation of a Femtoliter Aqueous Micro Droplet Array

To form stable microdroplets, a regular quadratic array of hydrophilic circular features embedded on a planar hydrophobic region was contacted with a phosphate buffered aqueous solution. A 10 µl plug of the solution was actuated across the surface of the array, thus leaving microdroplets behind on the hydrophilic features as shown on the micrograph in FIG. 4.

The flow system was defined by two openings at each end of a rectangular channel to guide the liquid. The width of the channel was 3 mm, the length was 16 mm and the height was 150 µm. The array was placed centrally in the channel, with a width of 2.9 mm, a length of 14 mm and comprised a total of 406,000 hydrophilic features. The diameter of the hydrophilic circles was 5 µm, and the inter-circle spacing was 10 µm. The contact angle of the aqueous solution on the hydrophobic surface was approx. 110 degrees and the experiment was conducted at ambient temperature of 21° C. At most 3% of the droplet volume was allowed to evaporate, which according to Eqn. 11 implies a maximum height of the channel of approx. 680 µm for dry air (RHI=0). Because the height of the flow compartment was only 150 µm and hence less than the maximum height, the gas phase seal was functional and was able to keep the microdroplets intact.

The array was contacted with the bulk aqueous solution by placing a 10-µl volume into a loading pad connected to the channel inlet. Next, at the channel outlet a negative pressure was applied, thus actuating the 10-µl liquid plug across the channel at a flowrate of 5 µl/min. Once the receding edge of the bulk liquid had reached the channel outlet, the pressure was terminated and a new liquid plug placed on the loading pad. Due to the functional gas phase seal, the droplets formed on top of the hydrophilic features remained stable for more than one hour, without experiencing any significant evaporation, see for example FIG. 12C.

Example 2

How to Render an Array of Aqueous Micro-Droplets Evaporation-Resistant by Optimizing Flowchannel-, Droplet- and Array-Geometry Consider a flow channel in which a chemically patterned solid substrate has been embedded. The chemical pattern consists of circular hydrophilic regions organized into an array. The hydrophilic array is surrounded by a continuous hydrophobic region. In this way, an array of microdroplets is formed on top of the hydrophilic features once an aqueous solution is infused and subsequently withdrawn from the flowchannel, as illustrated in Example 1.

The dimensions of the flow channel are defined on FIG. 13, and are characterized by h, which is the height of the channel, $l_A$, which is the length of the flowchannel covered by the array, $l_E$, which is the length of the excess part of the channel leading to the inlet/outlet, but not hosting the array. The parameters defining the array are the droplet radius $R_D$, defined as the radius of the hydrophilic feature on the solid substrate and $\delta$ which is the center-to-center distance between neighboring droplets. In the following we will assume an array organized in a tetragonal pattern, however solutions for other array patterns may be derived using the same principles as shown below.

First, we will calculate the total molar amount of water present in the flow channel. This is done by calculating the volume of a droplet $(V_D)$ and multiplying it with the total number of droplets present. We will assume that a droplet can be represented by a hemi-sphere exhibiting half the volume of a sphere. Because the array and flow channel is identical along the γ-direction, we only need to consider a one-dimensional array (as the one sketched) comprised of a single line of droplets, as well as a pseudo one-dimensional flowchannel with a width of the interdroplet spacing $\delta$. The total number of droplets $(N_D)$ along the one-dimensional array is then $$N_D = l_A/\delta \qquad \text{Eqn. 12}$$

The total molar amount $(n_{TOT})$ of all the droplets can now be evaluated as $$n_{TOT} = \frac{m_W}{M_W} = \frac{N_D V_D \rho_W}{M_W} = \frac{l_A}{\delta} \frac{2\pi R_D^3 \rho_W}{3M_W} \qquad \text{Eqn. 13}$$

Here, $m_w$ is the total mass of all the droplets, $M_W$ is the molar weight of water (18.016 g/mol) and $\rho_w$ is the density of water (1000 g/l). To calculate how much of the water that is going to evaporate at a given temperature, we need to utilize the Clausius-Clapeyron equation to calculate the equilibrium vapor pressure of water $(P_W)$:

$$P_W = P_0 \exp\left(\frac{\Delta H_{VAP}}{R}\left(\frac{1}{T_0} - \frac{1}{T}\right)\right) \qquad \text{Eqn. 14}$$

Here, $P_0$ is a reference equilibrium vapor pressure at the reference temperature $T_0$, T is the reaction temperature, R is the gas-constant (8.31 J·mol$^{-1}$·K$^{-1}$) and $\Delta H_{VAP}$ (40.65 kJ·mol$^{-1}$) is the enthalpy change upon evaporation of water.

Suitable values for $P_0$ and $T_0$ could be 2.34 kPa at a temperature of 293 K, respectively. For a closed flow channel having a volume of $V_F$, the vapor pressure of water indicates how much water can be transferred into the air as water vapor. The molar amount of water vapor at equilibrium $(n_{EVAP})$ follows from the ideal gas law as $$n_{EVAP} = \frac{P_W}{RT} V_F = \frac{P_0}{RT} \exp\left(\frac{\Delta H_{VAP}}{R}\left(\frac{1}{T_0} - \frac{1}{T}\right)\right)(2l_E + l_A)h\delta \qquad \text{Eqn. 15}$$

The fraction of evaporated water $(\theta_W)$ may now be evaluated as the ratio of evaporated water to the total molar amount of water.

$$\theta_W = \frac{n_{EVAP}}{n_{TOT}} = \frac{P_0}{RT} \exp\left(\frac{\Delta H_{VAP}}{R}\left(\frac{1}{T_0} - \frac{1}{T}\right)\right)(2l_E + l_A)h\delta \frac{3M_W\delta}{2\pi l_A R_D^3} = \frac{3hP_0M_W}{2\pi RT\rho_W} \exp\left(\frac{\Delta H_{VAP}}{R}\left(\frac{1}{T_0} - \frac{1}{T}\right)\right)\frac{\delta^2}{R_D^3}\left(2\frac{l_E}{l_A} + 1\right) \qquad \text{Eqn. 16}$$

We will now introduce (i) the dimensionless scaling factor $N=\delta/R_D$, which is a geometrical parameter characterizing the array (i.e. greater N-values leads to a more scarcely populated array), and (ii) the dimensionless scaling factor $\varphi = l_E/l_A$, which is a geometrical parameter characterizing the flow channel design (i.e. a large $\varphi$-value indicates that the array occupies only a small part of the flow channel). Using this notation, Eqn. 16 may be rewritten as $$\theta_W = \frac{3hP_0M_W}{2\pi RT\rho_W} \frac{1}{R_D} \exp\left(\frac{\Delta H_{VAP}}{R}\left(\frac{1}{T_0} - \frac{1}{T}\right)\right) N^2(2\varphi + 1) \qquad \text{Eqn. 17}$$

Eqn. 17 may be rearranged such that if a desired maximum evaporated fraction $(\theta_{MAX})$ is chosen, then the corresponding maximum height $(h_{MAX})$ can be evaluated:

$$h_{MAX} = \frac{2\pi RT\rho_W}{3P_0M_W} \exp\left(\frac{\Delta H_{VAP}}{R}\left(\frac{1}{T} - \frac{1}{T_0}\right)\right) \frac{R_D}{N^2(2\varphi + 1)} \theta_{MAX} \qquad \text{Eqn. 18}$$

In FIG. 11, Eqn. 17 and Eqn. 18 are plotted for various flow channel/droplet/array geometries and temperatures. Further in FIG. 12, the experimental demonstration of droplet stability as a function of temperature and flowchannel geometry has been shown. For a flowchannel optimized for droplet preservation (FIG. 12C), the droplet array remains stable for at range of temperatures (25-45° C., as demonstrated here) and for an extended period of time of at least 1.5 hours. In principle, once thermodynamic equilibrium has been established, the droplet array would be stable indefinitely. However, in reality the flowchannel/array cannot be perfectly sealed from the external environment and hence droplets may slowly evaporate.

Example 3

Fabrication of a Flow System

Fabrication of a flow system took place in two main steps; one step utilizes UV photolithography and microfabrication processing to produce the patterned hydrophilic features, whereas the second step deals with integrating the hydrophilic pattern into a flow compartment exhibiting the right geometry. Below both steps will be described in more detail.

Microfabrication of a Patterned Hydrophilic Substrate.

In this embodiment of the invention, the hydrophilic features were composed of quartz ($SiO_2$) and the hydrophobic region was composed of perfluorodecyltrichlorosilane (FDTS). In the first step of the fabrication process, a molecular monolayer of FDTS was deposited on the quartz wafer by molecular vapor deposition using an MVD 100 Molecular Vapor Deposition system (Applied Microstructures Inc.). The FDTS underwent covalent attachment to silanol groups on the surface of the quartz and hence produced a hydrophobic monolayer on the wafer surface.

Next, a layer of AZ5214E photoresist (Microchemicals GmbH) was deposited on top of the FDTS-treated wafer by spin-coating followed by a soft bake of the wafer at 90° C. to evaporate excess solvents. The photoresist was exposed to UV illumination through a chromium mask using a SÜSS Mask Aligner, model MA6 (SÜSS MicroTec), followed by development of the wafer in AZ351B developer solution (Microchemicals GmbH). In this way, a connected pattern of photoresist remained on the wafer thus exposing circular holes to the FDTS monolayer below.

In the final processing step, the FDTS monolayer was selectively removed to expose the hydrophilic quartz surface beneath. This was achieved by subjecting the wafer to an oxygen-plasma for a short duration using a model 300 Plasma Processor (TePla), thus removing the FDTS monolayer, but leaving behind the thicker photoresist film. In order to remove the photoresist film, the wafer was sonicated in acetone for 10 min., thus dissolving the film and hence providing a pattern of hydrophilic quartz features surrounded by a hydrophobic FDTS molecular monolayer.

Integration of the Microfabricated Array in a Flow Channel

Prior to integration, the microstructured wafer was cut into rectangular pieces (25 mm×12 mm) to fit into the flow compartment. In the cases, where the array required further surface functionalization, the functionalization protocol was conducted prior to compartment integration, as described in Examples 4-5 below.

The flow channel and a liquid loading pad was prepared by CNC milling of a poly(methyl methacrylate) (PMMA) sheet. The flow channel had a width of 1 mm, a length of 8 mm, a height of 100 μm and a wall-thickness of 200 μm. The flow channel was terminated by an outlet connected to a peristaltic pump, which provided the suction required for liquid actuation. The liquid loading pad exhibited a volume of approximately 100 μl and was connected to the flow channel via the inlet. The flow channel, loading pad, inlet and outlet were carved out of a single 8 mm thickness PMMA slab, which will henceforth be referred to as the PMMA flow structure.

To attach a rectangular wafer-piece (chip) hosting the microfabricated array of hydrophilic features to the PMMA flow structure, a piece of double-sided pressure-sensitive adhesive film (ARcare 90106, Adhesives Research, Inc.) with a nominal thickness of 142 μm was cut with a $CO_2$ laser instrument. The geometry of the laser-cut adhesive film was matched to that of the PMMA flow structure, but slightly smaller, such that the flow channel was surrounded by—but not in contact with—the adhesive. Next, the adhesive was attached to the bottom side of the PMMA flow structure, followed by placing the array chip on top of the adhesive. The assembly—PMMA flow structure, adhesive and array chip—was then sandwiched between two flat 5 mm thickness PMMA sheets and placed in a bonding press. The sandwich was clamped at a pressure of 6 kN for 60 sec. at 40° C. In this way, the adhesive was compressed to a thickness of 100 μm as defined by the height of the flow channel. The resulting bonded assembly defined a functional flow system.

Example 4

Digital Counting of Single DNA Molecules

In this example, it is shown how single biomolecules—in this case single stranded DNA—can be detected and digitally counted by use of a flow system with an integrated droplet array chip. The flow system assembly was produced and operated according to the procedures described in Examples 1-3, but prior to integration of the droplet array chip into the PMMA flow structure, the chip was subjected to further surface functionalization to allow for specific capture of the single stranded target DNA. The microfabricated chip consisted of 93,750 circular hydrophilic features having diameters of 4 μm and arranged in a square array with an inter-feature spacing of 8 μm.

Surface Functionalization Protocol

The droplet array chips were cleaned thoroughly by 10 min. sonication in acetone followed by 10 min. sonication in isopropanol followed by 10 min. sonication in ethanol. The chips were dried under a nitrogen flow and immersed in a solution of 1% (v/v) epoxysilane (Dynasylan GLYEO, Evonik Industries) solution in 95% (v/v) ethanol. The chips were incubated for 30 min. in the epoxysilane solution, and was subsequently washed three times with 95% ethanol, dried under a nitrogen flow and cured at 110° C. for 30 min.

Next, epoxy-groups on the silanized chips were reacted with amine groups present on poly(ethylene glycol) moieties. The poly(ethylene glycol) consisted of a mixture of methoxy-poly(ethylene glycol)$_{2000}$-amine (OH-PEG$_{2000}$-NH$_2$) (Jenkem Technology) and carboxylic acid-poly(ethylene glycol)$_{2000}$-amine (COON-PEG$_{2000}$-NH$_2$) (Jenkem Technology). The mixture had a 10:1 molar ratio of OH-PEG$_{2000}$-NH$_2$ to COOH-PEG$_{2000}$-NH$_2$ and a nominal total concentration of 100 g/l in 10 mM phosphate buffered saline (PBS), 138 mM NaCl, 2.7 mM KCl, 1.5 M ammonium-sulphate, pH 7.4. The chips were incubated with the mixture for 20 hours at 40° C. Subsequently, the chips were washed three times with Milli-Q water (Millipore Corp.) and dried under a nitrogen flow.

In the last surface modification step, the chips were functionalized with a capture probe specific to the DNA target. The capture probe was a 14-mer peptide nucleic acid (PNA) with a lysine group at the N-terminal, which was used for attachment to the carboxylic acid-group on the surface grafted COOH-PEG$_{2000}$-NH$_2$. The sequence of the PNA probe from N-terminal to C-terminal was K-O-ACA TAG TTG ACA CG-OO (SEQ ID NO: 1: ACA TAG TTG ACA CG) (Panagene), where K represents a lysine group, O represents an ethylene glycol linker and the letters G, C, A and T represent PNA analogues of the DNA nucleobases.

First, the surface of the chips were prepared for reaction to the PNA probe by immersing them in a mixture of N-hydroxysuccinimide and N-(3-dimethylaminopropyl)-N'-ethylcarbodiimide hydrochloride at a molar ratio of 1:1 and at a nominal concentration of 25 g/l for each of the compounds in 100 mM 2-(N-morpholino)ethanesulfonic (MES) buffer. The chips were incubated in the mixture for 30 min. at 4° C. followed by a brief flushing in 100 mM MES buffer. Next, the chips were immersed in a 100 nM solution of the PNA probe in 100 mM MES buffer and incubated for 30 min. at ambient temperature. Subsequently, the chips were flushed briefly with 100 mM MES buffer followed by immersion in 50 mM tris(hydroxymethyl)aminomethane for 10 min. The chips were flushed with Milli-Q water three times, dried under a nitrogen flow and stored in a vacuum desiccator until they were bonded to the PMMA flow structure, as outlined in example 3.

Detection Protocol

The target for detection was a 50-bp DNA oligo (5'-TCT GTC GTA GGC ACA GAG CGG TCT TAC GGC CAG TCG CGT GTC AAC TAT GT-3' (SEQ ID NO: 2)). The last 14 basepairs of the DNA oligo were complementary to the PNA capture probe, whereas the first 12 basepairs of the DNA oligo were complementary to a DNA-based labelling agent. The labelling agent was comprised by one or more 12-bp DNA oligos conjugated to a horseradish peroxidase enzyme. The sequence of the labeling DNA oligo was 5'-GCC TAC GAC AGA-3'-TEG-biotin (SEQ ID NO: 3 coupled to TEG-biotin), where TEG represents a tetra(ethylene glycol) linker.

The labelling agent was prepared by mixing a neutravidin-horseradish peroxidase (NAv-HRP) conjugate (Invitrogen, A2664) with the labeling oligo in a 1:3 molar ratio of NAv-HRP to oligo. The final concentration of NAv-HRP was 100 nM and the mixture was prepared in a 5× saline sodium citrate (SSC) buffer, 1.0 g/l bovine serum albumin (BSA), 0.5% (v/v) Triton X-100, pH 7.0. The mixture was incubated at 4° C. for 24 hours, thus enabling the biotinylated DNA oligos to become attached to the neutravidin moiety on NAv-HRP. The resulting conjugate exhibits an average of 3 bound DNA oligos per NAv-HRP and will be abbreviated by NAv-HRP-LO$_3$ henceforth.

The following buffers were used for the detection experiment:

Passivation Buffer: 5×SSC buffer, 0.5% (v/v) Triton X-100, 10 g/l BSA, pH 7.0.

Labeling Buffer: 5×SSC buffer, 0.5% (v/v) Triton X-100, 10 g/l BSA, pH 7.0.

Cleaning Buffer 1: 10 mM PBS, 138 mM NaCl, 2.7 mM KCl, 0.1% (v/v) Triton X-100, 50 g/l 20 kDa molar weight poly(ethylene glycol) (PEG$_{20000}$), pH 7.4.

Cleaning Buffer 2: 10 mM PBS, 138 mM NaCl, 2.7 mM KCl, 50 g/l PEG$_{20000}$, pH 7.4.

Detection Buffer: 10 mM PBS, 138 mM NaCl, 2.7 mM KCl, 10 g/l PEG$_{20000}$, 1.0 mM H$_2$O$_2$, pH 7.4.

Solutions of varying nominal DNA target concentrations (10 fM, 1 fM and 100 aM) as well as a control containing no DNA target were prepared in 5×SSC buffer, 0.5% Triton X-100, pH 7.0 immediately prior to the detection experiments. In order to conduct a detection experiment the flow system was operated in the following way:

Step 1: Actuate 25 µl of DNA target solution through the flow channel at a flowrate of 0.2 µl/min.

Step 2: Infuse the flow channel with 10 µl Passivation Buffer

Step 3: Incubate for 10 min. and actuate the solution out of the flow channel

Step 4: Infuse the flow channel with 10 µl of 50 pM NAv-HRP-LO$_3$ in Labeling Buffer Step 5: Incubate for 10 min. and actuate the solution out of the flow channel Step 6: Actuate 100 µl Cleaning Buffer 1 at a flowrate of 10 µl/min Step 7: Actuate 100 µl Cleaning Buffer 2 at a flowrate of 10 µl/min Step 8: Actuate 3 µl 200 pM ampliflu red (Sigma Aldrich, 90101-5MG-F) solution in Detection Buffer at a flowrate of 5 µl/min Briefly, the above protocol enabled the DNA target to become bound to the surface-attached PNA capture probes in step 1. Next, the captured DNA target was labelled with the NAv-HRP-LO$_3$ in steps 4-5. After removing excess labelling agents in steps 6-7, microdroplets containing the detection reagent ampliflu red was established in step 8. Ampliflu red is a fluorogenic substrate for horseradish peroxidase, which upon enzymatic processing is converted into the fluorescing compound resorufin (excitation 570 nm, emission 585 nm). Consequently, droplets hosting the labelling agent generated a fluorescence signal, which was readily detected using a fluorescence microscope.

Subsequent to step 8, the flow system was inspected under a fluorescence microscope (Zeiss Axio Vert.A1) using a 555-nm LED excitation source in combination with an appropriate fluorescence filter-set to detect the emitted signal from resorufin. Corresponding brightfield and fluorescence micrographs were recorded with a 1.4 MP CCD camera (AxioCam MR3), as shown in FIG. 14.

The fluorescence micrographs were quantified using the image analysis software ImageJ in order to count the number of fluorescing droplets. Briefly, grayscale micrographs were converted to binary format by formatting pixel values below a certain intensity threshold to 0 and pixel values above to 1. Next, connected pixel clusters of value "1" were counted. Clusters consisting of less than 4 pixels were discarded as noise. The total number of clusters for the entire array was recorded for subsequent data analysis. The same intensity threshold value was applied to all fluorescence micrographs from all detection experiments.

The results from a total of 20 detection experiments are shown on FIG. 15. The figure shows the percentwise fraction of droplets present on the array exhibiting a detectable fluorescence signal for different concentrations of DNA target. In the control sample, where no DNA target was present, still a number of droplets were detectable. This is likely due to the presence of non-specifically bound (e.g. physisorption or chemisorption) labelling agents on the array. Non-specific binding (NSB) is a common phenomenon, which is more pronounced in high-sensitive applications such as single-molecule counting. In the experiments shown here, the fraction of droplets hosting a NSB labelling agent was 0.280+/−0.097% (average+/−standard deviation from five experiments). On the other hand, samples containing target DNA was found to exhibit a higher fraction of detectable microdroplets, thus demonstrating specific detection and quantification of minute amounts of the molecular target. However, as the concentration of the target DNA increased, the number of fluorescing droplets did not increase in a directly proportional fashion. This might be due to a concentration dependent loss of target by e.g. non-specific adsorption on the other surfaces of the flowsystem, or possibly an incomplete labelling of the surface-bound DNA targets.

Example 5

Repeated Detection of Single DNA Molecules

In this example, it is shown how captured DNA targets may become repeatedly detected by deactivation of the labelling agents. The flow system used in this example was produced and operated according to Examples 1-3 and was functionalized according to the surface functionalization protocol provided in Example 4.

As will be illustrated below, the advantage of using repeated detection of a captured target is that each time the detection is repeated the signal-to-noise ratio is improved, and so is the limit-of-detection. Furthermore, this may enable an increased specificity in terms of discriminating between DNA targets harboring one or more single nucleotide polymorphisms (SNPs) and wildtype DNA strands without the SNPs, but otherwise identical, e.g. Example 6.

In the present example, we applied the same detection protocol as described in Example 4, but repeated the labelling and detection steps three times. Since the capture probe was based on PNA and the labelling agent was based on DNA, it was possible to selectively remove the labelling agent using T7 Exonuclease to digest the labelling agent, while keeping the capture probe/target-complex intact. Furthermore, to remove the signal from NSB labelling agents, the enzyme part of the probe was deactivated with a solution of phenol, which selectively altered the structure of the active site of the peroxidase enzyme, thus preventing it from producing a signal in the following detection assays.

The Passivation Buffer, Labeling Buffer, Cleaning Buffer 1, Cleaning Buffer 2 and Detection Buffer were the same as applied in Example 4. In addition, the following two reagents were applied:

Digestion Buffer: 1500 units/ml of T7 Exonuclease (New England Biolabs, M0263L) in 50 mM potassium acetate, 20 mM tris-acetate, 10 mM magnesium acetate, 1 mM DTT, pH 7.9

Deactivation Buffer: 5.0 mM Phenol, 1.0 mM $H_2O_2$ in 10 mM PBS, 138 mM NaCl, 2.7 mM KCl, pH 7.4

The experiment was carried out in the following way to enable three distinct detection steps of the same captured DNA targets.

Step 1: Actuate 25 µl of DNA target solution through the flow channel at a flowrate of 0.2 µl/min.

Step 2: Infuse the flow channel with 10 µl Passivation Buffer

Step 3: Incubate for 10 min. and actuate the solution out of the flow channel

Step 4: Infuse the flow channel with 10 µl of 50 pM NAv-HRP-LO$_3$ in Labeling Buffer Step 5: Incubate for 10 min. and actuate the solution out of the flow channel Step 6: Actuate 100 µl Cleaning Buffer 1 through the flow channel at a flowrate of 10 µl/min Step 7: Actuate 100 µl Cleaning Buffer 2 through the flow channel at a flowrate of 10 µl/min Step 8: Actuate 3 µl 200 µM ampliflu red (Sigma Aldrich, 90101-5MG-F) solution in Detection Buffer at a flowrate of 5 µl/min Step 9: Record fluorescence and brightfield micrographs of the droplet array Step 10: Infuse the flow channel with 10 µl Digestion Buffer Step 11: Incubate for 10 min. and actuate the solution out of the flow channel Step 12: Actuate 20 µl Deactivation Buffer through the flow channel at a flowrate of 5 µl/min Step 13: Actuate 50 µl Cleaning Buffer 1 through the flow channel at a flowrate of 10 µl/min Step 14: Repeat steps 4-13
Step 15: Repeat steps 4-9

For each sample a series of three consecutive fluorescence micrographs were recorded and analyzed using the same setup and procedures as outlined in Example 4. The first micrograph in a series correspond to the first detection step, the next micrograph in a series correspond to the second detection step and so forth. By using specific markings on the flow system surface, which were visible on the brightfield micrographs, the coordinates of the fluorescence micrographs were corrected for changes in the XY-position between detection steps. In this way, it was possible to compare the XY-positions of individual droplets for the different detection steps. Next, for each micrograph in the detection series, the XY-pixel position of droplets exhibiting a fluorescence signal was recorded and compared to the remaining two members of the series. Droplet positions which did not differ by more than 4 pixels between the detection steps were considered to be a "persistent" droplet, i.e. a droplet repeatedly producing a signal, when labelling and detection agents are added.

The results of the three detection steps are shown in FIG. 16, in which a series of fluorescence micrographs are shown for a sample containing 100 aM DNA target. On the micrographs, persistent droplets have been labeled with a circle. For the control sample, where no DNA target was added, no persistent droplets could be identified in all three detection steps.

The following table shows a quantitative comparison between the 100 aM DNA target sample and the control sample. The table in summarizes the average results from 5 identically prepared samples containing 100 aM target DNA and 5 identically prepared control samples containing no target DNA. The table provides the average positive fraction of persistent droplets (Avg.), as defined in Example 5, for the control sample (first row) and for the 100 aM target DNA sample (second row). The standard deviation (St. dev.) corresponds to the standard deviation of the 5 samples. The third row provides the signal-to-noise (S/N) ratio resulting from each subsequent detection step. The S/N-ratio is provided as the experimentally measured value supplemented in parenthesis by the theoretical value. The experimental value was obtained by dividing the average values in the second row with the average values in the first row. The theoretical value was calculated by dividing the average value for the 100 aM samples with (i) 0.28% for the first detection step, (ii) $7.84 \cdot 10^{-4}$% (0.28%·0.28%) for the second detection step and (iii) $2.2 \cdot 10^{-6}$% (0.28%·0.28%·0.28%) for the third detection step.

|  | Analysis 1 | | Analysis 2 | | Analysis 3 | |
| --- | --- | --- | --- | --- | --- | --- |
|  | Avg. | St. dev. | Avg. | St. Dev. | Avg. | St. Dev. |
| Control | 0.280% | 0.097% | $6.1 \cdot 10^{-4}$% | $9.2 \cdot 10^{-4}$% | N/A | N/A |
| 100 aM | 0.507% | 0.160% | 0.243% | 0.091% | 0.221% | 0.084% |
| S/N ratio | 1.81 (1.81) | | 398 (310) | | Inf. (100,674) | |

The percentwise fraction of persistent droplets for the control sample decreased for each repetition of the detection step, and consequently lead to an increase in the S/N-ratio. The reason for this is that in the control sample only NSB labelling agents provide the fluorescence signal. These bind in a random fashion to the array, and because their signal is deactivated between subsequent detection steps, it is unlikely that the same droplet will produce a signal in a subsequent detection step. For example—assuming a random binding pattern of NSB labelling agents—if the fraction of droplets hosting a NSB labelling agent is 0.28% in each detection step, e.g. FIG. 15D, then there is only a $2.2 \cdot 10^{-6}$% ($0.28\% \cdot 0.28\% \cdot 0.28\%$) chance of observing persistent droplets in all three detection steps. For an array hosting 100,000 droplets, the false-positive detection rate of $2.2 \cdot 10^{-6}$% corresponds to only 0.002 false-positive detections. It is thus highly unlikely to observe any persistent droplets for the control sample.

Consequently, for these particular experimental settings all noise derived from NSB labelling agents can be ruled out, and hence any droplet that persists for at least three consecutive detection steps represents—with very high probability—a functionally assembled capture-probe/DNA-target/labelling-probe complex.

Example 6

Description of a Flow System Setup for Detection of Single DNA Molecules in a 1:10,000 (Target:Non-Target) Background of Non-Target DNA Differing in Sequence from the Target by a Single Basepair In this example, a flow system able to perform digital detection of a DNA analyte present in a 100 µl sample solution is obtained by following the steps described below. The analyte (target DNA) is expected to be present at a concentration of approx. 10 aM in the sample and contains the following sequence segment: 5'-TCT GTC GTA GGC ACA GAG CGG TCT TAC GGC CAG TCG CGT GTC AAC TAT-3' (SEQ ID NO: 4). In addition to the analyte, the sample is expected to contain another non-target DNA molecule (wildtype DNA) at a concentration approx. 10,000 times higher, i.e. 100 fM, and containing the following sequence segment: 5'-TCT GTC GTA GGC ACA GAG CGG TCT TAC GGC CAG TCG CGT GTC CAC TAT-3' (SEQ ID NO: 5). The target and the wildtype DNA differs in sequence only at the bolded and underlined position.

The capture probe is a single-stranded PNA oligo selected to be complementary to the 5'-end of the target and wildtype DNA, which can be achieved by using a capture probe containing the following sequence: 5'-GTG CCT ACG ACA GA-3' (SEQ ID NO: 6), where 5' and 3' corresponds to the N- and C-terminus of the probe, respectively. According to IDT Oligo Analyzer software (https://eu.idtdna.com/calc/analyzer), the melting temperature for the capture probe is expected to be at least 46.8° C., and hence 100% of both target and wildtype DNA will be bound at ambient temperature, i.e. 23° C. Consequently, the array needs to be designed to accommodate binding of at least 6 mio. DNA molecules, which corresponds to 100% binding of a 100 µl sample containing 100 fM DNA.

To conduct a digital counting measurement, the captured target DNA have to be labeled with a labelling agent consisting of a single-stranded DNA oligo containing the following sequence 5-ATA GTT GAC AC-3' (SEQ ID NO: 7) conjugated to an enzyme such as horseradish peroxidase, alkaline phosphatase or beta-galactosidase—all of which have fluorogenic substrates commercially available. The labelling agent exactly matches the sequence of the DNA target at the 3'-end. Under optimal binding conditions 82.6% of the target DNA will be bound to the labelling agent at a temperature of 23° C. (IDT Oligo Analyzer). However, under the same conditions 1% of the wildtype DNA will also be bound by the labelling agent due to the high sequence similarity between target and wildtype. Consequently, to conduct a digital counting measurement, the array is required to present at least 120,000 hydrophilic features. The amount of 120,000 features is chosen such that when the first labelling and the first detection steps have been conducted, then approx. half of the droplets of the array will produce a fluorescence signal, i.e. 1% of 6 mio. wildtype DNA+82.6% of 600 target DNA.

To accommodate 120,000 hydrophilic features, the features are to be shaped as circles having a diameter of 5 µm and placed in a regular quadratic array with a nearest neighbor separation of 10 µm. According to Eqn. 1 an individual hydrophilic feature may thus support an aqueous droplet having a maximum volume of $V_D$=52 femtoliter. To calculate the maximum droplet volume, a γ-value of 110° corresponding to the contact angle of water on a perfluorodecyltrichlorosilane (FDTS) support was applied. Consequently, the aggregate volume of the droplet array is $V_{DA}$=6.2 nanoliter (120,000 times 52 femtoliter). The maximum flow compartment volume is then obtained from Eqn. 9 as $V_{MAX}$=326 µl.

To calculate the maximum flow compartment volume, the following values were applied; $\rho_L$=1000 kg/m³ is the volume density of water, R=8.31 J/(mol·K) is the molar gas constant, T=296 K (23° C.) is the temperature, RHI=0 is taken as the initial relative water vapor saturation of dry atmospheric air, $P_0$=1226 Pa is the vapor pressure of water vapor at temperature $T_0$=283 K (10° C.), $M_W$=18.016·10⁻³ kg/mol is the molecular weight of water and $\Delta H_{VAP}$=40.65·10³ J/mol is the enthalpy of evaporation of water. The values were obtained from Lange's Handbook of Physical Chemistry (ISBN-13: 9780070163843) and from Atkin's Physical Chemistry, Volume 1: Thermodynamics and Kinetics (ISBN-13: 9780716785675).

However, in order for the droplets to (i) remain stable during the imaging detection step and (ii) provide optimal conditions for the enzymatic reaction only a small fraction of the droplet volume is allowed to evaporate. The maximum acceptable evaporated volume fraction of the droplets is thus set to 5%, i.e. $\theta_{MAX}$=0.05, hence leading to a flow compartment volume of $V_C$=16.3 µl, i.e. $V_C=\theta_{MAX} \cdot V_{MAX}$.

The final geometrical design of the flow compartment is obtained by choosing a rectangular channel-shape for the compartment exhibiting an aspect ratio of 10:1 and a length of $L_{CX}$=15 mm and a width of $L_{CY}$=1.5 mm. The height of the channel is thus required to be less than $h_{MAX}$=724 µm ($h_{MAX}=V_C/(L_{CY} \cdot L_{CX})$) in order to ensure that no more than 5% of the maximum droplet volume evaporates. The 10:1 aspect ratio may be applied to the array of hydrophilic features, such that the array will present 1,091×110 circular features, corresponding to $L_{AX}$=10.9 mm and $L_{AY}$=1.1 mm.

For the flow system setup outlined above, the DNA targets may become reliably detected in a background outnumbering the target 10,000-fold by repeating the labelling and detection steps three times, as described in Example 5. In this way, on average 60,496 DNA molecules (1% of 6 mio. wildtype DNA+82.6% of target DNA) is expected to provide a signal in the first detection step, corresponding to 60,000 false-positive detections of the wildtype DNA and 496 correct detections of target DNA.

In the second detection step, on average 1,010 DNA molecules (1% of 60,000 wildtype DNA+82.6% of 496 target DNA) is expected to provide a persistent signal, corresponding to 600 false-positive detections of wildtype DNA and 410 correct detections of target DNA. In the third detection step, on average 344 DNA molecules (1% of 600 wildtype DNA+82.6% of 410 target DNA) is expected to provide a persistent signal, corresponding to 6 false-positive detections of the wildtype DNA and 338 correct detections of target DNA.

For the third detection step, the number of correct detections is expected to surpass the number of false-positive detections by a factor of 56, thus providing an excellent quantification accuracy. However, by repeating the labelling and detection step a fourth time, the false-positive detections are expected to become completely removed.

Example 7

Analytical Relationship Between the Number of Signal-Positive Capture Sites and the Number of Applied Detection Cycles Consider an embodiment of the invention designed to detect and quantify a target oligonucleotide having a sequence displaying a genetic alteration in the form of a single basepair substitution compared to a reference (wildtype) oligonucleotide sequence. In this case, the target analyte would be the single basepair substituted oligonucleotide, and the reference (wildtype) oligonucleotide would thus constitute a highly similar non-target molecule, which might contribute greatly to the false-positive detection rate of a conventional single molecule counting method. In the current embodiment, capture sites may be functionalized with oligonucleotide capture probes complementary to a sequence common to both the target analyte and the non-target molecule. On the other hand, labelling agents may be constituted by oligonucleotides having a sequence complementary to the part of the target analyte exhibiting the single basepair substitution. Consequently, the labelling efficiency of the target analyte would be expected to be higher than that of the non-target molecule, but not necessarily much higher.

Consider that in the present example, the number of target analytes and non-target molecules captured on the capture sites are $N_{TA}$ and $N_{NM}$, respectively, and that the total number of capture sites available is $N_C$. In the present example, it is assumed that both target analytes and non-target analytes are distributed among the capture sites according to the Poisson distribution. Consequently, the number of compartments hosting at least one target analytes ($C_{TA}$) and the number of compartments hosting at least one non-target molecule ($C_{NM}$) is $$C_{TA}=N_C(1-\exp(-N_{TA}/N_C)) \qquad \text{Eqn. 19}$$

$$C_{NM}=N_C(1-\exp(-N_{NM}/N_C)) \qquad \text{Eqn. 20}$$

Further consider that the labelling efficiency of the target analyte by labelling agents is $P_{TA}$ and that the labelling efficiency of the non-target molecule by labelling agents is $P_{NM}$. In the present example, labelling efficiencies denote the fractions of target analytes and non-target molecules hybridized to a labelling agent, respectively. Labelling efficiencies may either be directly measured by e.g. melting curve analysis or estimated based on the oligonucleotide sequences of the target analyte, the non-target molecule and the labelling agent.

The probability ($P_{TA}(n)$) that a capture site hosting n individual target analytes is successfully labeled with at least one labelling agent is $$P_{TA}(n)=1-(1-P_{TA})^n \qquad \text{Eqn. 21}$$

And likewise the probability ($P_{NM}(n)$) that a capture site hosting n individual non-target molecules is successfully labeled with at least one labelling agent is $$P_{NM}(n)=1-(1-P_{NM})^n \qquad \text{Eqn. 22}$$

Furthermore, the distribution of capture sites containing exactly n target analytes ($f_{TA}(n)$) is given by the Poisson distribution as $$f_{TA}(n) = \frac{(N_{TA}/N_C)^n \exp(-N_{TA}/N_C)}{n!} \qquad \text{Eqn. 23}$$

Consequently, the number of capture sites exhibiting exactly n target analytes ($C_{TA}(n)$) is $C_{TA}(n)=N_C \cdot f_{TA}(n)$. Likewise, the distribution of capture sites containing exactly n non-target molecules ($f_{NM}(n)$) is given by Eqn. 24 and the number of capture sites exhibiting exactly n non-target molecules ($C_{NM}(n)$) is $C_{NM}(n)=N_C \cdot f_{NM}(n)$.

$$f_{NM}(n) = \frac{(N_{NM}/N_C)^n \exp(-N_{NM}/N_C)}{n!} \qquad \text{Eqn. 24}$$

For an analysis comprising a number of repetitive detection cycles re-applying the same type of labelling agent in the labelling step, the average number of consecutively labelled capture sites comprising target analytes for each detection step ($L_{TA}(x)$), where x represents the number of detection cycles, is found by summing all possible configurations of capture sites having at least one labelling agent $$L_{TA}(x) = \sum_{n=1}^{N_{TA}} C_{TA}(n) P_{TA}(n)^x = N_C \sum_{n=1}^{N_{TA}} f_{TA}(n) P_{TA}(n)^x = \qquad \text{Eqn. 25}$$

$$N_C \sum_{n=1}^{N_{TA}} \frac{(N_{TA}/N_C)^n \exp(-N_{TA}/N_C)}{n!} (1-(1-P_{TA})^n)^x$$

Likewise, the average number of consecutively labelled capture sites comprising non-target molecules for each detection cycle ($L_{NM}(x)$), where x represents the number of repetitions, is given as $$L_{NM}(x) = N_C \sum_{n=1}^{N_{NM}} f_{NM}(n) P_{NM}(n)^x = \qquad \text{Eqn. 26}$$

$$N_C \sum_{n=1}^{N_{NM}} \frac{(N_{NM}/N_C)^n \exp(-N_{NM}/N_C)}{n!} (1-(1-P_{NM})^n)^x$$

In addition to the sequence-dependent labelling of target analytes and non-target molecules, labelling agents may also become non-specifically retained on the capture sites by e.g. hydrophobic or electrostatic interactions. In the present example, we assume that the number of non-specifically retained labelling agents ($L_{NSR}(x)$) may be calculated as $$L_{NSR}(x)=f_{NSR}^x N_C \qquad \text{Eqn. 27}$$

Here x is the number of repetitions and $f_{NSR}$ is the fraction of compartments hosting at least one non-specifically retained labelling agent. A value for $f_{NSR}$ may be obtained experimentally by executing a detection cycle in the absence of both target analytes and non-target molecules and count the number of capture sites displaying a signal. Consequently, the expected number of capture sites exhibiting a detectable signal after compartmentalization as a function of the number of detection cycles ($C_T(x)$) is found by summing the contributions from sequence-dependent labelling of target analytes, sequence-dependent labelling of non-target molecules and sequence-independent non-specifically retained labelling agent:

$$C_T(x)=L_{TA}(x)+L_{NM}(x)+L_{NSR}(x) \quad \text{Eqn. 28}$$

In FIG. 18, the contributions from $L_{TA}$, $L_{NM}$ and $L_{NSR}$ are plotted for four different configurations. In FIG. 18, values for $C_T$, $L_{TA}$, $L_{NM}$ and $L_{NSR}$ are calculated for (A) $N_{TA}=10$, $N_{NM}=10,000$, $N_C=100,000$, $P_{TA}=0.9$, $P_{NM}=0.05$ and $f_{NSR}=0$, (B) $N_{TA}=10$, $N_{NM}=100,000$, $N_C=100,000$, $P_{TA}=0.9$, $P_{NM}=0.05$ and $f_{NSR}=0.05$, (C) $N_{TA}=10$, $N_{NM}=1,000,000$, $N_C=100,000$, $P_{TA}=0.9$, $P_{NM}=0.05$ and $f_{NSR}=0$ and (D) $N_{TA}=10$, $N_{NM}=1,000,000$, $N_C=1,000,000$, $P_{TA}=0.9$, $P_{NM}=0.05$ and $f_{NSR}=0.05$.

In FIG. 18A-D, the target analyte is greatly outnumbered by both non-target molecules and non-specifically retained labelling agents, which would otherwise compromise the accuracy of a conventional single detection cycle experiment. The presence of a 5% population ($f_{NSR}=0.05$) of capture sites exhibiting non-specifically retained labelling agents is quickly eliminated within the first 3-4 detection cycles. Furthermore, the false-positive signals originating from the non-target molecules are quickly reduced several orders of magnitude within the first 3-6 detection cycles, while leaving the specific signals from the target analytes substantially unchanged.

Example 8

Evaluation of the Limit-of-Detection (LOD), Limit-of-Quantification (LOQ) and Dynamic Range (DR) of a Single Molecule Digital Counting Analysis as a Function of the Number of Applied Detection Cycles.

Table 1 and Table 2 lists simulated values of the average number of false-positive capture sites ($N_{FP}$), the standard deviation of the number of signal-positive capture sites ($\delta N_{FP}$), the limit-of-detection (LOD), the limit-of-quantification (LOQ) and the dynamic range (DR) for analyses exhibiting one (C1), two (C2), times (C3) and four (C4) detection cycles.

In the present example, $N_{FP}$-values were obtained by simulation by specifying values for the number of capture sites ($N_C$), the number of target analytes ($N_{TA}$), the number of non-target molecules ($N_{NM}$), the labelling efficiency of target analytes by labelling agents ($P_{TA}$), the labelling efficiency of non-target molecules by labelling agents ($P_{NM}$) and the fraction of non-specifically retained labelling agents ($f_{NSR}$), cf. Example 7.

To initialize the simulation, each capture site was assigned a unique index. To simulate the capture step, the simulation algorithm randomly distributed target analytes and non-target molecules among the available number of capture sites. The capture site assigned to the individual target analyte or non-target molecule was not changed for the remaining part of the simulation. Next, the labelling step was simulated by—for each capture site—to calculate $P_{TA}$(n) and $P_{NM}$(n) according to Eqn. 21-22, where n represents the total number of target analytes and non-target molecules present at the capture site, respectively, and next draw two random values between 0 and 1. If the first random value was less than $P_{TA}$(n), the capture site was considered to contain a target analyte/labelling agent complex. If the second random value was less than $P_{NM}$(n), the capture site was considered to contain a non-target molecule/labelling agent complex. In both cases, the capture site was registered as labeled, and otherwise not.

To account for non-specifically retained labelling agents, $f_{NSR} \cdot N_C$ capture sites were randomly selected and registered as labeled. A list of the unique indices of all capture sites along with their status as labeled or not labeled was compiled and saved at the end of each labeling step. To simulate a subsequent detection cycle, a new simulated labelling process was conducted and a new list of unique indices and labelling status for all capture sites was compiled.

After all detection cycles had been simulated, the labelling lists for each detection cycle was compared to each other to identify capture sites persistently labelled in all detection cycles. The outcome of a single simulation was the number of persistently labelled capture sites ($N_{PL}$). To obtain an $N_{FP}$-value, 1000 simulations applying the same initialization parameters were conducted and $N_{FP}$ calculated as the average value of all recorded $N_{PL}$-values. Likewise, to obtain an $\delta N_{Fp}$-value the standard deviation of all recorded $N_{PL}$-values was calculated. To obtain LOD-, LOQ- and DR-values the simulation was conducted with $N_{TA}=0$, such that only false-positive events would result, and the simulation hence would provide an estimate of the inherent counting error of the measurement. The LOD-, LOQ- and DR-values were calculated as $N_{FP}+3\delta N_{FP}$, $N_{FP}+10\delta N_{FP}$ and $N_C$/LOQ, respectively.

For the simulation results shown in Table 1 and Table 2, the following values were applied: $N_C=10^5$, $N_{TA}=0$, $P_{NM}=0.05$, $f_{NSR}=0$ and $N_{NM}=10^3$-$10^5$. As can be seen from the tables, the LOD-, LOQ- and DR-values of the test become increasingly better (the values decrease) each time a detection cycle is repeated, which is due to less false-positive detections ($N_{FP}$). However, the number of non-target molecules in the sample affects the LOD-, LOQ- and DR-values adversely, which is due to a higher proportion of false-positive capture sites relative to the total number of available capture sites.

TABLE 1

Theoretical analytical performance of a SELMA test for samples containing 1,000 (left) and 10,000 (right) non-target molecules.

| | $N_{Nm}$ = 1,000 | | | | | $N_{Nm}$ = 10,000 | | | | |
|---|---|---|---|---|---|---|---|---|---|---|
| | $N_{FP}$ | $\delta N_{FP}$ | LOD | LOQ | DR | $N_{FP}$ | $\delta N_{FP}$ | LOD | LOQ | DR |
| C1 | 49.4 | 6.8 | 70 | 118 | 842 | 499.1 | 22.6 | 567 | 725 | 138 |
| C2 | 2.4 | 1.7 | 7 | 19 | 4,942 | 28.6 | 5.1 | 44 | 80 | 1,234 |
| C3 | 0.1 | 0.4 | 1 | 4 | 19,284 | 1.4 | 1.2 | 5 | 13 | 7,140 |
| C4 | 0 | 0 | 0 | 0 | 100,000 | 0.1 | 0.3 | 1 | 3 | 26,175 |

TABLE 2

Theoretical analytical performance of a SELMA test for samples containing 100,000 (left) and 1,000,000 (right) non-target molecules.

| | $N_{Nm}$ 100,000 | | | | | $N_{Nm}$ 1,000,000 | | | | |
|---|---|---|---|---|---|---|---|---|---|---|
| | $N_{FP}$ | $\delta N_{FP}$ | LOD | LOQ | DR | $N_{FP}$ | $\delta N_{FP}$ | LOD | LOQ | DR |
| C1 | 4,888 | 87.6 | 5,151 | 5,764 | 17 | 39,349 | 153 | 39,810 | 40,834 | 2 |
| C2 | 462 | 27.2 | 544 | 734 | 136 | 16,403 | 106 | 16,720 | 17,461 | 6 |
| C3 | 53 | 6.8 | 73 | 121 | 820 | 7,166 | 64 | 7,356 | 7,801 | 13 |
| C4 | 7 | 2.6 | 15 | 33 | 2,919 | 3,255 | 46 | 3,392 | 3,712 | 27 |

SEQUENCE LISTING

SEQ ID NO: 1:
ACA TAG TTG ACA CG

SEQ ID NO: 2:
5'-TCT GTC GTA GGC ACA GAG CGG TCT TAC GGC CAG TCG CGT GTC AAC TAT GT-3'

SEQ ID NO: 3:
5'-GCC TAC GAC AGA-3'

SEQ ID NO: 4:
5'-TCT GTC GTA GGC ACA GAG CGG TCT TAC GGC CAG TCG CGT GTC AAC TAT-3'

SEQ ID NO: 5:
5'-TCT GTC GTA GGC ACA GAG CGG TCT TAC GGC CAG TCG CGT GTC CAC TAT-3'

SEQ ID NO: 6:
5'-GTG CCT ACG ACA GA-3'

SEQ ID NO: 7:
5'-ATA GTT GAC AC-3'

The invention claimed is:

1. A method for digital counting analysis of a sample potentially containing at least one analyte, wherein the sample has been contacted with a solid phase having a plurality of discrete capture sites, each site being capable of capturing the at least one analyte, which method comprises at least two detection cycles in which the same analyte is labelled or re-labelled with a labelling agent, where each detection cycle comprises the steps of
 a) triggering a signal from captured and labelled or re-labelled analyte(s),
 b) recordation of the number and positions of capture sites exhibiting a signal from the captured and labelled or re-labelled analyte(s), and
 c) before a further detection cycle is performed, deactivation of the signal(s)
 wherein the step of signal deactivation is selected from
  i. detaching and removing the labelling agent from the captured analyte,
  ii. deactivating the ability of the labelling agent to facilitate a signal or
  iii. a combination of i) and ii).

2. The method according to claim 1, wherein the sample and the solid phase having a plurality of discrete capture sites are compartmentalized prior to or during capturing of the at least one analyte.

3. The method according to claim 1, wherein the captured analyte(s) and labelling agent are compartmentalized prior to or during labelling of the at least one analyte.

4. The method according to any one of claim 1, wherein the analyte(s) is labelled by adding a labelling agent in a labelling step in each detection cycle before step a).

5. The method according to any one of claim 1, wherein the captured analyte(s) is labelled by adding a labelling agent in a labelling step prior to or during capturing of the analyte(s) on the solid phase, and wherein step c) before a further detection cycle is performed is followed by a re-labelling step, wherein the captured analyte(s) is labelled by adding the labelling agent.

6. The method according to any one of claim 1, wherein the captured and labelled analyte(s) is compartmentalized to produce liquid compartments containing at least one analyte.

7. The method according to claim 1, where the sample contains a target analyte and a non-target compound, where the target analyte is captured by the capture site with capture efficiency $C_1$, where the non-target compound is captured by the capture site with capture efficiency $C_2$ and $C_1 \geq C_2$, where the target analyte is labelled by a first labelling agent with labelling efficiency $L_1$, where the non-target compound is labelled by the first labelling agent with labelling efficiency $L_2$ and $L_1 \geq L_2$, where the number of detection cycles $N_c$ is adjusted such that the ratio $\alpha = C_1 N_1^{Nc}/C_2 N_2^{Nc}$ is between 1-10, preferably between 10-100, preferably between 100-1000, preferably between 1,000-10,000, preferably between 10,000-100,000, preferably greater than 100,000, and where each detection cycle applies the first labelling agent in the labelling step.

8. The method according to claim 7, which includes a false-positive detection cycle, where a second labelling agent is applied instead of the first labelling agent in the labelling step, where the non-target compound is labelled by the second labelling agent with labelling efficiency $L_1$, where the target analyte is labelled by the second labelling agent with labelling efficiency $L_2$ and $L_1 \geq L_2$.

9. The method according to claim 1, which includes a false-positive detection cycle, which false-positive detection cycle does not comprise any labelling steps.

10. The method according to claim 1, wherein the capturing of the at least one analyte from the sample is performed using one or more capture probes specific to the analyte and where the capture probes are attached to the solid phase.

11. The method according to claim 1, wherein the labeling agent is deactivated by detachment from the captured analyte and removed by flushing.

12. The method according to claim 10, wherein the captured analytes become covalently coupled to the capture probe(s) subsequent to capture.

13. The method according to claim 1 for reduction of false-positive detections and/or background noise in single molecule digital counting analysis of a sample.

14. A method for digital counting analysis of a sample containing more than one analyte types, wherein the sample has been contacted with a solid phase having a plurality of discrete capture sites, each site being capable of capturing a specific analyte type, which method comprises at least two detection cycles in which at least one of the analyte types is labelled or relabeled with a labelling agent, where each detection cycle comprises the steps of
   a) triggering a signal from captured and labelled or re-labelled analyte(s),
   b) recordation of the number and positions of capture sites exhibiting a signal from the captured and labelled or re-labelled analyte(s), and
   c) before a further detection cycle is performed, deactivating the signal(s)
wherein the step of signal deactivation is selected from
   i. detaching and removing the labelling agent from the captured analyte,
   ii. deactivating the ability of the labelling agent to facilitate a signal or
   iii. a combination of i) and ii).

15. The method according to claim 14, wherein the capturing of two or more analyte types from the sample is by using two or more capture probes types each specific to one of the analyte types.

16. The method according to claim 15, wherein different capture probes are organized in different spatial regions.

* * * * *

UNITED STATES PATENT AND TRADEMARK OFFICE
CERTIFICATE OF CORRECTION

| | | |
|---|---|---|
| PATENT NO. | : 11,035,854 B2 | Page 1 of 1 |
| APPLICATION NO. | : 16/320615 | |
| DATED | : June 15, 2021 | |
| INVENTOR(S) | : Andreas Hjarne Kunding | |

It is certified that error appears in the above-identified patent and that said Letters Patent is hereby corrected as shown below:

On the Title Page

At Item (30) under the "Foreign Application Priority Data," the following priority document was omitted and should be added:
October 7, 2016 (WO) .......................... PCT/EP2016/074045.

In the Claims

At Column 87, Claim 4, Line 65, the text "any one of claim 1" should be changed to -- claim 1 --.

At Column 88, Claim 5, Line 38, the text "any one of claim 1" should be changed to -- claim 1 --.

At Column 88, Claim 6, Line 45, the text "any one of claim 1" should be changed to -- claim 1 --.

At Column 88, Claim 7, Line 57, the text " $a = \dfrac{C_1 N_1^{NC}}{C_2 N_2^{NC}}$ " should be changed to -- $a = \dfrac{C_1 L_1^{NC}}{C_2 L_2^{NC}}$ --.

Signed and Sealed this
Third Day of June, 2025

Coke Morgan Stewart
*Acting Director of the United States Patent and Trademark Office*

SEQUENCE LISTING

<160> NUMBER OF SEQ ID NOS: 7

<210> SEQ ID NO 1
<211> LENGTH: 14
<212> TYPE: DNA
<213> ORGANISM: Artificial sequence
<220> FEATURE:
<223> OTHER INFORMATION: PNA analogue of DNA sequence

<400> SEQUENCE: 1
acatagttga cacg                                                         14

<210> SEQ ID NO 2
<211> LENGTH: 50
<212> TYPE: DNA
<213> ORGANISM: Artificial sequence
<220> FEATURE:
<223> OTHER INFORMATION: Model oligonucleotide

<400> SEQUENCE: 2
tctgtcgtag gcacagagcg gtcttacggc cagtcgcgtg tcaactatgt                  50

<210> SEQ ID NO 3
<211> LENGTH: 12
<212> TYPE: DNA
<213> ORGANISM: Artificial sequence
<220> FEATURE:
<223> OTHER INFORMATION: Biotin-labelled DNA oligonucleotide

<400> SEQUENCE: 3
gcctacgaca ga                                                           12

<210> SEQ ID NO 4
<211> LENGTH: 48
<212> TYPE: DNA
<213> ORGANISM: Artificial sequence
<220> FEATURE:
<223> OTHER INFORMATION: Model target DNA

```
<400> SEQUENCE: 4
tctgtcgtag gcacagagcg gtcttacggc cagtcgcgtg tcaactat        48

<210> SEQ ID NO 5
<211> LENGTH: 48
<212> TYPE: DNA
<213> ORGANISM: Artificial sequence
<220> FEATURE:
<223> OTHER INFORMATION: Model non-target DNA

<400> SEQUENCE: 5
tctgtcgtag gcacagagcg gtcttacggc cagtcgcgtg tccactat        48

<210> SEQ ID NO 6
<211> LENGTH: 14
<212> TYPE: DNA
<213> ORGANISM: Artificial sequence
<220> FEATURE:
<223> OTHER INFORMATION: PNA-modified capture probe

<400> SEQUENCE: 6
gtgcctacga caga                                             14

<210> SEQ ID NO 7
<211> LENGTH: 11
<212> TYPE: DNA
<213> ORGANISM: Artificial sequence
<220> FEATURE:
<223> OTHER INFORMATION: Single stranded DNA label

<400> SEQUENCE: 7
atagttgaca c                                                11
```